US012735712B2

(12) United States Patent
Easley et al.

(10) Patent No.: US 12,735,712 B2
(45) Date of Patent: Sep. 15, 2026

(54) ELECTROCHEMICAL DETECTION NANOSTRUCTURE, SYSTEMS AND USES THEREOF

(71) Applicant: Auburn University, Auburn, AL (US)

(72) Inventors: Christopher J. Easley, Auburn, AL (US); Subramaniam Somasundaram, Auburn, AL (US)

(73) Assignee: Auburn University, Auburn, AL (US)

(*) Notice: Subject to any disclaimer, the term of this patent is extended or adjusted under 35 U.S.C. 154(b) by 407 days.

(21) Appl. No.: 18/158,466

(22) Filed: Jan. 23, 2023

(65) Prior Publication Data

US 2023/0257755 A1 Aug. 17, 2023

Related U.S. Application Data

(63) Continuation of application No. 16/440,113, filed on Jun. 13, 2019, now Pat. No. 11,560,565.

(60) Provisional application No. 62/684,227, filed on Jun. 13, 2018.

(51) Int. Cl.

| | |
|---|---|
| ***C12Q 1/68*** | (2018.01) |
| ***C12N 15/115*** | (2010.01) |
| ***C12Q 1/6816*** | (2018.01) |

(52) U.S. Cl.
CPC .......... *C12N 15/115* (2013.01); *C12Q 1/6816* (2013.01); *C12N 2310/122* (2013.01); *C12Q 2565/518* (2013.01)

(58) Field of Classification Search
USPC ......... 435/6.1, 6.11, 7.1, 91.1, 287.1, 287.2; 436/94, 501; 536/23.1, 24.3, 24, 33
See application file for complete search history.

(56) References Cited

U.S. PATENT DOCUMENTS

| | | | |
|---|---|---|---|
| 5,635,352 | A | 6/1997 | Urdea et al. |
| 5,698,448 | A | 12/1997 | Soldin |
| 6,264,825 | B1 | 7/2001 | Blackburn et al. |
| 6,350,580 | B1 | 2/2002 | Sorge |
| 6,361,944 | B1 | 3/2002 | Mirkin et al. |
| 6,506,564 | B1 | 1/2003 | Mirkin et al. |

(Continued)

FOREIGN PATENT DOCUMENTS

| | | |
|---|---|---|
| EP | 1198591 A1 | 4/2002 |
| EP | 1806414 A2 | 7/2007 |

(Continued)

OTHER PUBLICATIONS

Arroyo-Curras et al.; Real-time measurement of small molecules directly in awake, ambulatory animals; Proceedings of the National Academy of Sciences; 114(4); pp. 645-650; Jan. 24, 2017.

(Continued)

*Primary Examiner* — Frank W Lu
(74) *Attorney, Agent, or Firm* — Barnes & Thornburg LLP

(57) ABSTRACT

Described herein are DNA-nanostructures that can be used in an assay to detect and/or quantify an analyte of interest. Aspects of the DNA-nanostructure can include a single DNA molecule composed of hairpin structural motifs, an anchor recognition moiety, and a signal moiety, where the anchor recognition moiety and the signal moiety are in effective proximity to each other such that the tethered diffusion of the signal molecule can be altered based upon binding status of the anchor recognition moiety. Also described herein are methods of making and using the DNA-nanostructures.

16 Claims, 23 Drawing Sheets

Specification includes a Sequence Listing.

(56) References Cited

U.S. PATENT DOCUMENTS 6,750,016 B2 6/2004 Mirkin et al.
6,767,702 B2 7/2004 Mirkin et al.
6,773,884 B2 8/2004 Mirkin et al.
6,984,491 B2 1/2006 Mirkin et al.
7,005,265 B1 2/2006 Fan et al.
7,169,556 B2 1/2007 Park et al.
7,291,457 B2 11/2007 Miller et al.
7,803,542 B2 9/2010 Xiao et al.
7,807,352 B2 10/2010 Rabbani et al.
8,003,374 B2 8/2011 Heeger et al.
9,335,292 B2 5/2016 Hu et al.
10,852,274 B2 12/2020 Easley et al.
11,505,799 B2 11/2022 Inapuri et al.
11,560,565 B2 1/2023 Easley et al.
2001/0024788 A1 9/2001 Hashimoto
2002/0006617 A1 1/2002 Fan et al.
2002/0012943 A1 1/2002 Fowlkes et al.
2002/0172953 A1 11/2002 Mirkin et al.
2003/0022150 A1 1/2003 Sampson et al.
2003/0077642 A1 4/2003 Fritsch et al.
2003/0108922 A1 6/2003 Fritsch et al.
2004/0106190 A1 6/2004 Yang et al.
2004/0191801 A1 9/2004 Heeger et al.
2005/0096288 A1 5/2005 Guevara
2005/0112605 A1 5/2005 Heeger et al.
2005/0164286 A1 7/2005 Ouchi et al.
2005/0202449 A1 9/2005 Getts et al.
2006/0228703 A1 10/2006 Hartwich et al.
2006/0234253 A1 10/2006 Hasul et al.
2007/0084721 A1 4/2007 Hsung et al.
2007/0236224 A1 10/2007 Augustyniak et al.
2008/0076139 A1 3/2008 Singh
2008/0302666 A1 12/2008 Benner et al.
2009/0042735 A1 2/2009 Blair et al.
2009/0305264 A1 12/2009 West et al.
2010/0035248 A1 2/2010 Levicky et al.
2010/0075319 A1 3/2010 Lohse
2010/0248231 A1 9/2010 Wei et al.
2010/0297654 A1 11/2010 Heyduk
2011/0053788 A1 3/2011 Bamdad et al.
2011/0143955 A1 6/2011 Weiner
2012/0021426 A1 1/2012 Takoh et al.
2012/0028242 A1 2/2012 Heyduk et al.
2015/0050645 A1 2/2015 Takoh
2019/0250120 A1 8/2019 Korri-Youssoufi et al.
2021/0055260 A1 2/2021 Easley et al.
2023/0042710 A1 2/2023 Ford et al.

FOREIGN PATENT DOCUMENTS

WO WO01/040511 A2 6/2001
WO WO01/051665 A2 7/2001
WO WO01/073123 A2 10/2001
WO WO02/018643 A2 3/2002
WO WO02/046472 A2 6/2002
WO WO03/035829 A2 5/2003
WO WO2004/023128 A1 3/2004
WO WO2006/096185 A2 9/2006
WO WO2008/001376 A2 1/2008
WO WO2008/054517 A2 5/2008
WO WO2018/111745 A1 6/2008
WO WO2011/017382 A2 2/2011
WO WO2011/050069 A1 4/2011
WO WO2011/161420 A2 12/2011
WO WO2015/150482 A1 10/2015
WO WO2017/192737 A1 11/2017
WO WO2018/011412 A1 1/2018

OTHER PUBLICATIONS

Baker et al.; An electronic aptamer-based small-molecule sensor for the rapid, label-free detection in adulterated samples and biological fluids; Journal of the American Chenical Society; 128(10); pp. 3138-3139; Mar. 2006.

Bonham et al.; Detection of IP-10 protein marker in undiluted blood serum via an electrochemical e-dna scaffold sensor; Analyst; 138(19); pp. 5580-5583; 9 pages (Author Manuscript); Oct. 7, 2013.

Campos et al.; Amperometric detection of lactose using ?-galactosidase immobilized in layer films; ACS Applied Materials and Interfaces; 6(14); pp. 11657-11664; 8 pages (Author Manuscript); Jul. 11, 2014.

Carrillo et al.; The multiple sequence aligment problem in biology; SIAM Journal on Applied Mathematics; 48(5); pp. 1073-1082; Oct. 1988.

Cash et al.; An electrochemical sensor for the detection of protein-small molecule interactions directly in serum and other complex matrices; Journal of the American Chemical Society: 131(20); pp. 6955-6957; May 4, 2009.

De Crozals et al.; Methylene blue phosphoramidite for DNA labelling; ChemCommun; vol. 51(2); pp. 4458-4461; Mar. 14, 2014.

Denman et al.; Continuous differential monitoring of the spend dialysate glucose level: clinical evaluation; Sensors and Actuators B: Chemical; 44 (1-3); pp. 304-308; Oct. 1, 1997.

Deng et al.; Sensitive bifunctional aptamer-based electrochemical biosensor for small molecules and protein; Analytical Chemistry; 81(24); pp. 9972-9978; Nov. 19, 2009.

Dirks et al.; A partition function algorithm for nucleic secondary structure including pseudoknots; Journal of Computational Chemisrty; 24(10); pp. 1664-1677; Oct. 2003.

Dirks et al.; An algorithm for computing nucleic acid base-pairing proabilities including pseudoknots; Journal of Computational Chemisrty; 25(10); pp. 1295-1304; Jul. 30, 2004.

Dirks et al.; Paradigms for computational nucleic acid design; Nucleic Acid Research; 32(4); pp. 1392-1403; Feb. 27, 2004.

Dirks et al.; Thermodynamic analysis of interacting nucleic acid strands; SIAM Rev.; 49(1); pp. 65-88; (the year of publication is sufficiently earlier than the effective U.S. filing date and any foreign priority date so that the particular month of publication is not in issue) 2007.

Dryden et al.; Dstat: A versatile, open-source potentiostat for electroanalysis and integration; PLOS One; DOI: 10.1371/journal.pone.0140349; 17 pages; Oct. 28, 2015.

Du et al.; Multifunctional label-free electrochemical biosensor based on an integrated aptamer; Analytical Chemistry; 80(13); pp. 5110-5117; Jun. 4, 2008.

Fan et al.; A Competitor-switched electrochemical sensor for detection of dna; Chin. J. Chem.; 28; pp. 1978-1982; (the year of publication is sufficiently earlier than the effective U.S. filling date and any foreign priority date so that the particular month of publication is not in issue) 2010.

Fan et al.; Electrochemical interrogation of conformational changes as a reagentless method for the sequence-specific detection of dna; Proceedings of the National Academy of Sciecnes; 100(16); pp. 9134-9137; Aug. 5, 2003.

Ferapontova et al.; An rna aptamer-based electrochemical biosensor for detection of theophylline in serum; Journal of the American Chemical Society; 130(13); pp. 4256-4258; Apr. 2, 2008.

Ferguson et al.; Real-time, aptamer-based tracking of circulating therapeutic agents in living animals; Science Translational Medicine; 5(213); pp. 213ra165, 11 pages; Nov. 27, 2013.

Garcia-Gonzalez et al.; Methylene blue covalently attached to single stranded DNA as electroactive label for potential bioassays; Sensors and Actuators B: Chemical; vol. 191; pp. 784-790; Feb. 1, 2014.

Hirsch et al.; Easily reversible desthiobiotin binding to streptavidin, avidin, and other biotin-binding proteins: uses for protein labeling, detection, and isolation; Analytical biochemistry; 308(2); pp. 343-357.

Hu et al.; A reusable electrochemical proximity assay for highly selective, real-time protein quantitation in biological matrices; Journal of the American Chemical Society: 136(23); pp. 8467-8474; May 30, 2014.

(56) References Cited

OTHER PUBLICATIONS

Huang et al.; Random walk on a leash: a simple single-molecule diffusion model for surface-tethered redox molecules with flexible linkers; Journal of the American Chemical Society; 135(34); pp. 12808-12817; Aug. 20, 2013.
Idili et al.; Folding-upon-binding and signal-on electrochemical dna sensor with high affinity and specificity: Analytical Chemistry; 86(18); pp. 9013-9019; Jul. 3, 2014.
Jakubowska; Signal processing in electrochemistry; Electroanalysis; 23(3); pp. 553-572; Mar. 2011.
Jeyarajah et al.; Lipoprotein particle analysis by nuclaer magnetic resoance spectroscopy; Clinics in Laboratory Medicine; 26(4); pp. 847-870; Dec. 2006.
Kaess et al.; The lipoprotein sub-fraction profile hertability and indentification of quantitative trait loci; Journal of Lipid Research; 49(4); pp. 715-723; Apr. 2008.
Kang et al.; Comparing the properties of electrochemical-based dna sensors employing different redox tags, Analytical Chemistry; 81(21); pp. 9109-9113; 12 pages (Author Manuscript); Oct. 7, 2009.
Kang et al.; Expanding the scope of protein-detecting electrchemical dna "scaffold" sensors; ACS Sensors; 3(7); pp. 1271-1275; 12 pages (Author Manuscript); Jun. 2018.
Kick et al.; EGNAS: an exhaustive dna sequence design algorithm; BMC Bioinformatics; 13(1); pp. 138; 17 pages; http://www.biomedcentral.com/1471-2105/13/138; Dec. 2012.
Labib et al.; Electrochemical methods for the analysis of clinically relevant biomolecules; Chemical Reviews; 116(16); pp. 9001-9090; Jul. 18, 2016.
Lee et al.; Fabricating RNA Microarrays with RNA? DNA Surface Ligation Chemistry. Analytical chemistry; 77(23); pp. 7832-7837; Dec. 1, 2005.
Li et al.; A simple assay to amplify the electrochemical signal by the aptamer based biosensor modified with CdS hollow nanospheres; Biosensors and Bioelectronics; 26(8); pp. 3531-3535; Apr. 15, 2011.
Li et al.; Target-responsive structural switching for nucleic acid-based sensors, Accounts of Chemical Research; 43(5); pp. 631-641; Mar. 11, 2010.
Lin et al.; Label-free aptamer-based electrochemical impedance biosensor for 17? estradiol; Analyst; 137(4); pp. 819-822; Feb. 2012.
Liu et al.; Aptamer-based electrochemical biosensors for interferon gamma detection; Analytical Chemistry; 82(19); pp. 8131-8136; Sep. 3, 2010.
Lu et al.; Aptamer-based electrochemical sensors that are not based on the target binding-induced conformational change of aptamers; Analyst; 133(9); pp. 1256-1260; Sep. 2008.
Lubin et al.; Effects of probe length, probe geometry, and redox-tag placement on the performance of the electtrochemical e-dna sensor; Analytical Chemistry; 81(6); pp. 2150-2158; Feb. 12, 2009.
Mage; Closed-loop control of circulating drug levels in live animals; Nature Biomedical Engineering; 1(5); DOI:10.1038/s415551-017-0070, 10 pages; May 2017.
Mahshid et al.; A highly selective electrochemical dan-based sensor that employs steric hindrance effects to detect proteins directly in whole blood; Journal of the American Chemical Society; 137(50); pp. 15596-15599; Sep. 24, 2015.
Mahshid et al.; Biomolecular steric hindrance effects are enhanced on nanostructured microelectrodes; Analytical Chemistry; 89(18); pp. 9751-9757; Sep. 5, 2017.
Mahshid et al.; Electrochemical dna-based immunoassay that employs steric hindrance to detect small molecules directly in whole blood; AACS Sensors; 2(6); pp. 718-723; May 25, 2017.
Needleman et al.; A general method applicable to the search for similarities in the amino scid sequence of two proteins; Journal of Molecular Biology; 48(3); pp. 443-453; Mar. 1970.
Sacks et al.; Clinical review 163: cardiovascular endocrinology: low-density lipoprotein size and cardovascular disease: a reappraisal; The Journal of Clinical Endocrinology and Metabolism; 88(10); pp. 4525-4532; Oct. 2003.
Schoukroun-Barnes et al.; Reagentless, structure-switching, electrochemical aptamer-based sensors; Annual Review of Analtyical Chemistry; 9(1); pp. 163-181; 23 pages (Author Manuscript) Jun. 2016.
Sheth et al.; Decapping and decay of messenger RNA occur in cytoplasmic processing bodies; Science; 300; pp. 805-808; May 2003.
Sigma-Aldrich; Self-assembled monolayers: advantages of pure alkanethiols; 4 pages retrieved from the internet (https://www.sigmaaldrich.com/technical-documents/articles/material-matters/self-assembled-monolayers.html) on Dec. 10, 2019.
Silva et al.; Gold electrode modified by self-assembled monolayers of thiolis to determine dna sequences hybridization; Journal of Chemical Sciences; 122(6); pp. 911917; Nov. 2010.
Somasundaram et al.; A nucleic acid nanostructure built through on-electrode ligation for electrochemical detection of a board range of analytes; Journal of the American Chemical Society; 141(29); pp. 11721-11726; 14 pages; (Author Manuscript); Jun. 2019.
Somasundaram et al.; Understanding signal and background in a thermally resolved, single-branched dna assay using sqaure wave voltammetry; Analytical Chemistry; 90(50); pp. 3584-3591; 18 pages. (Author Manuscript); Jan. 31, 2018.
Suna et al.; 1H NMR metabolomics of plasma lipoprotein subclasses: elucidation of metabolic clustering by self-organizing maps; NMR in Biomedicine; 20(7); pp. 658-672; Nov. 2007.
Tong et al.; Simply amplified electrochemical aptasensor of ochratoxin a based on exonuclease-catalyzed target; Biosensors and Bioelectronics; 29(1); pp. 97-101; Nov. 15, 2011.
Turner: Biosensors: sense and sensibility; Chemical Society Reviews; 42(8); pp. 3184-3196; (the year of publication is sufficiently earlier than the effective U.S. filing date and any foreign priority date so that the particular month of publication is not in issue) 2013.
Wang et al.; A sensitive ligase-based atp electrochemical assay using molecular beacon-like dna; Biosensor and Bioelectronics; 25(9); pp. 2101-2106; May 2010.
White et al.; Exploiting binding changes in probe flexibility for the optimization of electrochemical biosensors; Analytical Chemistry; 82(1); pp. 73-76; 10 pages (Author Manuscript); Dec. 10, 2009.
Wolfe et al.; Constrained mullistale sequence design for nucleic acid reaction pathway engineering; Journal of American Chemical Society: 139(8); pp. 3134-3144; Feb. 13, 2017.
Wolfe et al.; Sequence design for a test tube of interacting nucleic acid strands; ACS Synthetic Biology; 4(10); pp. 1086-1100; Oct. 20, 2014.
Wu et al.; Reusable electrochemical sensing platform for highly sensitive detection of small molecules based on structure-switching signal aptamers; Analytical Chemistry; 79(7); pp. 2933-2939; Apr. 2007.
Xiao et al.; A reagentless signal-on architecture for electronic, aptamer-based sensors via target-induced strand displacement; Journal of the American Chemical Society; 127(51); pp. 17990-17991; (Author Manuscript); Dec. 28, 2005.
Xiao et al.; Preparation of electrode-immobilized, redox-modified oligonucleotides for electrochemical dna and aptamer-based sensing; Nature Protocols; 2(11); pp. 2875-2880; Nov. 2007.
Yeung et al.; Electrochemical real-time polymerase chain reaction; Journal of the American Chemical Society; 128(41); pp. 13374-13375; Oct. 18, 2006.
Zadeh et al.; Nucleic acid sequence design via efficient ensemble defect optimization; Journal of Computational Chemistry; 32(3); pp. 439-452; Feb. 2011.
Zadeh et al.; NUPACK: analysis and design of nucleic acid systems; Journal of computational Chemistry; 32(1); pp. 170-173; Jan. 15, 2011.
Zhang et al.; Electrochemical aptasensor based on proximity-dependent surface hybridization assay for protein detection; Electroanalysis: An International Journal Devoted to Fundamental and Practical Aspects of Electroanalysis; 21(11); pp. 1327-1333; Jun. 2009.
Zhang et al.; Electrochemical aptasensor based on proximity-dependent surface hybridization assay for single-step, reusable,

(56) References Cited

OTHER PUBLICATIONS sensitive protein detection; Journal of the American Chemical Society; 129(50); pp. 15448-15449; Published on line Nov. 22, 2007.
Zhao et al.; A label-free electrochemilumescent sensor for atp detection based on atp-dependent ligation; Talanta; 154; pp. 492-497; Jul. 2016.
Zhou et al.; Steric hindrance assay for secreted factors in stem cell culture; ACS Sensors; 2(4); pp. 495-500; Apr. 17, 2017.
Zymek et al.; The role of platelet-derived growth factor signal in healing mycardial infarcts; Journal of the American college of Cardiology; 48(11); pp. 2315-2323; Dec. 5, 2006.
Somasundaram et al.; U.S. Appl. No. 17/616,338 entitled "Assay method for point of care quantification of an immunophilin-binding immunosuppressant drug," filed Dec. 3, 2021.

Anti-digoxigenin (polycolonal)

ELECTROCHEMICAL DETECTION NANOSTRUCTURE, SYSTEMS AND USES THEREOF

CROSS-REFERENCE TO RELATED APPLICATIONS

This application is a continuation of U.S. patent application Ser. No. 16/440,113, filed Jun. 13, 2019, entitled "Electrochemical Detection Nanostructure, Systems, and Uses Thereof," now U.S. Pat. No. 11,560,565, which claims the benefit of and priority to U.S. Provisional Patent Application No. 62/684,227, filed on Jun. 13, 2018, entitled "Nanostructure for Electrochemical Sensing of a Broad Range of Analytes," the contents of both which are incorporated by reference herein in its entirety.

STATEMENT REGARDING FEDERALLY SPONSORED RESEARCH

This invention was made with Government support CBET-1403495 awarded by the National Science Foundation and R01 DK093810 awarded by the National Institutes of Health. The Government has certain rights in the invention.

SEQUENCE LISTING

This application contains a sequence listing filed in electronic form as a .XML file entitled 14750-702.300.xml, created on May 1, 2023, having a file size of 28,054 bytes. The content of the sequence listing is incorporated herein in its entirety.

TECHNICAL FIELD

The subject matter disclosed herein is generally directed to electrochemical detection of analytes.

BACKGROUND

The past decade has attracted a renewed interest in developing electrochemical sensors for quantification of biomarkers and other analytes of interest, owing at least in part to their low cost and adaptability to point-of-care (POC) and point-of-use (POU) setups. This has a potential to significantly impact healthcare and other industries where POU setups are desired. Clinically relevant targets for POC and analytes of interest for POU in other industries can include a range of molecular classes including small molecules (e.g. chemical compounds), mid-size molecules (e.g. nucleic acids and peptides), and macromolecules (e.g. proteins and larger nucleic acids). To quantify through this range of molecular classes, most method development has drifted towards being target focused and has lacked generalizability. As such, there exists an urgent need to develop methods, compounds, reagents, and structures amenable to quantitative readout of multiple classes of clinically and other relevant targets.

SUMMARY

Described herein are aspects of a nanostructure that can be composed of a single continuous DNA molecule composed of: a first hairpin structural motif; a second hairpin structural motif, wherein the first hairpin structural motif and the second hairpin structural motif are attached to each other via a first segment of single stranded DNA; an anchor recognition moiety, wherein the anchor recognition moiety is coupled to the single continuous DNA molecule; a signal moiety, wherein the signal moiety is coupled to the single continuous DNA molecule, wherein the signal moiety and the anchor recognition moiety are in effective proximity to each other; and a second segment of single stranded DNA, wherein the second segment of single stranded DNA is attached to the second structural motif such that it forms a single stranded tether region at one end of the single continuous DNA molecule. In aspects, the second segment of single stranded DNA can have a terminal base and wherein the terminal base is modified to comprise a reactive group capable of attaching to a surface of an electrode or non-electrode support. The reactive group can be selected from the group of: a carboxyl group, amino group, aromatic amine group, a chloromethyl group, an amide group, a hydrazide group, a hydroxyl, a thiol, an epoxy, and combinations thereof. The DNA nanostructure can include a linker having a reactive group capable of attaching to a surface of an electrode or non-electrode support, wherein the linker is attached to the terminal base of the second segment of single stranded DNA. The reactive group of the linker can be selected from the group of: a carboxyl group, amino group, aromatic amine group, a chloromethyl group, an amide group, a hydrazide group, a hydroxyl, a thiol, an epoxy, and combinations thereof. The single continuous DNA molecule has a sequence that is 1-100% identical to any one of SEQ ID NOs: 7-8J signal moiety can be a redox molecule. In aspects, the signal moiety can be methylene blue. In aspects, the signal moiety can be an optically active molecule. In aspects, the signal moiety can be a fluorescent dye.

Also described herein are systems that can include a nanostructure that can be composed of: a single continuous DNA molecule that can be composed of: a first hairpin structural motif; a second hairpin structural motif, wherein the first hairpin structural motif and the second hairpin structural motif are attached to each other via a first segment of single stranded DNA; an anchor recognition moiety, wherein the anchor recognition moiety is coupled to the single continuous DNA molecule; a signal moiety, wherein the signal moiety is coupled to the one end of the single continuous DNA molecule, wherein the signal moiety is in effective proximity to the anchor recognition moiety; and a second segment of single stranded DNA, wherein the second segment of single stranded DNA is attached to the second structural motif such that it forms a single stranded tether region at one end of the single continuous DNA molecule; and a support or electrode having a surface, wherein the nanostructure is coupled to the surface at a terminal base of the second segment of single stranded DNA. In aspects, the terminal base can be modified to comprise a reactive group capable of attaching to the surface. In aspects, the reactive group can be selected from the group of: a carboxyl group, amino group, aromatic amine group, a chloromethyl group, an amide group, a hydrazide group, a hydroxyl, a thiol, an epoxy, and combinations thereof. In aspects, the single continuous DNA molecule includes a linker having a reactive group capable of attaching to the surface, wherein the linker is attached to a terminal base of the second segment of single stranded DNA. In aspects, the linker's reactive group is selected from the group of: a carboxyl group, amino group, aromatic amine group, a chloromethyl group, an amide group, a hydrazide group, a hydroxyl, a thiol, an epoxy, and combinations thereof. In aspects, the signal moiety can be a redox molecule or a fluorescent molecule. In aspects, the single continuous DNA molecule has a sequence that is about 1%-100% identical to any one of SEQ ID NOs: 7-8. The surface can be an electrode surface, wherein the electrode surface includes an electrically conductive metal and the signal molecule is a redox molecule.

Also described herein are aspects of an assay that can include the steps of measuring an initial signal output from a nanostructure, wherein the nanostructure can be composed of a single continuous DNA molecule that can be composed of: a first hairpin structural motif; a second hairpin structural motif, wherein the first hairpin structural motif and the second hairpin structural motif are attached to each other via a first segment of single stranded DNA; an anchor recognition moiety, wherein the anchor recognition moiety is coupled to the single continuous DNA molecule; a signal moiety, wherein the signal moiety is coupled to the single continuous DNA molecule, wherein the signal moiety and the anchor recognition moiety are in effective proximity to each other; and a second segment of single stranded DNA, wherein the second segment of single stranded DNA is attached to the second structural motif such that it forms a single stranded tether region at one end of the single continuous DNA molecule; contacting a sample containing or suspected of containing an analyte of interest with the nanostructure and optionally an anchor molecule, allowing an analyte of interest present in the sample to specifically bind to the anchor recognition moiety or optionally the anchor molecule, allowing, the anchor molecule, when optionally included in the method, to specifically bind to the anchor recognition moiety; optionally washing unbound sample away from the nanostructure; and measuring a second signal output from the nanostructure after allowing the analyte of interest or optionally the anchor molecule to bind the anchor recognition moiety. In aspects, the nanostructure can be coupled to the surface of a non-electrode support or an electrode.

Also described herein are methods of making the DNA-nanostructure described herein. In aspects, the methods can include ligating 3 or more polynucleotide-based components in a reaction to form the DNA-nanostructure.

BRIEF DESCRIPTION OF THE DRAWINGS

Further aspects of the present disclosure will be readily appreciated upon review of the detailed description of its various embodiments, described below, when taken in conjunction with the accompanying drawings.

(FIG. 4A) Three DNAs: thiolated-DNA, anchor-DNA, and MB-DNA, are enzymatically ligated on-electrode into a single DNA nanostructure. (FIG. 4B) DNA melting analysis confirmed that ligated single DNA was stable (Tm=75° C.; black curve) compared to non-ligated DNA (Tm=55° C.; grey curve). (FIG. 4C) Ligated nanostructure was stable on electrodes even after four rinses (dark gray bars) while non-ligated structures were removed with a single water rinse (light gray bars).

(FIG. 5A) Streptavidin analyte with desthiobiotin as anchor recognition unit; (FIG. 5B) streptavidin calibration curve. (FIG. 5C) Antibody analyte with digoxigenin as anchor recognition unit; (FIG. 5D) anti-digoxigenin calibration curve.

(FIG. 6A) Biotin quantification probe with desthiobiotin as anchor recognition unit and streptavidin as anchor molecule; (FIG. 6B) calibration curve of biotin. (FIG. 6C) Digoxigenin probe with digoxigenin as anchor recognition unit and anti-digoxigenin as anchor; (FIG. 6D) digoxigenin calibration curve.

(FIG. 8B) Upon introduction of T4 DNA ligase, a stable non-equilibrium (covalent) DNA nanostructure is formed.

(FIG. 9B) Drop in the signal is observed after streptavidin binding.

(FIG. 10B) 3D CAD of the master to prepare electrochemical cell; (FIG. 10C) 3D printed PLA used for molding PDMS electrochemical cells. Using this mold, two sets of 18 individual electrochemical cell arrays were prepared and plasma oxidized to the GoG slide.

When the anchor binds with its recognition units, the diffusion is hindered suppressing the SWV signal. This attached anchor can be displaced when the recognition unit or its competitor comes in contact, due to the thermodynamic stability of the anchor binding with free molecule compared to the constrained one. This results in an increase in signal. By this strategy both anchor and anchor recognition unit can be quantified as signal-OFF direct and signal-ON indirect assay respectively, with anchor being large protein and small molecule as recognition unit.

Figure 16:
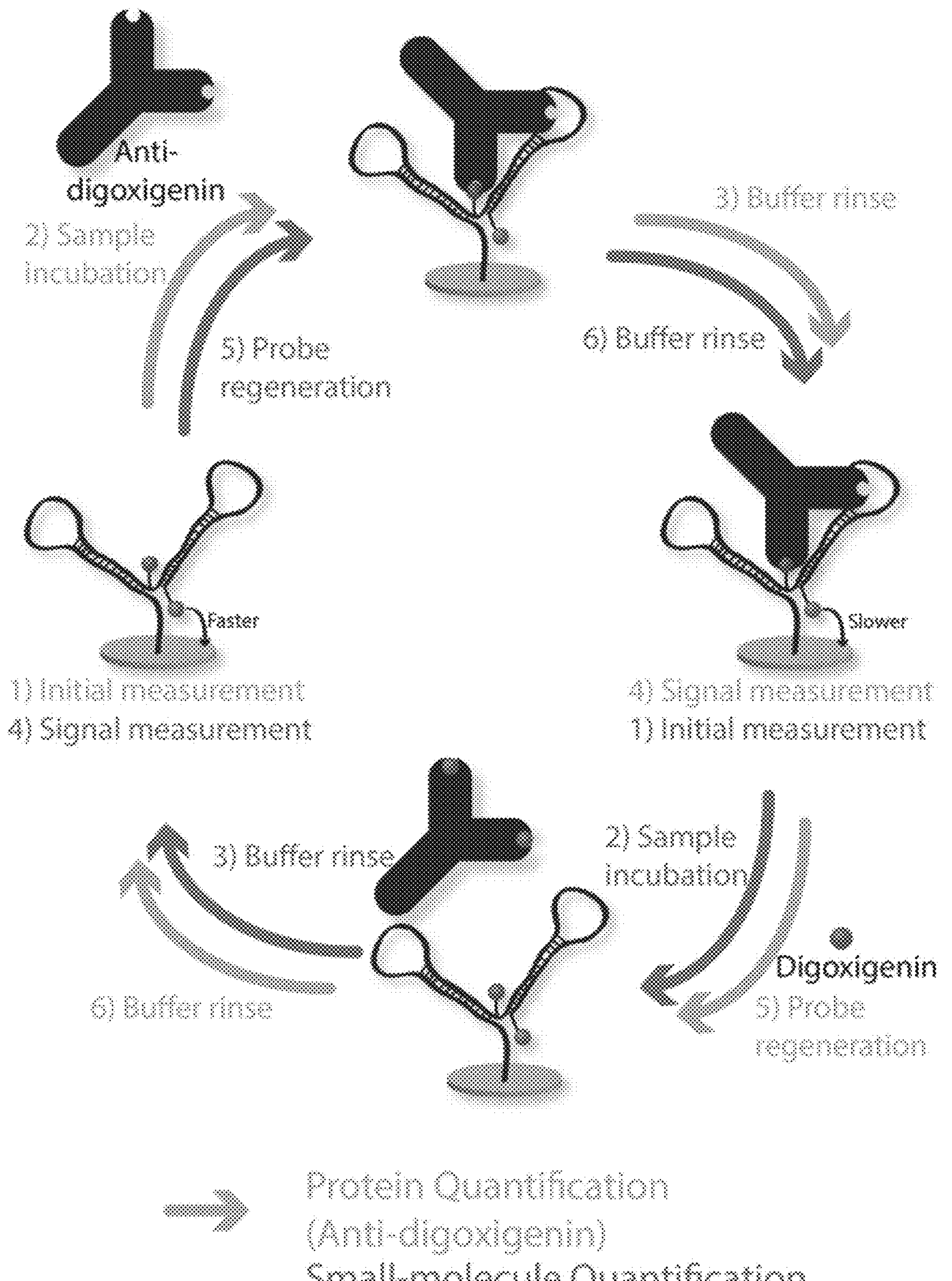

FIG. 16 can illustrate the basic steps in a DNA-nanostructure based assay using a direct (as exemplified by protein quantification) or indirect (as exemplified by small-molecule quantification) binding of an analyte of interest to the anchor recognition moiety.

Figure 17:
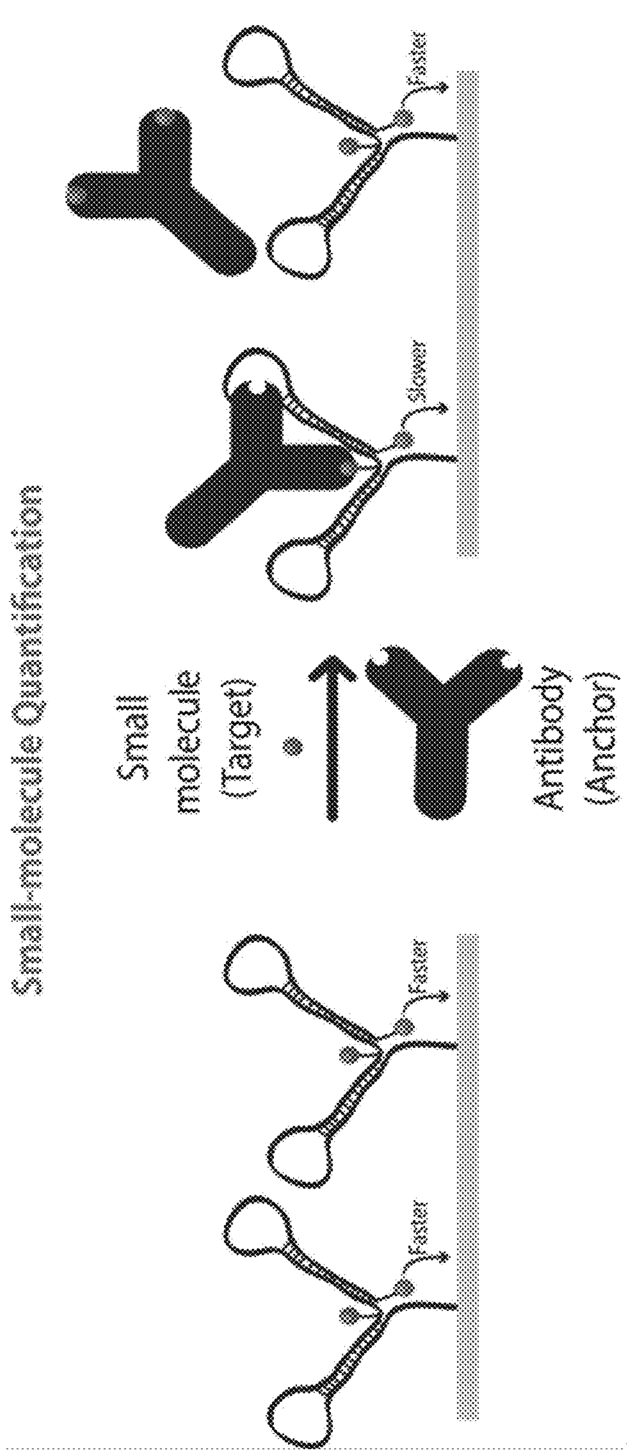

FIG. 17 can illustrate the principle of the DNA-nanostructure based assay using an indirect binding of an analyte of interest to the anchor (e.g. antibody), preventing the anchor from interacting with the anchor recognition moiety, as exemplified by small-molecule quantification. To promote higher sensitivity, the sample containing analyte is mixed with the anchor prior to adding this mixture to the surface.

Figures 18A, 18B, 18C:
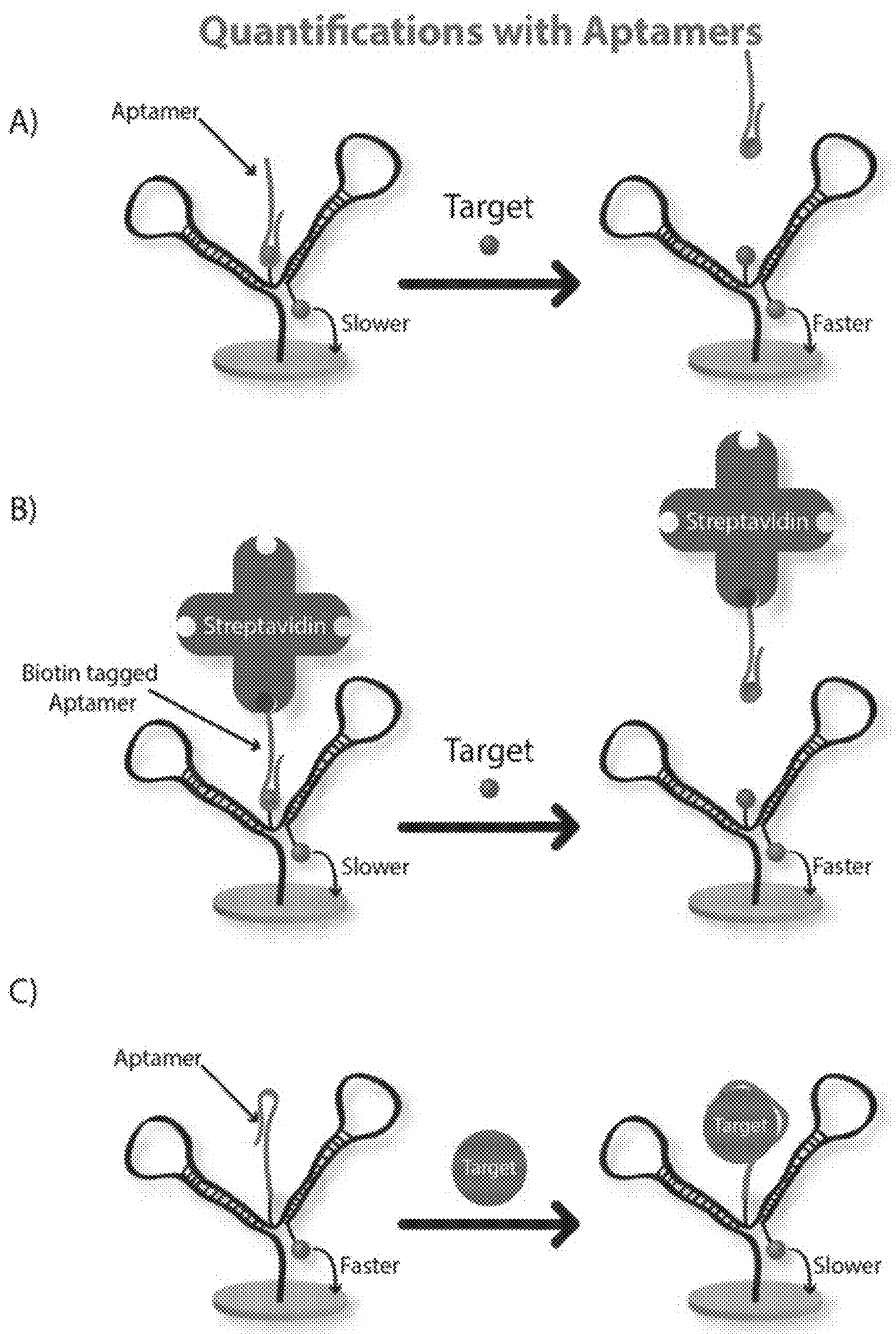

FIGS. 18A-18C can illustrate the principle of using nucleic acid aptamers in the framework of the nanostructure at an electrode surface. Aptamers can be used as the anchor as in FIG. 18A. While serving as anchor, aptamer-induced responses could be further enhanced by conjugation to a larger protein such as streptavidin as in FIG. 18B. Another example is shown in FIG. 18C, where the aptamer is conjugated to the nanostructure, in this case serving as the anchor recognition moiety.

Figures 19A, 19B:
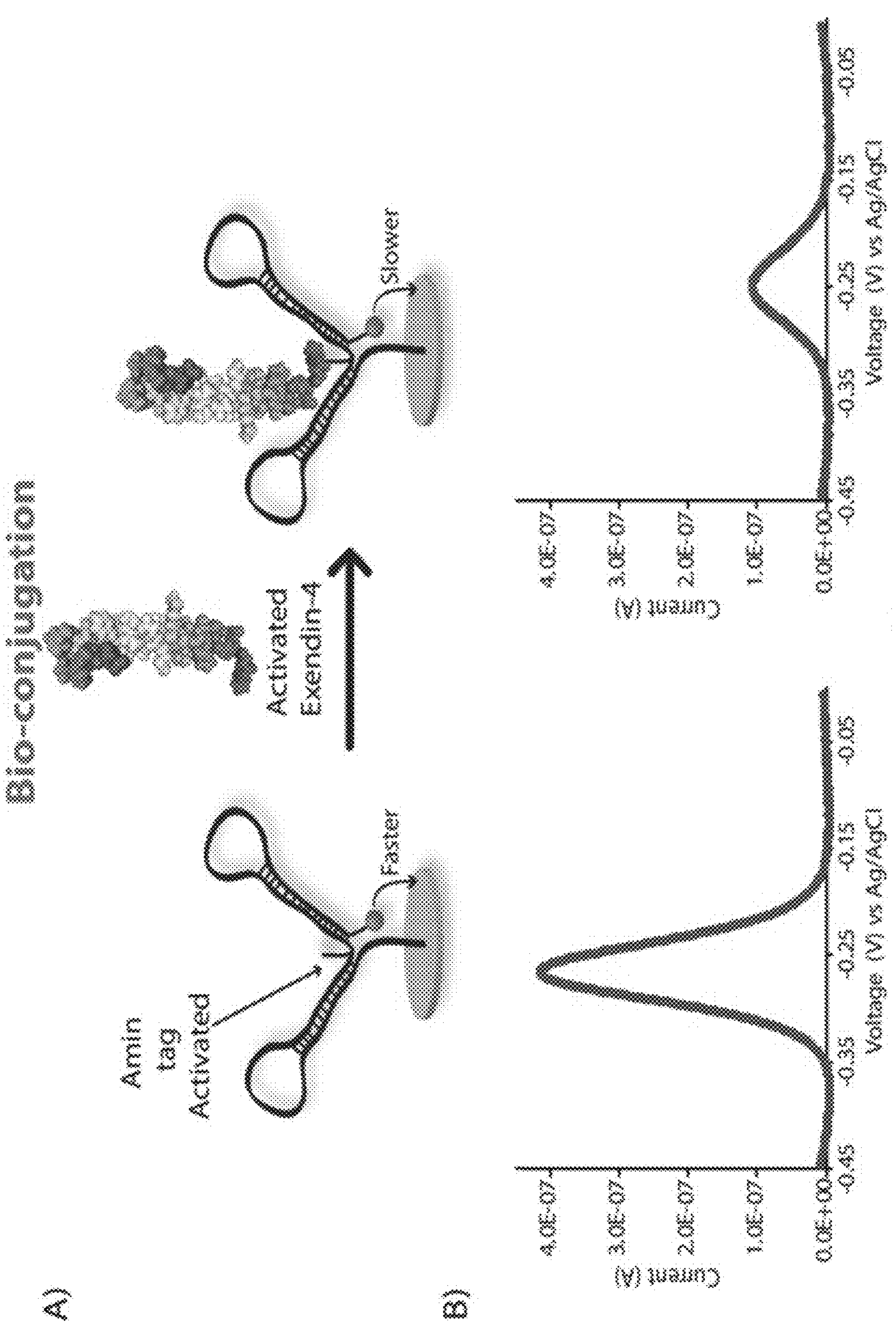
Figures 19C, 19D:
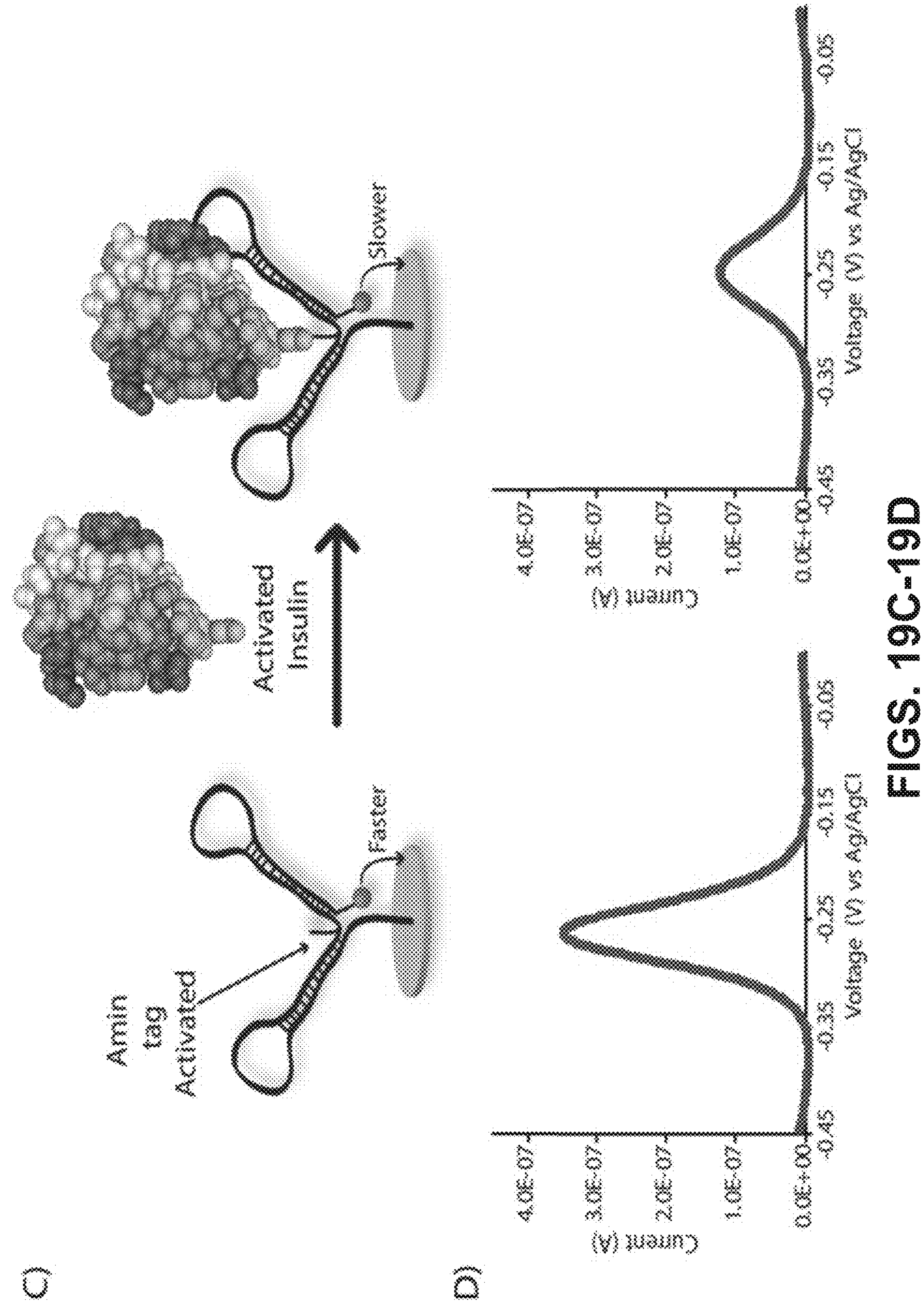

FIGS. 19A-19B can demonstrate using the nucleic acid nanostructure for monitoring of bioconjugation reactions. In one example, a peptide drug (exendin-4) was successfully activated and attached to the nanostructure as in FIG. 19A. This bioconjugation process could be monitored using square-wave voltammetry as in FIG. 19B, where the faradaic peak current was reduced due to the slowed tethered diffusion rate of the methylene blue label (signal moiety). A similar effect was observed when attaching a slightly larger, globular protein, insulin as shown in FIGS. 19C-19D.

Figures 20A, 20B:
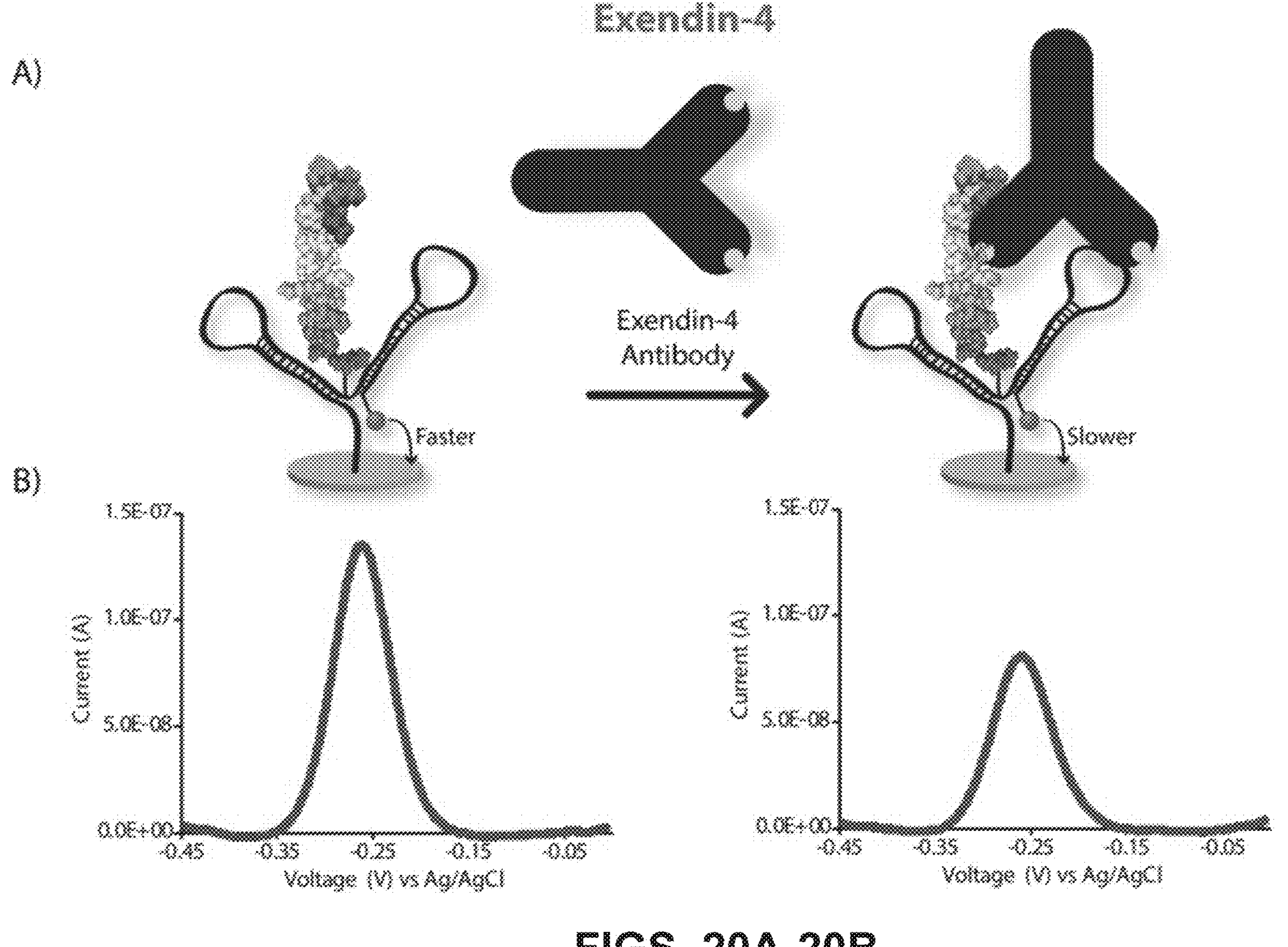
Figures 20C, 20D:
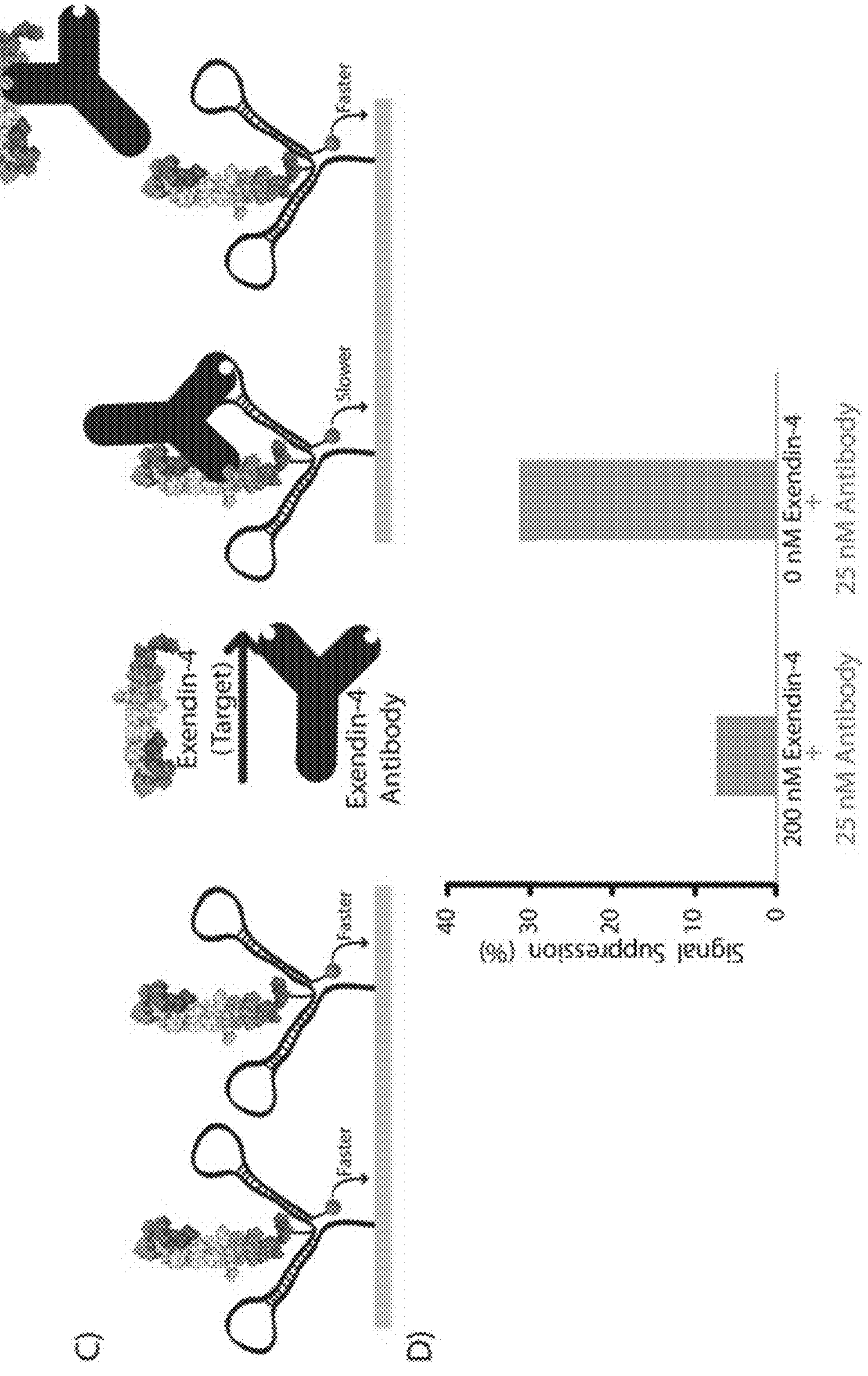

FIGS. 20A-20D can demonstrate the results of peptide antibody quantification (exendin-4 antibody) as in FIGS. 20A-20B. The same nanostructure can be used for indirect quantification of the same peptide in free solution (from the sample), as in FIGS. 20C-20D. Successful exendin-4 quantification results are shown in FIG. 20D.

Figure 21:
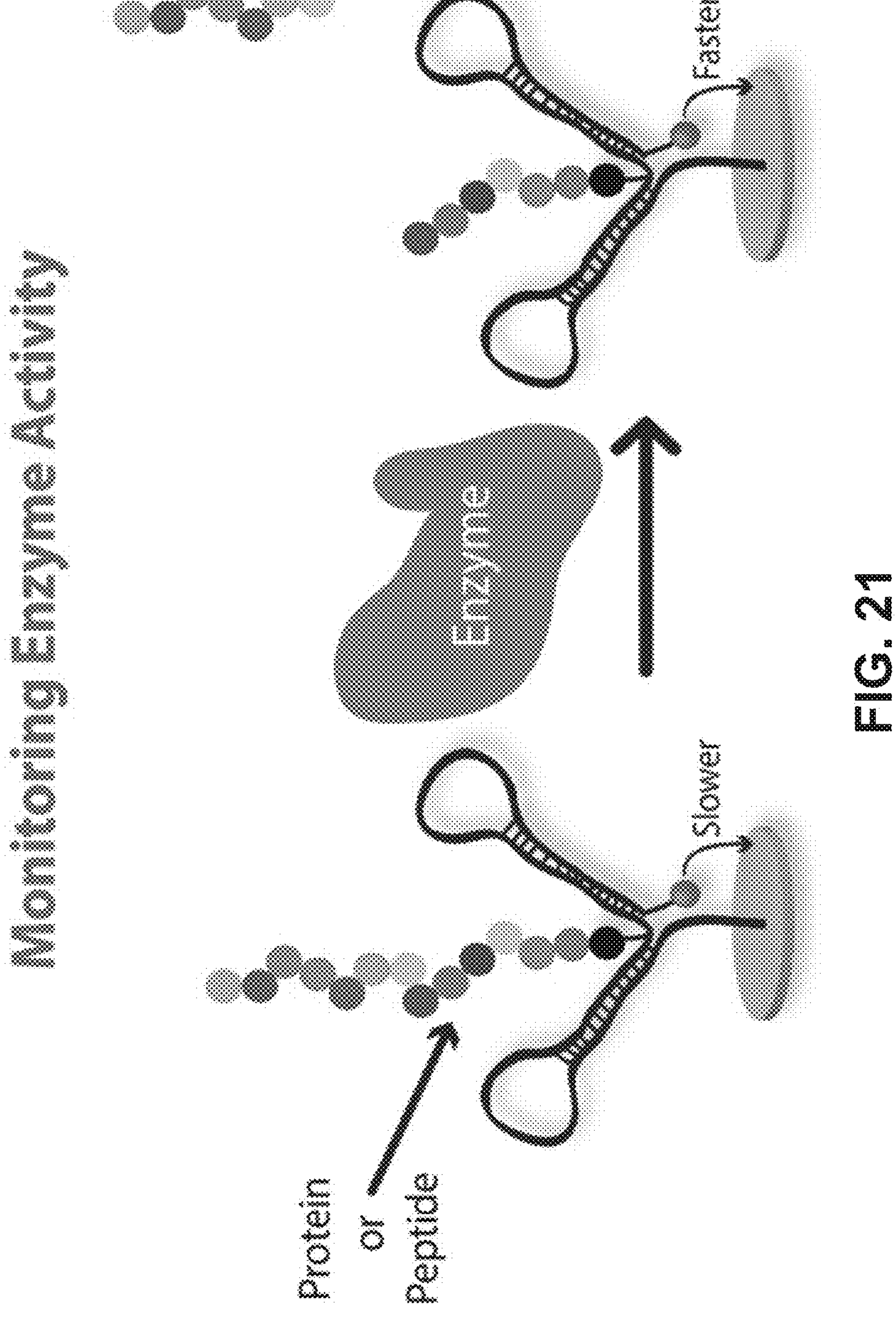

FIG. 21 can demonstrate using the nanostructure for enzyme activity monitoring. Cleavage of a peptide (or other biomolecule) attached to the nanostructure can be monitored during the reaction using the nanostructure's signal. This concept is feasible for either cleavage reactions or ligation (additive) reactions.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Where a range is expressed, a further aspect includes from the one particular value and/or to the other particular value. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used in the specification and the appended claims, the singular forms "a," "an," and "the" include plural referents unless the context clearly dictates otherwise.

As used herein, "about," "approximately," "substantially," and the like, when used in connection with a numerical variable, can generally refers to the value of the variable and to all values of the variable that are within the experimental error (e.g., within the 95% confidence interval for the mean) or within +/−10% of the indicated value, whichever is greater. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

Embodiments of the present disclosure will employ, unless otherwise indicated, techniques of molecular biology, organic chemistry, biochemistry, and the like, which are within the skill of the art. Such techniques are explained fully in the literature.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible unless the context clearly dictates otherwise.

Definitions

As used herein, "antibody" can refer to a glycoprotein containing at least two heavy (H) chains and two light (L) chains inter-connected by disulfide bonds, or an antigen binding portion thereof. Each heavy chain is comprised of a heavy chain variable region (abbreviated herein as VH) and a heavy chain constant region. Each light chain is comprised of a light chain variable region and a light chain constant region. The VH and VL regions retain the binding specificity to the antigen and can be further subdivided into regions of hypervariability, termed complementarity determining regions (CDR). The CDRs are interspersed with regions that are more conserved, termed framework regions (FR). Each VH and VL is composed of three CDRs and four framework regions, arranged from amino-terminus to carboxy-terminus in the following order: FR1, CDR1, FR2, CDR2, FR3, CDR3, and FR4. The variable regions of the heavy and light chains contain a binding domain that interacts with an antigen. "Antibody" includes single valent, bivalent and multivalent antibodies. "Antibody" also includes antibody fragments, such as Fab fragments. The term "Fab", as used herein, refers to antibody fragments including fragments which comprise two N-terminal portions of the heavy chain polypeptide joined by at least one disulfide bridge in the hinge region and two complete light chain polypeptides, where each light chain is complexed with one N-terminal portion of a heavy chain. Fab also includes Fab fragments which comprise all or a large portion of a light chain polypeptide (e.g., $V_LC_L$) complexed with the N-terminal portion of a heavy chain polypeptide (e.g., $V_HC_{H1}$).

As used herein, "aptamer" can refer to single-stranded DNA or RNA molecules that can bind to pre-selected targets including proteins with high affinity and specificity. Their specificity and characteristics are not only determined by their primary sequence, but also by their tertiary structure.

As used herein, "attached" can refer to covalent or non-covalent interaction between two or more molecules. Non-covalent interactions can include ionic bonds, electrostatic interactions, van der Walls forces, dipole-dipole interactions, dipole-induced-dipole interactions, London dispersion forces, hydrogen bonding, halogen bonding, electromagnetic interactions, π-π interactions, cation-π interactions, anion-π interactions, polar π-interactions, and hydrophobic effects.

The term "carboxyl" is as defined above for the formula

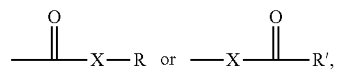

and is defined more specifically by the formula -RivCOOH, wherein Riv is an alkyl, alkenyl, alkynyl, cycloalkyl, heterocyclyl, alkylaryl, arylalkyl, aryl, or heteroaryl. In preferred embodiments, a straight chain or branched chain alkyl, alkenyl, and alkynyl have 30 or fewer carbon atoms in its backbone (e.g., C1-030 for straight chain alkyl, C3-C30 for branched chain alkyl, C2-C30 for straight chain alkenyl and alkynyl, C3-C30 for branched chain alkenyl and alkynyl), preferably 20 or fewer, more preferably 15 or fewer, most preferably 10 or fewer. Likewise, preferred cycloalkyls, heterocyclyls, aryls and heteroaryls have from 3-10 carbon atoms in their ring structure, and more preferably have 5, 6 or 7 carbons in the ring structure. The term "substituted carboxyl" refers to a carboxyl, as defined above, wherein one or more hydrogen atoms in R are substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

As used herein, "deoxyribonucleic acid (DNA)" and "ribonucleic acid (RNA)" can generally refer to any polyribonucleotide or polydeoxribonucleotide, which may be unmodified RNA or DNA or modified RNA or DNA. RNA can be in the form of non-coding RNA such as tRNA (transfer RNA), snRNA (small nuclear RNA), rRNA (ribosomal RNA), anti-sense RNA, RNAi (RNA interference construct), siRNA (short interfering RNA), microRNA (miRNA), or ribozymes, aptamers, guide RNA (gRNA) or coding mRNA (messenger RNA).

As used herein, "derivative" can refer to any compound having the same or a similar core structure to the compound but having at least one structural difference, including substituting, deleting, and/or adding one or more atoms or functional groups. The term "derivative" does not mean that the derivative is synthesized from the parent compound either as a starting material or intermediate, although this may be the case. The term "derivative" can include prodrugs, or metabolites of the parent compound. Derivatives include compounds in which free amino groups in the parent compound have been derivatized to form amine hydrochlorides, p-toluene sulfoamides, benzoxycarboamides, t-butyloxycarboamides, thiourethane-type derivatives, trifluoroacetylamides, chloroacetylamides, or formamides. Derivatives include compounds in which carboxyl groups in the parent compound have been derivatized to form methyl and ethyl esters, or other types of esters or hydrazides. Derivatives include compounds in which hydroxyl groups in the parent compound have been derivatized to form O-acyl or O-alkyl derivatives. Derivatives include compounds in which a hydrogen bond donating group in the parent compound is replaced with another hydrogen bond donating group such as OH, NH, or SH. Derivatives include replacing a hydrogen bond acceptor group in the parent compound with another hydrogen bond acceptor group such as esters, ethers, ketones, carbonates, tertiary amines, imine, thiones, sulfones, tertiary amides, and sulfides. "Derivatives" also includes extensions of the replacement of the cyclopentane ring with saturated or unsaturated cyclohexane or other more complex, e.g., nitrogen-containing rings, and extensions of these rings with side various groups.

As used herein, "DNA molecule" includes nucleic acids/polynucleotides that are made of DNA.

As used herein, "effective proximity" refers to the distance or range of distances that can exists between two or more molecules where an interaction or reaction between the two molecules occurs that generates a measurable response. In the context of this disclosure, the effective proximity of a signal moiety and an anchor recognition moiety is the distance or range of distances between the two moieties where binding of the anchor recognition moiety by an analyte of interest or an anchor molecule can modulate the tethered diffusion of the signal moiety such that a measurable change in a signal produced, directly or indirectly, by the signal moiety can be detected and/or quantified. In the context of this disclosure, the effective proximity of the signal molecule and a second molecule element with which it can chemically react or engage in resonant energy transfer, is the distance or range of distance between the signal molecule and the second molecule or element where the interaction can take place such that a measurable change in a signal produced, directly or indirectly, by the signal moiety can be detected and/or quantified.

As used herein, the terms "Fc portion," "Fc region," and the like are used interchangeably herein and refer to the fragment crystallizable region of an antibody that interacts with cell surface receptors called Fc receptors and some proteins of the complement system. The IgG Fc region is composed of two identical protein fragments that are derived from the second and third constant domains of the IgG antibody's two heavy chains.

As used herein, "identity," can refer to a relationship between two or more nucleotide or polypeptide sequences, as determined by comparing the sequences. In the art, "identity" can also refers to the degree of sequence relatedness between polynucleotide or polypeptide sequences as determined by the match between strings of such sequences. "Identity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J. Applied Math. 1988, 48:1073. Preferred methods to determine identity are designed to give the largest match between the sequences tested. Methods to determine identity are codified in publicly available computer programs. The percent identity between two sequences can be determined by using analysis software (e.g., Sequence Analysis Software Package of the Genetics Computer Group, Madison Wis.) that incorporates the Needelman and Wunsch, (J. Mol. Biol., 1970, 48:443-453,) algorithm (e.g., NBLAST, and XBLAST). The default parameters are used to determine the identity for the polypeptides or polynucleotides of the present disclosure, unless stated otherwise.

The term "molecular weight", as used herein, can generally refer to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight (Mw) as opposed to the number-average molecular weight (Mn). Capillary viscometry provides estimates of molecular weight as the inherent viscosity determined from a dilute polymer solution using a particular set of concentration, temperature, and solvent conditions.

As used herein, "nucleic acid," "nucleotide sequence," and "polynucleotide" can be used interchangeably herein and can generally refer to a string of at least two base-sugar-phosphate combinations and refers to, among others, singleand double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide as used herein can refer to triple-stranded regions comprising RNA or DNA or both RNA and DNA. The strands in such regions can be from the same molecule or from different molecules. The regions may include all of one or more of the molecules, but more typically involve only a region of some of the molecules. One of the molecules of a triple-helical region often is an oligonucleotide. “Polynucleotide” and “nucleic acids” also encompasses such chemically, enzymatically or metabolically modified forms of polynucleotides, as well as the chemical forms of DNA and RNA characteristic of viruses and cells, including simple and complex cells, inter alia. For instance, the term polynucleotide as used herein can include DNAs or RNAs as described herein that contain one or more modified bases. Thus, DNAs or RNAs including unusual bases, such as inosine, or modified bases, such as tritylated bases, to name just two examples, are polynucleotides as the term is used herein. “Polynucleotide”, “nucleotide sequences” and “nucleic acids” also includes PNAs (peptide nucleic acids), phosphorothioates, and other variants of the phosphate backbone of native nucleic acids. Natural nucleic acids have a phosphate backbone, artificial nucleic acids can contain other types of backbones, but contain the same bases. Thus, DNAs or RNAs with backbones modified for stability or for other reasons are “nucleic acids” or “polynucleotides” as that term is intended herein. As used herein, “nucleic acid sequence” and “oligonucleotide” also encompasses a nucleic acid and polynucleotide as defined elsewhere herein.

As used herein, the terms “optional” or “optionally” means that the subsequently described event or circumstance can or cannot occur, and that the description includes instances where said event or circumstance occurs and instances where it does not.

As used herein “peptide” can refer to chains of at least 2 amino acids that are short, relative to a protein or polypeptide.

As used herein, “polymer” refers to a chemical compound formed from a plurality of repeating structural units referred to as monomers “Polymers” are understood to include, but are not limited to, homopolymers, copolymers, such as for example, block, graft, random and alternating copolymers, terpolymers, etc. and blends and modifications thereof. Polymers can be formed by a polymerization reaction in which the plurality of structural units become covalently bonded together. When the monomer units forming the polymer all have the same chemical structure, the polymer is a homopolymer. When the polymer includes two or more monomer units having different chemical structures, the polymer is a copolymer.

As used herein, “polypeptides” or “proteins” refers to amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V). “Protein” and “Polypeptide” can refer to a molecule composed of one or more chains of amino acids in a specific order. The term protein is used interchangeable with “polypeptide.” The order is determined by the base sequence of nucleotides in the gene coding for the protein. Proteins can be required for the structure, function, and regulation of the body’s cells, tissues, and organs.

As used herein, the term “specific binding” can refer to non-covalent physical association of a first and a second moiety wherein the association between the first and second moieties is at least 2 times as strong, at least 5 times as strong as, at least 10 times as strong as, at least 50 times as strong as, at least 100 times as strong as, or stronger than the association of either moiety with most or all other moieties present in the environment in which binding occurs. Binding of two or more entities may be considered specific if the equilibrium dissociation constant, Kd, is $10^{-3}$ M or less, $10^{-4}$ M or less, $10^{-5}$ M or less, $10^{-6}$ M or less, $10^{-7}$ M or less, $10^{-8}$ M or less, $10^{-9}$ M or less, $10^{-10}$ M or less, $10^{-11}$ M or less, or $10^{-12}$ M or less under the conditions employed, e.g., under physiological conditions such as those inside a cell or consistent with cell survival. In some embodiments, specific binding can be accomplished by a plurality of weaker interactions (e.g., a plurality of individual interactions, wherein each individual interaction is characterized by a Kd of greater than $10^{-3}$ M). In some embodiments, specific binding, which can be referred to as “molecular recognition,” is a saturable binding interaction between two entities that is dependent on complementary orientation of functional groups on each entity. Examples of specific binding interactions include primer-polynucleotide interaction, aptamer-aptamer target interactions, antibody-antigen interactions, avidin-biotin interactions, ligand-receptor interactions, metal-chelate interactions, hybridization between complementary nucleic acids, etc.

As used herein, “surface,” in the context herein, refers to a boundary of a product. The surface can be an interior surface (e.g. the interior boundary of a hollow product), or an exterior or outer boundary or a product. Generally, the surface of a product corresponds to the idealized surface of a three dimensional solid that is topological homeomorphic with the product. The surface can be an exterior surface or an interior surface. An exterior surface forms the outermost layer of a product or device. An interior surface surrounds an inner cavity of a product or device, such as the inner cavity of a tube. As an example, both the outside surface of a tube and the inside surface of a tube are part of the surface of the tube. However, internal surfaces of the product that are not in topological communication with the exterior surface, such as a tube with closed ends, can be excluded as the surface of a product. In some embodiments, an exterior surface of the product is chemically modified, e.g., a surface that can contact a sample component or be coupled to a DNA-nanostructure described herein. In some embodiments, where the product is porous or has holes in its mean (idealized or surface), the internal faces of passages and holes are not considered part of the surface of the product if its opening on the mean surface of the product is less than 1 μm.

As used herein, “substantial” and “substantially,” specify an amount of between 95% and 100%, inclusive, between 96% and 100%, inclusive, between 97% and 100%, inclusive, between 98% 100%, inclusive, or between 99% 100%, inclusive.

As used interchangeably herein, “subject,” “individual,” or “patient” can refer to a vertebrate organism, such as a mammal (e.g. human). “Subject” can also refer to a cell, a population of cells, a tissue, an organ, or an organism, preferably to human and constituents thereof.

As used herein, “substantially free” can mean an object species is present at non-detectable or trace levels so as not to interfere with the properties of a composition or process.

As used herein, “substantially pure” can mean an object species is the predominant species present (i.e., on a molar basis it is more abundant than any other individual species in the composition), and preferably a substantially purified fraction is a composition wherein the object species comprises about 50 percent of all species present. Generally, a substantially pure composition will comprise more than about 80 percent of all species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single species.

As used herein, the term “tethered diffusion” refers to the local diffusion of a moiety that is tethered to a surface, where the moiety is limited from diffusion away from the surface but is diffusing within an approximate hemispherical region of three-dimensional space. In the context of this disclosure, changes in tethered diffusion rates were observed as changes in electrochemical current measured at a nanostructure-modified electrode when anchor molecules were either bound or unbound. Various other modes of measurement (optical, vibrational, etc.) could also be used to report tethered diffusion rates.

As used herein, the terms “weight percent,” “wt %,” and “wt. %,” which can be used interchangeably, indicate the percent by weight of a given component based on the total weight of a composition of which it is a component, unless otherwise specified. That is, unless otherwise specified, all wt % values are based on the total weight of the composition. It should be understood that the sum of wt % values for all components in a disclosed composition or formulation are equal to 100. Alternatively, if the wt % value is based on the total weight of a subset of components in a composition, it should be understood that the sum of wt % values the specified components in the disclosed composition or formulation are equal to 100.

DISCUSSION

The past decade has attracted renewed interest in developing electrochemical sensors for quantification of biomarkers, owing to their low cost and adaptability to point-of-care (POC) or point-of-use (POU) setups, which could significantly impact healthcare and other industries where analyte sensing is used. Relevant analyte targets for such quantification can be classified into small molecules, nucleic acids (e.g. mid-size molecules), and proteins (e.g. macromolecules). To quantify through this range of molecular classes, most method development has drifted towards being target-focused and has lacked generalizability. Currently, the toolbox for potential POC analysis is a conglomerate of methods or specially targeted probes. There is a pressing need to develop methods amenable to quantitative readout of multiple classes of clinically and other relevant targets.

Nucleic-acid based electrochemical methods predominantly exploit the structure switching of a probe for target-dependent signal change. These sensors are efficient for real-time measurements in a variety of sample types, including in the blood of living humans and animals. However, with structure-switching aptamer probes needed, many sensitive probes-antibodies or non-structure-switching aptamers—are insufficient, limiting generalizability. To further generalize, steric hindrance assays and E-DNA scaffold sensors have been developed and validated with antibody probes without conformation switching. However, non-covalent DNA hybridization demands solution equilibrium for probe construction, hindering the desired drop-and-read workflow. Most of these methods require DNA probes that are subjected to multiple conjugation steps, making probe preparation laborious and expensive.

With the limitations of current nucleic-acid based electrochemical sensors and systems in mind, described herein are aspects of a DNA-based electrochemical sensor that can include a DNA-nanostructure that can include a single DNA molecule that includes at least two hairpin structural motifs whose stems are coupled together via a region of unhybridized DNA, an anchor recognition moiety that is coupled to the unhybridized region of DNA that couples the at last two hairpin structural motifs together, a signal moiety that is coupled to a 3' terminal end of one of the hairpin motifs, and a tether region that is configured to be optionally attached to an electrode. When the anchor recognition moiety is unbound, the DNA-nanostructure moves in 3D space at a first frequency and/or speed defined by its tethered diffusion rate. Analyte binding is measured by detecting and/or measuring a change in the tethered diffusion rate as measured by analyzing the signal moiety. In short, when the anchor recognition moiety is bound, directly or indirectly, by an analyte, the DNA-nanostructure moves in 3D space at a second frequency and/or speed, defined by its new tethered diffusion rate. The first and second frequencies and/or speeds are different from each other. The frequency/speed can be detected by measuring properties of the signal moiety, directly or indirectly.

Also described herein are methods of making the DNA-nanostructures and systems thereof described herein. In some aspects, the DNA-nanostructure can be generated from ligating two or more DNA molecules together to form the single molecule DNA-nanostructure. Also described herein are aspects of a system that can include a DNA-nanostructure described herein and methods of using the DNA-nanostructure or systems thereof to at least detect an analyte of interest.

The DNA-nanostructures described herein can at least be versatile and capable of detecting a range of molecular classes of analytes, and capable of manufacture by a streamlined and economic process. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

DNA-Nanostructures and Systems Thereof

Described herein are aspects of a DNA-nanostructure and systems thereof that can be used in assays to detect and/or measure an analyte of interest. As shown FIGS. 1 and 2, the DNA-nanostructure 1000 can be composed of a single continuous DNA molecule that can have specialized structural regions (e.g. hairpin motifs 1001 *a,b*, stems 1005 *a,b*, anchor recognition moiety 1002, a signal moiety 1006, and a tether 1003) and can have an anchor recognition moiety 1002 and a signal moiety 1006 attached to the DNA-nanostructure 1000 in positions that place the anchor recognition moiety 1002 and the signal moiety 1006 in effective proximity to each other such that a change in the binding status of the anchor recognition moiety 1002 results in a change in the tethered diffusion of the signal moiety 1006, which can be measured and provide feedback on the binding status of the anchor recognition moiety 1002. In this way binding of an analyte of interest to the DNA-nanostructure 1000 can be detected and measured. It will be appreciated that each of the signal moiety 1006 and anchor recognition moiety 1002 can be coupled to the polynucleotide that can make up the DNA-nanostructure 1000 at any position so long as their positions relative to one another put them in effective proximity to each other as described elsewhere herein.

As generally discussed above, the DNA-nanostructure 1000 can include at least two hairpin structural motifs 1001 *a,b* (collectively 1001). The hairpin structural motifs 1001 each can be composed of a stem 1005 *a, b* (collectively 1005) and a loop 1004 (collectively 1004) region.

Figure 1:
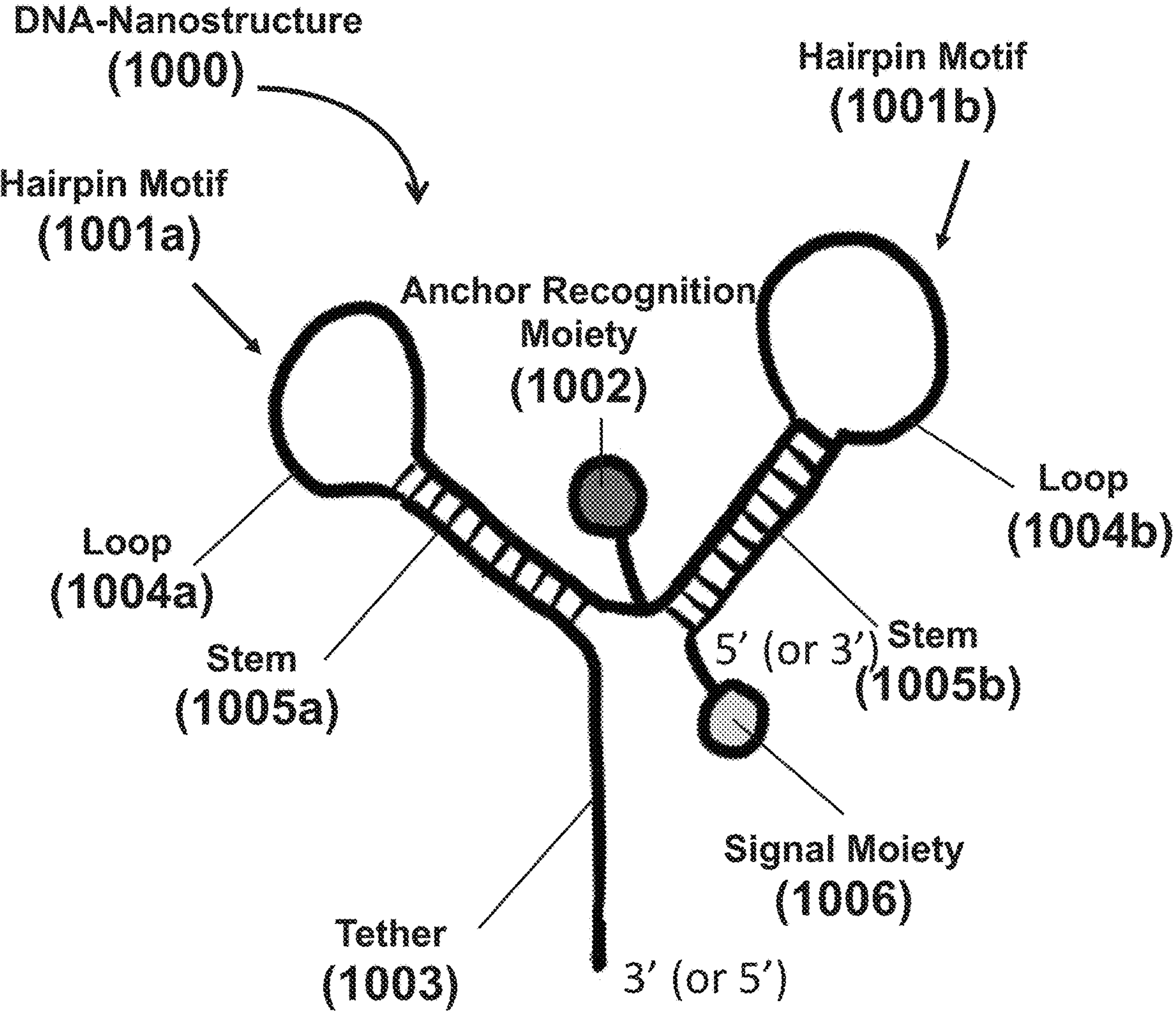
FIG. 1 shows various aspects of a DNA nanostructure sensor.

As shown in e.g. FIG. 1 the loop 1004 in each hairpin motif 1001 contains unpaired nucleotides. The loop 1004 in each hairpin motif 1001 can contain 1 to 100 nucleotides, with a preferred range of 4 to 20 nucleotides to promote efficient intramolecular hybridization, i.e. hairpin formation, during nanostructure construction or synthesis.

The loop 1004 in each hairpin motif 1001 can be composed of a wide range of nucleotide sequences. In aspects, the nucleotide sequence can limit or completely eliminate formation of a secondary structure within the loop and also can limit or completely eliminate interactions with any other portion of the nanostructure. A non-limiting example of such a nucleotide sequence can be is a poly-adenosine-monophosphate (polyA) sequence. In some aspects, additional nucleic acid elements can be attached or otherwise incorporated into the loop 1004 or other portion of the hairpin motif 1001. In a non-limiting example, the sequence of the loop 1004 *a* can be 5'- . . . CAA GAA CT . . . -3', and one example of the loop 1004 *b* is 5'- . . . ACT GTG TC . . . -3'. In some aspects, the loop 1004 in each hairpin motif 1001 can be comprised of a different polymer or biopolymer. One example would be to use a polyethylene glycol (PEG) chain instead of a nucleic acid loop in this region of the nanostructure.

The stem 1005 of each hairpin motif 1001 is composed of complementary DNA regions that are 90-100% complementary of each other and hybridized through conventional base-pair bonding. The stem 1005 of each hairpin motif 1001 can contain 2 to 100 nucleotides on each complementary DNA region, with a preferred range of 10 to 30 nucleotides to minimize the nanostructure's size while also promoting its assembly and ligation-based synthesis at the surface. In aspects the preferred Tm (melting temperature) of a stem 1005 *a* and/or 1005 *b* and/or hairpin motif can be between 15 to 60 degrees C. prior to ligation and/or hybridization. After ligation and/or hybridization, the complex becomes more stable with a Tm typically greater than 70 degrees C. In some aspects, the Tm of a of a stem 1005 *a* and/or 1005 *b* and/or hairpin motif can be about 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5, 35, 35.5, 36, 36.5, 37, 37.5, 38, 38.5, 39, 39.5, 40, 40.5, 41, 41.5, 42, 42.5, 43, 43.5, 44, 44.5, 45, 45.5, 46, 46.5, 47, 47.5, 48, 48.5, 49, 49.5, 50, 50.5, 51, 51.5, 52, 52.5, 53, 53.5, 54, 54.5, 55, 55.5, 56, 56.5, 57, 57.5, 58, 58.5, 59, 59.5, to/or about 60 degrees C. prior to ligation. In some aspects, the complex becomes more stable after ligation and/or hybridization and can have a Tm of about 70, 70.5, 71, 71.5, 72, 72.5, 73, 73.5, 74, 74.5, 75, 75.5, 76, 76.5, 77, 77.5, 78, 78.5, 79, 79.5, 80, 80.5, 81, 81.5, 82, 82.5, 83, 83.5, 84, 84.5, 85, 85.5, 86, 86.5, 87, 87.5, 88, 88.5, 89, 89.5, or/to about 90 degrees C.

The stem 1005 can be composed of a nucleotide sequence. In aspects, the stem 1005 nucleotide sequence can promote complementary hybridization (e.g. double-stranded DNA) in the stem region 1005 while also limiting or completely eliminating interactions with any other portion of the nanostructure. By way of a non-limiting example, in aspects the sequence of the stem 1005 *a* can be 5'- . . . CAC AGC CTC ACC TCT TCC TA . . . -3' (SEQ ID NO: 3) and its complementary sequence 5'- . . . TAG GAA GAG GTG AGG CTG TG . . . -3'; (SEQ ID NO: 4) and the stem 1005 *b* can be 5'- . . . TCT CCA CTT CAA CCG GAG AC . . . -3' (SEQ ID NO: 5) and it's complementary sequence 5'- . . . GTC TCC GGT TGA AGT GGA GA . . . -3' (SEQ ID NO: 6).

The DNA composing the hairpin motifs 1004 can include unmodified or modified nucleotides. Suitable base modifications include, but are not limited to 2-aminopurine, 2,6-diaminopurine, 5-bromo-deoxyuridine, deoxyuridine, inverted dT, inverted Dideoxy-T, Dideoxycytidine, 5-methyl deoxycytidine, deoxyinosine, 5-hydroxybutynl-2'-deoxyuridine, 8-aza-7-deazaguanosine, 5-nitroindole, hydroxymethyl dC, Iso-dC, Iso-dG, 2' fluoro bases, 2'-O-methoxyethyl Bases (2'MOEs). The specific DNA sequence of each hairpin motif can be readily generated by one of ordinary skill in the art based at least upon the parameters and functional aspects of at least the hairpin structural motifs and/or DNA-nanostructure discussed here and elsewhere herein. Commercially available DNA motif and hairpin design tools can be used to generate specific sequences that would form hairpin structures with the appropriate number of paired and unpaired nucleotides according to this disclosure. Such commercially available design tools can include EGNAS (Kick et al., BMC Bioinformatics. 2012. 13:138) or NUPACK (J. N. Zadeh, et al., J Comput Chem, 32:170-173, 2011.). In some aspects, the hairpin motifs have the same DNA sequence. In some aspects the hairpin motifs have a different DNA sequence than each other. In some aspects, the DNA sequence between any two hairpin motifs are completely different from one another. In some aspects, the hairpin motifs differ from each other in 1, 2, 3, 4, 5, 6, 7, 8, 9, 10, 11, 12, 13, 14, 15, 16, 17, 18, 19, 20, 21, 22, 23, 24, 25, or more nucleotides.

The two hairpin motifs can be coupled to each other directly (without unpaired nucleotides) or by an unhybridized (or unpaired) region of DNA (e.g. a region of single stranded DNA) between the stem region of one hairpin motif and the stem region of a second hairpin motif. This coupling region can include 0 to 100 nucleotides, or more nucleotides. A preferred coupling region would include 0 to 10 nucleotides to minimize the nanostructure size and maintain structural consistency. In aspects, the unhybridized region can be formed from a 3' tail of one hairpin motif and a 5' tail of a second hairpin motif that are ligated together during formation of the DNA-nanostructure. It will be appreciated that where the structure is described with respect to the 5' and 3' ends or direction, that the is also the same. In short, as long as the secondary structure can be attained, the read direction of the underlying nucleotide sequences can be either direction. This is demonstrated as such in FIG. 1, which denotes that the ends of the DNA nanostructure can be either 5' or 3' based on the chemical structure of the polynucleotide.

The 3' (or 5', when the reverse polynucleotide is considered) end of a stem 1005 *a* of one of the DNA structural motifs 1001 *a* can be coupled to a tether 1003. The tether 1003 can be a DNA strand that can be configured to optionally couple to a support structure or electrode surface 1007. The length of the tether 1003 can, in aspects where the tether 1003 is coupled to a support or electrode surface 1007, keep the anchor recognition portion at a distance from the support or electrode surface 1007 such that the signal moiety 1006 is at a suitable distance from the support or electrode surface 1007. The tether 1003 can include a linkage from the surface to the double-stranded stem region 1005*a*, such as a polymer chain or carbon chain. The tether 1003 can also include unhybridized single stranded DNA. If so, the tether 1003 can include 0, 1, 2, 3, 4, 5, 6, 7, 8, 9, 10, 11, 12, 13, 14, 15, 16, 17, 18, 19, or 20 nucleotides. Each of the nucleotides in the tether can be unmodified or modified bases. Suitable base modifications include, but are not limited to 2-aminopurine, 2,6-diaminopurine, 5-bromo-deoxyuridine, deoxyuridine, inverted dT, inverted Dideoxy-T, Dideoxycytidine, 5-methyl deoxycytidine, deoxyinosine, 5-hydroxybutynl-2'-deoxyuridine, 8-aza-7-deazaguanosine, 5-nitroindole, hydroxymethyl dC, Iso-dC, Iso-dG, 2' fluoro bases, 2'-O-methoxy-ethyl Bases (2'MOEs).

The 3' (or 5', when considering the reverse polynucleotide) end of the tether can be optionally modified or coupled to a linking moiety that renders the tether capable of coupling to a support or electrode surface. Suitable linking moieties linking moieties can include, or include after a suitable reaction, a suitable reactive group. Many suitable reactive groups are generally known to those of ordinary skill in the art. Suitable reactive groups include, but are not limited to, a carboxyl group, amino group, aromatic amine group, a chloromethyl group, an amide group, a hydrazide group, a hydroxyl, a thiol, an epoxy or a combination thereof. These groups can be incorporated to the tether 1003 using a reaction that will be instantly appreciated by one of ordinary skill in the art. The tether 1003 can be attached to a support or electrode surface 1007 using a suitable reaction that will be instantly appreciated by one of ordinary skill in the art based, at least in part, on the reactive group used and the chemical nature of the support or electrode surface 1007.

Figure 2:
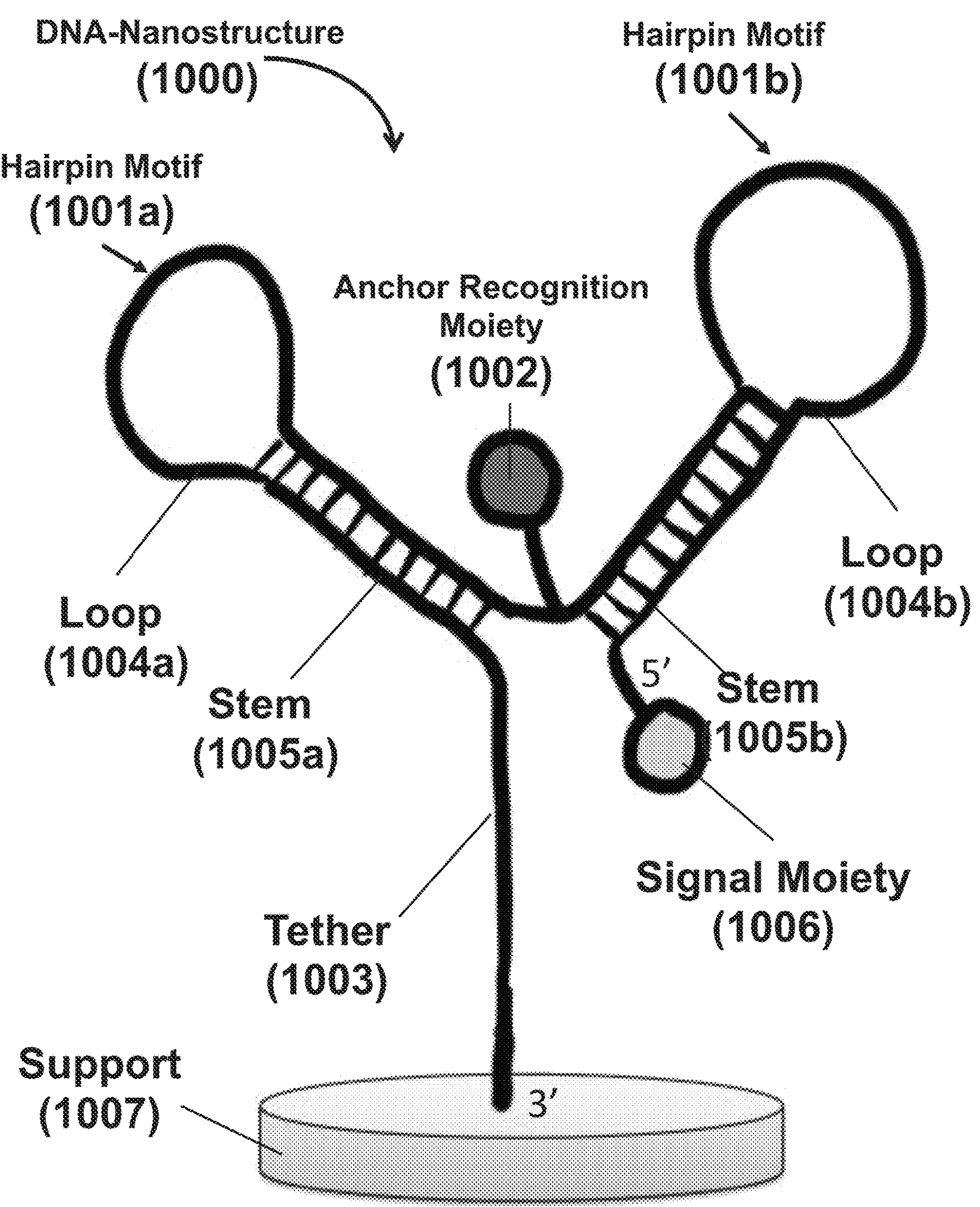
FIG. 2 shows various aspects of a DNA nanostructure sensor attached to an electrode support.

The nucleic acid nanostructure can have any polynucleotide sequence that results in the formation of the general secondary structures depicted in FIG. 1 and FIG. 2. Specifically, a tether 1003 can be unattached or can be attached to a surface. The tether 1003 is linked to a stem 1005 *a* with a loop 1004 *a*. A second stem 1005 *b* and loop 1004 *b* are used to provide structural consistency and to aid in nanostructure assembly and synthesis. The anchor recognition moiety 1002 should be positioned near the signal moiety 1006. The positioning of these moieties (1002 and 1006) relative to the nanostructure (1000) is not necessarily fixed, although a convenient positioning is to place them in between the two stems 1005 *a* and 1005 *b*.

In some aspects, the DNA-nanostructure can have a polynucleotide sequence prior to optional base modification that is about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% to 100% identical to any one of SEQ ID NOs: 7-8. It will be appreciated that any primary polynucleotide sequence is acceptable such that it can generate the secondary structure as described elsewhere herein. In some aspects, the DNA-nanostructure can have a polynucleotide sequence prior to any optional base modification that does not share any identity with SEQ ID NOs: 7-8, as long as the primary polynucleotide sequence is acceptable such that it can generate the secondary structure as described elsewhere herein. Suitable primary polynucleotide sequences corresponding to the secondary structures described and demonstrated herein can be designed and analyzed using the NUPACK software suite, which can allow the analysis and rational design of nucleic acid structures based on the equilibrium base-pairing properties of interacting nucleic acid strands. The NUPACK software suite is available at nupack.org and is further discussed in Zadeh et al., NUPACK: analysis and design of nucleic acid systems. J Comput Chem, 32:170-173, 2011, Dirks et al., Thermodynamic analysis of interacting nucleic acid strands. SIAM Rev, 49:65-88, 2007; Dirks and Pierce, An algorithm for computing nucleic acid base-pairing probabilities including pseudoknots. J Comput Chem, 25:1295-1304, 2004; Dirks and Pierce, A partition function algorithm for nucleic acid secondary structure including pseudoknots. J Comput Chem, 24:1664-1677, 2003; Wolfe et al., Constrained multistate sequence design for nucleic acid reaction pathway engineering. J Am Chem Soc, 139:3134-3144, 2017; Wolf and Pierce, Sequence design for a test tube of interacting nucleic acid strands. ACS Synth Biol, 4:1086-1100, 2015; Zadeh et al., Nucleic acid sequence design via efficient ensemble defect optimization. J Comput Chem, 32:439-452, 2011; and Dirks et al., Paradigms for computational nucleic acid design. Nucl Acids Res, 32:1392-1403, 2004. By way of example, the code that can be input into NUPACK for the design of the DNA nanostructure is given below:

Target Structure (code between quotes was added into NUPACK Design feature):

```
"material=dna
temperature=25
trials=3
dangles=some
sodium=0.5
structure MBDNA=U15
structure ThiolDNA=U33
structure AnchorDNA=U48
domain a=N5
domain b=N8
domain c=N15
domain d=N5
domain e=N8
domain f=N15
MBDNA.seq=f*
ThiolDNA.seq=a b a*c
AnchorDNA.seq=d e d*f c*
prevent=AAA, GGG, CCC"
```

Other codes will be appreciated in view of the disclosure herein by one of ordinary skill in the art to generate suitable polynucleotide sequences that are appropriate for use with the DNA nanostructure described and provided herein.

Example Results from Exemplary NUPACK Design Code:

Note that the sequence for Tether 1003 (FIGS. 1-2) was manually added following the NUPACK design; the Tether 1003 sequence is preferably a linear strand such as polyA (e.g. 5'- . . . AAAA-3'), but it is not necessarily limited to this sequence constraint. One example of NUPACK design results is already given in Table 3, which are the sequences used in the examples given herein (SEQ ID NO: 13, SEQ ID NO: 14, and SEQ ID NO: 16). Additional Examples of NUPACK's output sequence designs based on the above constraints are given below. Of course, variations in these sequences are possible.

NUPACK Design Output #1 (5' to 3'):

```
                                          (SEQ ID NO: 24)
structure MBDNA =
TGA GGT GTG GAG GTA

                                          (SEQ ID NO: 25)
*structure ThiolDNA =
TAT ATG TTG GAT GAT ATA AGG AGG AAG GTG

GTG

                                          (SEQ ID NO: 26)
structure AnchorDNA =
TTA ATG GCC TAA GAT TAA TAC CTC CAC ACC

TCA CAC CAC CTT CCT CCT
```

NUPACK Design Output #2 (5' to 3'):

```
                                          (SEQ ID NO: 27)
structure MBDNA =
AAG AAG AAG AGA AGG

                                          (SEQ ID NO: 28)
*structure ThiolDNA =
TTA ATT CAC CAC TAT TAA GAC AAG ATA AGC

GCG

                                          (SEQ ID NO: 29)
structure AnchorDNA =
TAT ATC ACC ACT TAT ATA CCT TCT CTT CTT

CTT CGC GCT TAT CTT GTC
```

NUPACK Design Output #3 (5' to 3'):

```
                                          (SEQ ID NO: 30)
structure MBDNA =
TTC ACA CTT CAC TTC

                                           (SEQ ID NO: 1)
*structure ThiolDNA =
ATA TAG GTT ACG GTA TAT TCA TTC ATT CTC

TCC

                                           (SEQ ID NO: 2)
structure AnchorDNA =
TTA CTG ACA ACA GAG TAA GAA GTG AAG TGT

GAA GGA GAG AAT GAA TGA
```

Note that Tether 1003 should be added to these sequences.

The DNA-nanostructure 1001 can be configured to bind directly to analyte of interest or indirectly (i.e. through an anchor molecule that can directly bind the analyte of interest). To accomplish this, the anchor recognition moiety 1002 can be configured to specifically bind the analyte of interest or bind an anchor molecule. Analytes of interest can include small molecule chemical (organic or inorganic) compounds, drugs, DNA molecules, RNA molecules, peptides, and proteins. The analyte of interest can be determined by a user of the DNA nanostructure and can serve as the basis for directing a user or one of ordinary skill in the art to determine the appropriate components of the DNA-nanostructure and system thereof described herein in view of this disclosure using techniques generally known in the art. Similarly, anchor recognition moiety 1002 molecules of interest can include small molecule chemical (organic or inorganic) compounds, drugs, DNA molecules, RNA molecules, peptides, and proteins. The anchor recognition moiety 1002 of interest can be determined by a user of the DNA nanostructure and can serve as the basis for directing a user or one of ordinary skill in the art to determine the appropriate components of the DNA-nanostructure and system thereof described herein in view of this disclosure using techniques generally known in the art.

Without the description of the DNA-nanostructure, systems thereof, methods of manufacture, and assays herein, one of ordinary skill in the art with the analyte of interest in mind would not arrive independently at the DNA-nanostructure, systems thereof, methods of manufacture, and assays herein.

Exemplary analytes of interest will therefore be the same or similar to exemplary anchor recognition moieties 1002; these include, but are not limited to, small molecule drugs such as tamoxifen, atorvastatin, apremilast, morphine, etc.; peptide drugs such as exendin-4, NA-1, insulin analogs, etc.; larger protein or antibody therapeutics such as insulin, pembrolizumab, rituximab, etc.; biomarkers such as cortisol, neuropeptide-Y, IFN-gamma, C-peptide, glucagon, somatostatin, C-reactive protein, natriuretic peptides, creatine kinase, procalcitonin, etc.; immune markers such as tissue transglutaminase antibodies, anti-nuclear antibodies, etc.; toxins such as ricin, alpha-amanitin, etc.; biotechnology reagents such as biotin, streptavidin, digoxigenin, etc. Due to the generalizability of the nanostructure, there is a very wide range of analytes and anchor recognition moieties 1002 that are potentially of interest.

Anchor molecules are molecules that can either be the analyte of interest (as part of the sample), or be a binding partner of the analyte of interest, or be an analog that is similar to the analyte of interest. Anchor molecules should specifically bind to the anchor recognition moiety on the DNA-nanostructure. In a similar way, the anchor recognition moiety can either have the same or similar structure as the analyte of interest, or be a binding partner of the analyte of interest, or be an analog that is similar to the analyte of interest. The use of an anchor molecule can allow for, among other things that will be appreciated by one of ordinary skill in the art in view of this disclosure, configuration of the assay as a "signal OFF" (i.e., where the assay begins with the anchor molecule not bound to the anchor recognition moiety and binding turns the signal "off") or as a "signal ON" (i.e. where the assay begins with the anchor molecule bound to the anchor recognition moiety and binding of an analyte of interest results in the anchor molecule disassociating with the anchor recognition moiety and turns the signal "on") assay. Suitable anchor molecules include antibodies, aptamers, affibodies, proteins, peptides, nucleic acids, polymers, particles, beads, cells, and fragments thereof, that can specifically bind an analyte of interest and the anchor recognition moiety.

Exemplary anchor molecules include, but are not limited to, streptavidin, anti-digoxigenin, anti-insulin, anti-exendin-4, anti-C-peptide, tissue transglutaminase antibodies, anti-nuclear antibodies, insulin, pembrolizumab, rituximab, IFN-gamma, ricin, anti-thrombin aptamers, anti-ATP aptamers, anti-cocaine aptamers, miRNA-375, mannose-binding lectins, gold nanoparticles, cancer cells, bacterial pathogens, viral particles, etc. Due to the generalizability of the nanostructure, there is a very wide range of anchor molecules that are potentially of interest. The DNA-nanostructure 1000 can include a signal moiety 1006. The signal moiety 1006 can be capable of producing a signal (e.g. by generating an optical signal) or causing a signal to be produced (e.g. via a redox reaction or resonance-based reaction (e.g. FRET) at an electrode surface or support surface). The tethered diffusion can be measured via measuring the signal produced from the signal moiety directly. In aspects where the DNA-nanostructure 1000 is not tethered (e.g. is free in a solution), the rate at which the signal moiety 1006 moves or its change in position over time can be directly measured by monitoring a signal (e.g. an optical signal) produced from the signal moiety 1006. For example, a fluorescent molecule can be used as the signal moiety 1006, and the fluorescence lifetime of this molecule can be monitored in real time. The fluorescence lifetime will undergo a shift upon anchor binding to the analyte recognition moiety 1002. Fluorescence lifetime measurements generally require time-resolved instrumentation (e.g. with picosecond pulsed lasers and high speed detectors). In another example a fluorescent molecule can be used as the signal moiety 1006, and the fluorescence anisotropy of this molecule can be monitored in real time. The fluorescence anisotropy will undergo a shift upon anchor binding to the analyte recognition moiety 1002. Fluorescence anisotropy measurements usually require polarized optical filters and multiple optical detectors.

In aspects, a signal produced from the signaling moiety 1006 can be directly measured if the signal moiety is attached to a support or an electrode surface. In these aspects, the signal moiety can be configured to produce an optical signal when it is in proximity to the support or electrode surface such that a resonance-based reaction can occur and result in signal production (e.g. direct fluorescence, total internal reflection fluorescence (TIRF), surface-enhanced fluorescence, etc.) from the signaling moiety 1006. Changes in the frequency or position of interaction of the signaling moiety 1006 with the support or electrode surface 1007 (e.g. due to the anchor recognition moiety being bound or not) can result in a change in the output signal from the signaling moiety and can be used to detect and/or quantify presence of an analyte.

The tethered diffusion can also be quantified by measuring an output from an electrode, where the electrode is stimulated to produce and/or modulate an output when a signal moiety interacts with an electrode surface 1007. The interaction at the electrode surface 1007 can be a chemical (e.g. a redox) reaction that can occur when the signaling moiety is in proximity to the electrode surface such that a reaction can occur. Changes in the frequency or position of interaction of the signaling moiety with the electrode surface (e.g. due to the anchor recognition moiety being bound or not) can result in a change in the output signal from the electrode, which can be used to detect and/or quantify presence of an analyte.

Suitable signaling moieties include redox molecules and optically active molecules. Suitable redox molecules include, but are not limited to methylene blue, nile blue, anthraquinone, ferrocene, ferricyanide/ferrocyanide, etc. Suitable optically active molecules include, but are not limited to, any light emitting (fluorescent, infrared, ultraviolet, etc.) small molecule compound include chemical compounds and quantum dots. Fluorescent small molecule compounds are commercially available and generally known in the art and include, but are not limited to, fluorescein, carboxyfluorescein (FAM), rhodamine, carboxy-X-rhodamine (ROX) coumarin, cyanine, Oregon green, eosin, Texas Red, indocarbocyanine, oxacarbocyanine, thiacarbocyanine, merocyanine, squaraine and derivatives thereof, squaraine rotaxane and derivatives thereof, naphthalene, TAMRA, VIC, TET, Cy3, Cy5, TyE 563, Yakima Yellow, HEX, TEX 615, TYE 665, TYE 705, AlexaFlour compounds (e.g. Alexa Flour 488, 532, 546, 594, 647, 660, 750) LI-Cor IRdyes (e.g. 5' IREDye 700 or 800), ATTO Dyes (e.g. ATTO 488, 532, 550, 565, Rho101, 590, 633, 647), SeTau lifetime and polarization labels (e.g. SeTau-380, 405, 425, 647, 665, 670, 680), and WelIRED dyes (WelIRED D4 Dye, WelIRED D3 Dye, WelIRED D2 Dye). Other suitable optically active molecules will be appreciated by one of ordinary skill in the art in view of this description herein.

In aspects, the DNA-nanostructure can be attached to a support structure or an electrode surface. The support structure or electrode can be any suitable shape or design. In aspects, the electrode is a support structure. The DNA-nanostructure can be attached to the support structure or an electrode surface via the tether. As previously discussed, the tether can have a 3' linker or modified nucleotide(s) that can provide a reactive group that can be used to attach the tether to the support structure or an electrode surface.

Suitable support structures can be any solid or semi-solid (e.g. hydrogel) material. Suitable materials include glass, ceramics, metals, metal oxides, metal alloys, polymeric materials (polymers, copolymers, composite polymers, polymer blends, etc.), mixtures thereof and composites thereof. Metals can include, but are not limited to, the alkali metals, alkaline earth metals, transition metals, rare earth metals, combinations thereof, mixtures thereof, and composites thereof. In aspects, the metal or metal composite, oxide, alloy, or mixture thereof can be or include gold, aluminum, copper, iron, lead, silver, platinum, zinc, and/or nickel. Suitable polymeric materials can include, but are not limited to, natural and synthetic polymeric materials. Natural polymeric materials can include, but are not limited to, polysaccharides, natural rubber, polylacticacid, polylysine, polyglutamate, polyornithine, polyarginine, polyaspartate, polyhistidine, polylactide, etc. Synthetic polymers include, but are not limited to, polyethylene, polypropolyene, polystyrene, polyvinyl chloride, synthetic rubber, phenol formaldehyde resin, silicone, polyacrylonitrile, polystyrene, polytetrafluoroethylene, polyurethanes, polyethylene terephthalate, and combinations, copolymers, and blends thereof. The polymeric material can be a thermoplastic, thermoset, elastomer, or a permissible combination thereof.

The electrode and/or electrode surface can be made of any suitable material. In aspects, the suitable material is electrically conductive. In some aspects, electrode and/or electrode surface can be made of a metal, metal oxide, metal composite, metal alloy, or a combination thereof. Metals can include, but are not limited to, the alkali metals, alkaline earth metals, transition metals, rare earth metals, combinations thereof, mixtures thereof, and composites thereof. In aspects, the metal or metal composite, oxide, alloy, or mixture thereof can be or include gold, aluminum, copper, iron, lead, silver, platinum, zinc, and/or nickel.

Methods of Making the DNA-Nanostructure and Systems Thereof.

Conventional electrochemical sensors are expensive and time consuming to manufacture as previously discussed. Described herein are aspects of a method of manufacturing DNA-based nanostructures that can be used in an electrochemical or other assay, including those described herein. With that in mind, attention is directed to e.g. FIGS. 8A-8B, which shows various aspects of a method of generating a DNA-nanostructure described herein. Generation of the DNA-based nanostructure can begin by separately generating three separate components that can be brought together to form the single molecule DNA-nanostructure.

Figures 8A, 8B:
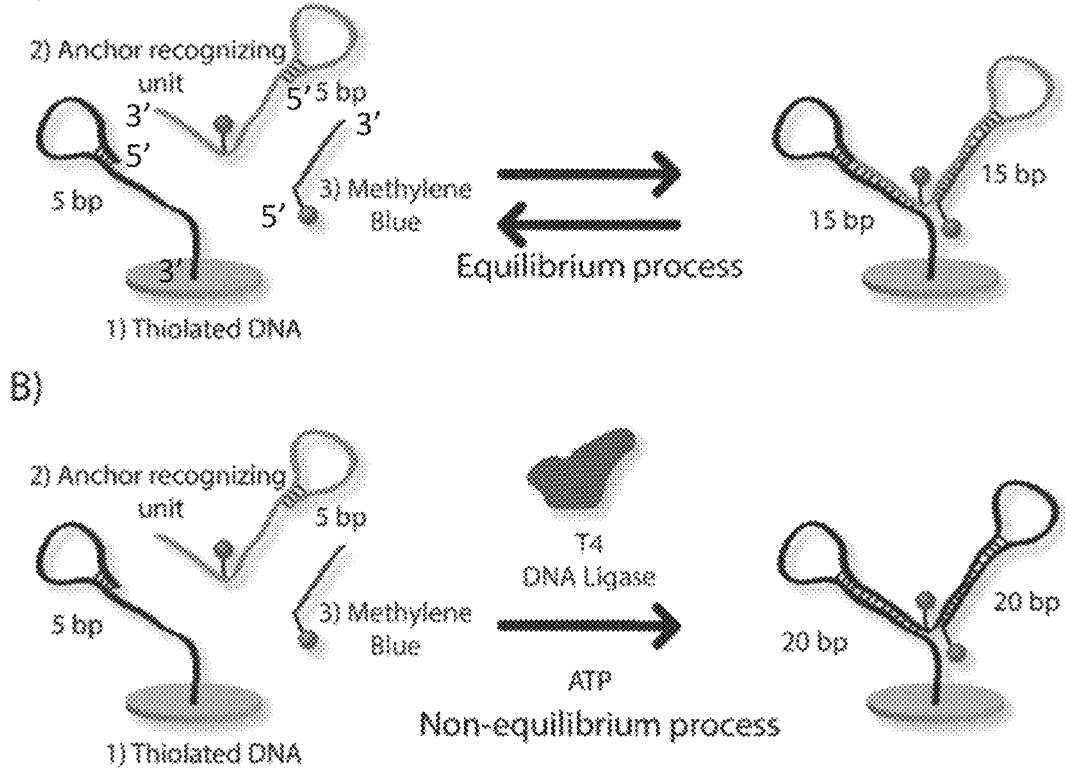
FIGS. 8A-8B show (FIG. 8A) Hybridization of thio-DNA, anchor-DNA, and MB-DNA forms the DNA nanostructure, but it is an equilibrium process.

A first partial hairpin DNA (1) in e.g. FIGS. 8A-8B with about 1-50, with a preferred range of 3-15, bases hybridized in the stem region can be generated by any suitable DNA synthesis technology (e.g. any recombinant or de novo synthesis technique), which will be appreciated by one of ordinary skill in the art in view of this disclosure. Appropriate DNA sequences for the first partial hairpin DNA can be determined by one of ordinary skill in the art based upon the direction provided elsewhere herein. The 3' (or 5' end when considering the reverse) end can be optionally modified with a suitable linker or contain one or more modified nucleotides, where the linker or modification provides a reactive group to allow for optional attachment to a support structure or electrode surface. Suitable linkers/modifications are described elsewhere herein. Methods of incorporating those linkers/modification into DNA will be appreciated by one of ordinary skill in the art in view of this disclosure. In aspects where the DNA-nanostructure is optionally coupled to a support or electrode surface, the first partial hairpin DNA can be coupled to the support or electrode surface prior to further assembly of the DNA-nanostructure. In aspects, the first partial hairpin can have a sequence prior to optional 3' (or 5' when considering the reverse) terminal base modification that is about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% to 100% identical to SEQ ID NO: 9. In aspects, the first partial hairpin can have a sequence prior to base modification that is about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical to SEQ ID NO: 9. It will be appreciated that any primary polynucleotide sequence is acceptable such that it can be assembled with other DNA-nanostructure components described elsewhere herein and generate the secondary structure as described elsewhere herein. In some aspects, the first partial hairpin can have a polynucleotide sequence prior to any optional base modification that does not share any identity with SEQ ID NO.: 9, as long as the primary polynucleotide sequence is acceptable such that it can be assembled with other DNA-nanostructure components described elsewhere herein and generate the secondary structure as described elsewhere herein.

A second partial hairpin DNA (2) in e.g. FIGS. 8A-8B with about 1-50, with a preferred range of 3-15, bases hybridized in the stem region can be generated by any suitable DNA synthesis technology (e.g. any recombinant or de novo synthesis technique), which will be appreciated by one of ordinary skill in the art in view of this disclosure. Appropriate DNA sequences for the second partial hairpin DNA can be determined by one of ordinary skill in the art based upon the direction provided elsewhere herein. This second partial hairpin DNA is also referred to herein in some aspects as an anchor recognizing unit. The second partial hairpin DNA can have one or more modified bases that can incorporate a reactive group or a linker that can contain a reactive group that can be capable of coupling an anchor recognition moiety. In some aspects, the modified base includes an anchor recognition moiety coupled to the modified base. In aspects, the modified base can be any non-5' (or 3' when considering the reverse) terminal base. In aspects, the modified base can be any internal (i.e., not the terminal 5' or 3' base). Thus, the anchor recognition moiety is incorporated in the DNA-nanostructure once assembled without needing further post-assembly reactions to attach the anchor recognition moiety. Suitable base modifications include, but are not limited to 2-aminopurine, 2,6-diaminopurine, 5-bromo-deoxyuridine, deoxyuridine, inverted dT, inverted Dideoxy-T, Dideoxycytidine, 5-methyl deoxycytidine, deoxyinosine, 5-hydroxybutynl-2'-deoxyuridine, 8-aza-7-deazaguanosine, 5-nitroindole, hydroxymethyl dC, Iso-dC, Iso-dG, 2' fluoro bases, 2'-O-methoxyethyl Bases (2'MOEs). Many suitable reactive groups are generally known to those of ordinary skill in the art. Suitable reactive groups include, but are not limited to, a carboxyl group, amino group, aromatic amine group, a chloromethyl group, an amide group, a hydrazide group, a hydroxyl, a thiol, an epoxy, an azide, click chemistry modifications, or a combination thereof.

In aspects, the second partial hairpin can have a sequence prior to base modification that is about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% to 100% identical to any one of SEQ ID NOs: 10-11. In aspects, the second partial hairpin can have a sequence prior to base modification that is about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical to any one of SEQ ID NOs: 10-11. It will be appreciated that any primary polynucleotide sequence is acceptable such that it can be assembled with other DNA-nanostructure components described elsewhere herein and generate the secondary structure as described elsewhere herein. In some aspects, the second partial hairpin can have a polynucleotide sequence prior to any optional base modification that does not share any identity with any of SEQ ID NOs.: 10-11, as long as the primary polynucleotide sequence is acceptable such that it can be assembled with other DNA-nanostructure components described elsewhere herein and generate the secondary structure as described elsewhere herein.

A single stranded DNA molecule (3) in e.g. FIGS. 8A-8B) can be generated that is configured to partially hybridize to the second partial hairpin DNA molecule. The single stranded DNA molecule can be generated by any suitable DNA synthesis technology (e.g. any recombinant or de novo synthesis technique), which will be appreciated by one of ordinary skill in the art in view of this disclosure. Appropriate DNA sequences for the single stranded DNA molecule can be determined by one of ordinary skill in the art based upon the direction provided elsewhere herein. The single stranded DNA molecule can include a signal molecule. The signal molecule can be coupled to the 5' end of the single stranded DNA molecule. Suitable signal molecules are described elsewhere herein. The signal molecule can be coupled to the 5' end via coupling to a modified or unmodified 5' terminal base or linker attached to 5' terminal base. The modification can provide a reactive group that can be used to couple, directly or indirectly via a linker, a signal moiety to the 5' terminal base. In aspects, the linker can contain a reactive group that can couple to a signal moiety. Suitable base modifications include, but are not limited to 2-aminopurine, 2,6-diaminopurine, 5-bromo-deoxyuridine, deoxyuridine, inverted dT, inverted Dideoxy-T, Dideoxycytidine, 5-methyl deoxycytidine, deoxyinosine, 5-hydroxybutynl-2'-deoxyuridine, 8-aza-7-deazaguanosine, 5-nitroindole, hydroxymethyl dC, Iso-dC, Iso-dG, 2' fluoro bases, 2'-O-methoxy-ethyl Bases (2'MOEs). Many suitable reactive groups are generally known to those of ordinary skill in the art. Suitable reactive groups include, but are not limited to, a carboxyl group, amino group, aromatic amine group, a chloromethyl group, an amide group, a hydrazide group, a hydroxyl, a thiol, an epoxy, an azide, click chemistry modifications, or a combination thereof. The single stranded DNA molecule can be modified prior to DNA-nanostructure assembly to include a signal moiety. In other aspects, the signal moiety can be coupled to the DNA-nanostructure after assembly.

In aspects, the single stranded DNA molecule can have a sequence prior to optional 3' (or 5' when considering the reverse) terminal base modification that is about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% to 100% identical to SEQ ID NO: 12. In aspects, the single stranded DNA molecule can have a sequence prior to base modification that is about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical SEQ ID NO: 12. It will be appreciated that any primary polynucleotide sequence is acceptable such that it can be assembled with other DNA-nanostructure components described elsewhere herein and generate the secondary structure as described elsewhere herein. In some aspects, the single stranded DNA molecule can have a polynucleotide sequence prior to any optional base modification that does not share any identity with SEQ ID NO.: 12, as long as the primary polynucleotide sequence is acceptable such that it can be assembled with other DNA-nanostructure components described elsewhere herein and generate the secondary structure as described elsewhere herein.

Table 1 provides reference and non-limiting polynucleotides that can be used to assemble a DNA-nanostructure described herein. It will be appreciated that the sequences provided in Table 5 reflect unmodified sequences and one of ordinary skill in the art will understand and be able to modify the various polynucleotides as described herein. Table 2 provides reference and non-limiting polynucleotides for an assembled DNA-nanostructure described herein based on the polynucleotides in Table 1. It will be appreciated that the sequences provided in Table 2 reflect unmodified sequences and one of ordinary skill in the art will understand and be able to modify the various polynucleotides as described herein.

TABLE 1

| Reference DNA sequences for assembly of a DNA nanostructures | | |
|---|---|---|
| SEQ ID NO: 9 | First partial hairpin DNA | CTG TGC AAG AAC TCAC AGC CTC ACC TCT TCC TAA AAA |
| SEO ID NO: 10 | Second partial hairpin DNA | GAG ACA CTG TGT CGT CTC CGG TTG AAG TGG AGA TAG GAA GAG GTG AGG |
| SEQ 10 NO: 11 | Second partial hairpin DNA | GGG CGA CTGT GTC CGC CCC GGT TGA AGT GGA GA TAG GAA GAG GTG AGG |
| SEQ 10 NO: 12 | Signal molecule DNA (single stranded DNA molecule. | TCTC CAC TTC AAC CG |

TABLE 6

| Reference polynucleotides for assembled DNA-nanostructures | |
|---|---|
| SEQ ID NO: 7 | TCTC CAC TTC AAC CG GAG ACA CTG TGT CGT CTC CGG TTG AAG TGG AGA TAG GAA GAG GTG AGG CTG TGC AAG AAC TCAC AGC CTC ACC TCT TCC TAA AAA |
| SEQ ID NO: 8 | TCTC CAC TTC AAC CG GGG CGA CTGT GTC CGC CCC GGT TGA AGT GGA GA TAG GAA GAG GTG AGG CTG TGC AAG AAC TCAC AGC CTC ACC TCT TCC TAA AAA |

As shown in FIG. 8A, the assembly of the DNA-nanostructure from the three components (whether coupled to a support structure or electrode surface or not) can occur in some aspects via self-assembly driven by equilibrium. Although this can result in assembly of the DNA-nanostructure, this process is inefficient.

As shown in FIG. 8B, a suitable DNA ligase can be used to assemble the components of the DNA-nanostructure in a non-equilibrium manner. Suitable DNA ligases include, but are not limited to, T4 DNA ligase, T7 DNA ligase, Taq DNA ligase, Electroligase, HiFi Taq DNA ligase, NxGen T4 DNA ligase, Ampligase, and T4 RNA ligase 2. In aspects, the three components of the DNA-nanostructure can be included in a reaction and contacted with an amount of a suitable DNA ligase and, under suitable reaction conditions, allowed to react with the DNA ligase to form the single molecule DNA-nanostructure. The volume and the concentration can be maneuvered, preferably 1 nM to 20 μM concentration of the components can be used, with the volume of 1 to 1000 μL. A ligase concentration of 1 to 100,000 U can be used. The preferred temperature of ligase reaction is 15 to 50 degrees C.

In addition to these manufacturing techniques, the DNA-nanostructures described herein can be made by any other suitable technique that will be appreciated by one of ordinary skill in the art in view of the instant description of the DNA-nanostructures herein.

Assays

The DNA-nanostructures described herein can be used in an assay to detect and/or quantify an analyte of interest. Suitable analytes of interest are described elsewhere herein. In general, the DNA-nanostructure can be contacted, directly or indirectly (e.g. via an anchor molecule) with a sample containing or is suspected of containing an analyte of interest. The sample can be a fluid. Solid samples of interest can be put into a liquid mixture or solution for analysis. Samples can be obtained from any suitable source, including but not limited to, a subject or an inanimate object or source (e.g. object source, soil, water source, air etc.). In some aspects, the sample is a complex sample (e.g. containing many types of compounds, molecules, and the like), such as blood or a component thereof (e.g. serum or plasma), soil, unfiltered water from a water source, etc. In some aspects the sample can be filtered by a suitable method prior to contact with the DNA-nanostructure. Suitable filtering methods include, but are not limited to, size separation-based methods (e.g. membrane-based, chromatography, and electrophoretic methods), charge separation-based methods e.g. membrane-based, chromatography, and electrophoretic methods), affinity purification methods (e.g. antibody, aptamer, magnetic, etc. based purification methods).

After contacting the DNA-nanostructure, directly or indirectly, with the sample that can contain or is suspected of containing an analyte of interest, the analyte of interest, if present, can bind the anchor molecule or anchor recognition moiety. If an anchor molecule is used, an anchor molecule containing a bound analyte can bind the anchor recognition moiety on the DNA-nanostructure. Binding of an analyte of interest or an anchor molecule bound to an analyte of interest can result in a change in tethered diffusion of the DNA-nanostructure as previously described. The signal produced, either directly or indirectly, from the signal moiety can be measured and used to indicate presence (or absence) of an analyte of interest and/or quantify an amount of an analyte of interest in a sample.

As previously discussed, the assay can operate based on direct binding of an analyte of interest to the anchor recognition moiety. FIG. 16 provides a summary of the steps of an assay direct (as exemplified by protein quantification) and indirect (as exemplified by small-molecule quantification, which is also illustrated in FIG. 17) detection of the analyte of interest. The analyte of interest can specifically bind the anchor recognition moiety. In other aspects, the analyte of interest can specifically bind an anchor molecule. In some aspects, the binding of an analyte of interest to the anchor molecule can result in a conformational change in the anchor molecule, which allows it to then specifically bind to the anchor recognition moiety. In some aspects, binding of an analyte of interest to the anchor molecule does not result in a conformational change in the anchor molecule. The assay can include any suitable number of rinses or washes to remove unbound analyte of interest between steps of sample incubation and signal measurement. In some aspects the number of washes can range from 1 to 100. Suitable buffers can include, but are not limited to, phosphate buffered saline, HEPES, cell media, Tris, Tris-EDTA, or any buffer known by those skilled in the art that will not interfere with the measurement of interest.

As previously discussed, the detection of the signal moiety can occur directly (e.g. measuring a signal produced by the moiety itself or indirectly (e.g. a signal produced by something that the signal moiety interacts with to produce a detectable signal when a stimulating interaction occurs). For direct detection, the signal molecule can produce an optical signal (e.g. florescence) that can be detected and measured by a suitable device. Suitable devices include, but are not limited to, fluorescence spectrometer, microscope, optical photometer, laser-induced fluorescence system, confocal fluorescence system, single-molecule detection apparatus, time-resolved fluorescence instrument, polarized fluorescence instrument, or any instrument capable of exciting the label and quantifying photons known to those skilled in the art. In aspects, where the signal is directly detected from the signal moiety, detection and/or quantification can be made by directly measuring a signal output from the signal moiety. A change in 3D position or frequency of a change in position over time can be measured by measuring the optical signal at a stationary position. In some aspects, an optically active signal moiety is always producing an optical signal and thus measuring the optical signal at a stationary position allows detection of binding of an analyte to the DNA-nanostructure. In some aspects, a signal is produced by an optically active signal moiety via FRET or other proximity- or resonance-based signal production method. In such aspects the signal can still be produced from the signal moiety, but only when it is in effective proximity to an energy donor. When this occurs, the signal molecule (or energy acceptor) can reach an excited state and produce an optical signal, which can be detected and measured as previously described. In some aspects, the DNA-nanostructure can be coupled to a support structure that can include a photodetector and a suitable energy donor molecule. When the signal moiety that is an energy acceptor comes in proximity to the suitable energy donor molecule, the signal moiety can produce an optical signal that can be detected by the photodetector. A change in the signal and/or frequency of signal production can be used to determine presences and/or amount of an analyte of interest as previously discussed.

In other aspects, the assay can be configured such that the signal is indirectly produced from the signal moiety. In these aspects, the signal moiety causes the production of a signal by something else (e.g. electrode, energy acceptor optically active molecule etc.) by reacting with another molecule and/or electrode. In some aspects, the signal moiety is a redox molecule that produces a chemical change (e.g. a redox reaction) with a suitable surface or other molecule which can be translated into a signal by an electrode and/or detector. In some aspects, the signal moiety is an energy donor molecule that can react with an optically active energy acceptor that can be coupled to a support and/or photodetector and stimulate production of a detectable optical signal from the optically active energy acceptor via energy transfer from the signal moiety to the energy acceptor molecule when they are in effective proximity to each other. The signal produced from the energy acceptor molecule can be detected by, e.g., a photodetector. A change in the signal and/or frequency of signal production either produced via a chemical (e.g. redox) reaction or optically can be used to determine presence and/or quantify amount of an analyte of interest as previously discussed. In some aspects, a change in the electrochemical reaction rate can be used to determine the presence and/or quantify the amount of an analyte of interest. This can be measured in some aspects by a change in the current, such as an SVW current, that can be applied to an electrode.

In aspects, properties of the redox molecules can be interrogated with any electrochemical quantification technique, including but not limited to cyclic voltammetry (CV), linear sweep voltammetry, pulse voltammetry, chronoamperometry, square wave voltammetry (SWV), differential pulse voltammetry (DPV), AC voltammetry, fast-scan CV, etc. For interrogating the DNA-nanostructure 1000, one possible algorithm to follow is to first measure the initial signal without analyte present. The target introduction will then induce binding of the anchor molecule, thereby shifting the output from the initial level. The percentage of shift or the magnitude of the shift, compared to the initial signal, is proportional to the target concentration. The target introduction could also induce displacement of the anchor molecule, thereby shifting the output from the initial level, and the percentage of shift or the magnitude of the shift, compared to the initial signal, is proportional to the target concentration. Specific examples using SVVV are given below.

The DNA-nanostructure described herein can be more sensitive than other conventional DNA based electrochemical assays for the same analyte. This can be due in part to the structural configuration of the DNA-nanostructure. The dynamic range of the DNA-nanostructure based assay described herein can be range from the nanomolar range to the micromolar range. The dynamic range of the DNA-nanostructure based assay can range from about 1 nm to 10 μm. In aspects, the dynamic range of the DNA-nanostructure based assay described herein can be from about 2 nm to 100 nm. In aspects the dynamic range of the DNA-nanostructure based assay described herein can range from about 1 μm to about 8 μm. The dynamic range of the DNA-nanostructure can be based in part, on the structure of the DNA-nanostructure, the analyte being detected, whether or not the DNA-nanostructure is coupled to a support or electrode surface, whether or not an anchor molecule is used in the assay to specifically bind an analyte of interest, which will be appreciated by one of ordinary skill in the art in view of this disclosure.

Components of the assay described herein can be provided as a combination kit. The combination kit can include a DNA-nanostructure as described herein and an optional anchor molecule. The kit can also include solutions, diluents, buffers, reagents, containers, membranes, plates (e.g. 6, 12, 24, 48, 64, 96, 384 well plates), that can be used in sample preparation and/or assay performance.

FIGS. 18A-18C can illustrate the principle of using nucleic acid aptamers in the framework of the nanostructure at an electrode surface. Aptamers can be used as the anchor as in FIG. 18A. While serving as anchor, aptamer-induced responses could be further enhanced by conjugation to a larger protein such as streptavidin as in FIG. 18B. Another example is shown in FIG. 18C, where the aptamer is conjugated to the nanostructure, in this case serving as the anchor recognition moiety.

FIGS. 19A-19B can demonstrate using the nucleic acid nanostructure for monitoring of bioconjugation reactions. In one example, a peptide drug (exendin-4) was successfully activated and attached to the nanostructure as in FIG. 19A. This bioconjugation process could be monitored using square-wave voltammetry as in FIG. 19B, where the faradaic peak current was reduced due to the slowed tethered diffusion rate of the methylene blue label (signal moiety). A similar effect was observed when attaching a slightly larger, globular protein, insulin as shown in FIGS. 19C-19D.

FIGS. 20A-20D can demonstrate the results of peptide antibody quantification (exendin-4 antibody) as in FIGS. 20A-20B. The same nanostructure can be used for indirect quantification of the same peptide in free solution (from the sample), as in FIGS. 20C-20D. Successful exendin-4 quantification results are shown in FIG. 20D.

FIG. 21 can demonstrate using the nanostructure for enzyme activity monitoring. Cleavage of a peptide (or other biomolecule) attached to the nanostructure can be monitored during the reaction using the nanostructure's signal. This concept is feasible for either cleavage reactions or ligation (additive) reactions.

Various modifications and variations of the described compositions, methods, and assays, and kits of the invention will be apparent to those skilled in the art without departing from the scope and spirit of the disclose. Although the various aspects of the DNA-nanostructure, systems thereof, manufacture thereof, and uses thereof have been described it will be understood that they can be further modified and that the invention as claimed should not be unduly limited to such specific aspects. Indeed, various modifications of the described modes for carrying out the invention that are obvious to those skilled in the art are intended to be within the scope of the invention. This application is intended to cover any variations, uses, or adaptations of the invention following, in general, the principles of the disclosure and including such departures from the present disclosure come within known customary practice within the art to which the disclosure pertains and can be applied to the essential features herein before set forth.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure. The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Example 1

Materials and Methods

Reagents and Materials.

All solutions were prepared with deionized, ultra-filtered water (Fisher Scientific). The following reagents were used as received: 4-(2-hydroxyethyl)-1-piperazineethanesulfonic acid (HEPES) from Alfa Aesar, magnesium chloride hexahydrate from OmniPur and sodium chloride from BDH.

tris-(2-carboxyethyl) phosphine hydrochloride (TCEP), digoxigenin, mercapto hexanol (MCH), gold etchant, and chromium etchant from Sigma-Aldrich. Anti-digoxigenin (monocolonal and polycolonal) from Roche. Biotin from Amresco. Gold-sputtered on glass (GoG) (Au 100 nm with Cr adhesion layer 5 nm) from Deposition Research Lab, Inc (St. Charles, Mo.) with dimension 1"×3"×1.1 mm. AZ 40XT (positive thick photoresist) and AZ 300 MIF developer from Microchemicals, polydimethylsiloxane (PDMS) from Dow Corning Corp, and dimethyl sulfoxide (DMSO) from anachemia. Methylene blue-conjugated DNA was purchased from Biosearch Technologies (Novato, Calif.), purified by RP-HPLC. Thiolated-DNA and anchor-DNAs were obtained from Integrated DNA Technologies (IDT; Coralville, Iowa), with purity confirmed by mass spectroscopy, T4 DNA ligase (400000 units), streptavidin, and adenosine triphosphate (ATP, 10 mM) are bought from New England Bio, human serum from BioreclamationIVT, DNAs are listed in Table 3. For streptavidin and biotin quantification, the DNA nanostructure was constructed with DNAs having a sequence according to SEQ ID NOS.: 13, 14, and 16. For digoxigenin and anti-digoxigenin DNAs having a sequence according to SEQ ID NOS.: 13, 15, and 16 were used.

TABLE 3

List of DNA sequences used in Example 1.

| SEQ ID | Description | Sequence |
|---|---|---|
| SEQ ID NO: 13 | Thiolated DNA | **/5Phos/** CTG TGC AAG AAC TCAC AGC CTC ACC TCT TCC TAA AAA **/3ThioMC3-D/** |
| SEQ ID NO: 14 | Anchor DNA (Streptavidin and biotin quantification) | **/5Phos/** GAG ACA CTG TGT CGT CTC CGG TTG AAG TGG AGA **/ideSBioTEG/** TAG GAA GAG GTG AGG |
| SEQ ID NO: 15 | Anchor DNA (Anti-digoxigenin and digoxigenin quantification) | **/5Phos/** GGG CGA CTGT GTC CGC CCC GGT TGA AGT GGA GA **/iDIgN/** TAG GAA GAG GTG AGG |
| SEQ 1D NO: 16 | Methylene blue DNA | **/dT MB**/CTC CAC TTC AAC CG |

Preparation of Gold Electrodes and Electrochemical Cells.

Figures 10A, 10B, 10C:
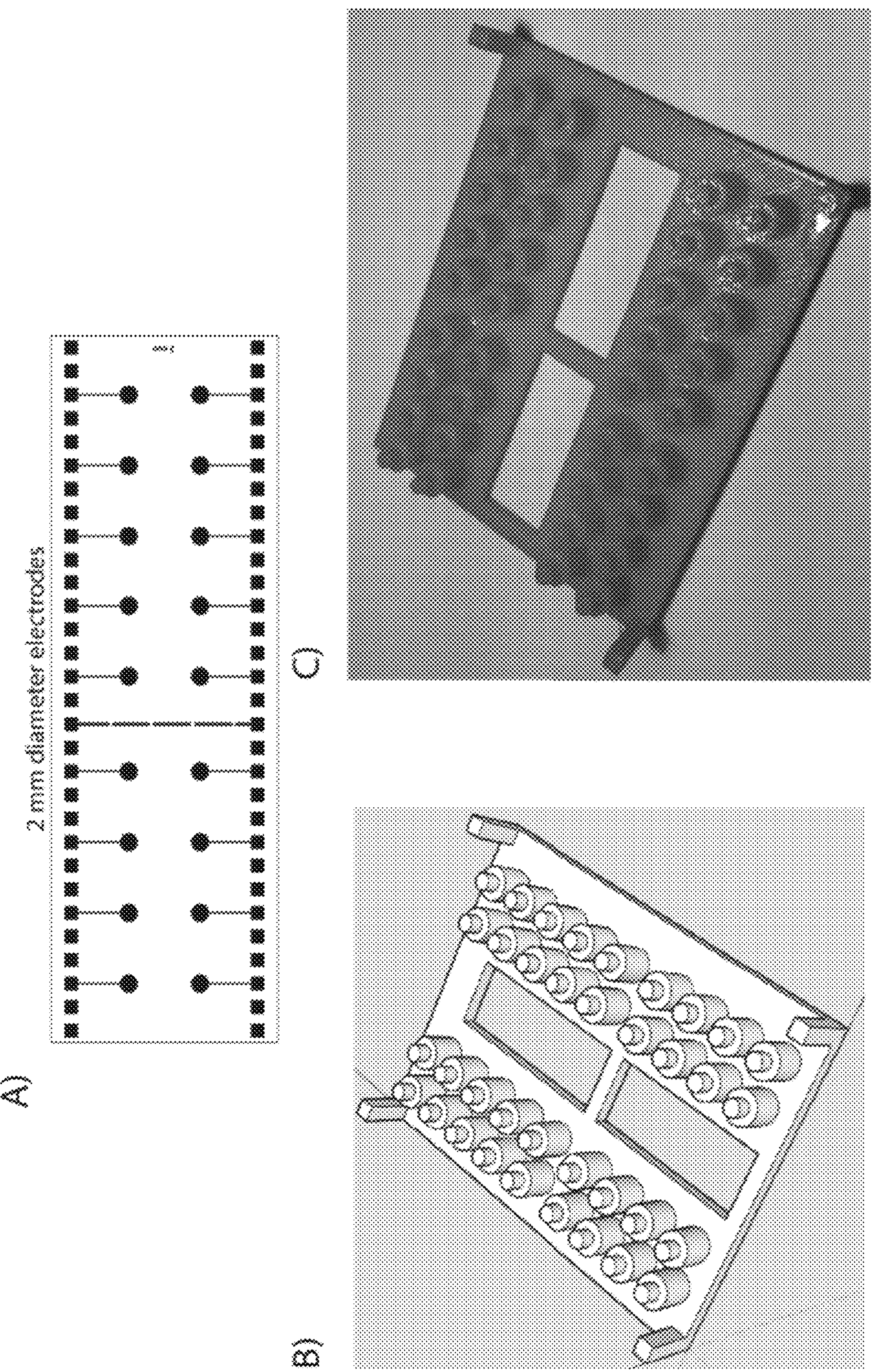
FIGS. 10A-10C show (FIG. 10A) Photomask design used for gold-on-glass (GoG) preparation. In total, 18 independent 2-mm diameter gold working electrodes were prepared using this mask.

A protocol similar to that used in Somasundaram, S.; Holtan, M. D.; Easley, C. J. Anal. Chem. 2018, 90 (5), 3584-3591 was employed here. Electrode masks were designed in Adobe Illustrator, and files were sent to Fineline Imaging (Colorado Springs, Colo.) for printing positive photomask. FIG. 10A shows the mask design. In total there are eighteen 2 mm diameter electrodes in one microscopic slide. A 3D computer animated design (CAD) file was designed in Sketchup© program (Trimble Navigation Limited), and Makerbot Replicator 2 (200 μm layer resolution in the z-direction) with Hatchbox's polylactic acid filament (PLA, 1.75 mm diameter) was used to print the 3D mold. FIG. 10B shows the 3D CAD and mold. Each electrode in placed in an individual electrochemical cell of about 100 μL volume. Therefore, eighteen different samples can be evaluated on a single one microscopic slide.

DNA Monolayer Assembly.

Electrodes were cleaned with piranha solution prior to plasma oxidation of electrochemical cell. The piranha solution ($H_2SO_4$:$H_2O_2$, 3:1) was freshly prepared and dropped onto the surface of the electrode for 1 minute, later the electrodes was rinsed with deionized water. IDT recommended to reduce the dithiol bond prior to usage. The thio-DNA was reduced by reducing agent TCEP. To reduce 1 μL of 200 μM thio-DNA, 3 μL of 10 mM TCEP was mixed and incubated at room temperature in dark for 1 hour. The solution was then diluted with HEPES 10 mM with $MgCl_2$ 10 mM at pH 7 buffer (final thio-DNA concentration of 1250 nM and 30 nM was used for streptavidin and anti-digoxigenin nanostructure respectively). 100 μL of thio-DNA was introduced into each electrochemical cell and incubated for 1 hour at room temperature. Then electrode was rinsed and 3 mM MCH in HEPES 10 mM with $MgCl_2$ 10 mM at pH 7 buffer was introduced into electrochemical cell and incubated for 1 hour. After this the electrode can be rinsed and can be stored in refrigerator with HEPES 10 mM with MgCl2 10 mM at pH 7 for a week.

DNA Nanostructure Construction.

Once the electrode was ready for construction 100 nM of anchor-DNA and MB-DNA was prepared in HEPES buffer (10 mM HEPES with MgCl2 10 mM and 1 mM ATP at pH 7). 100 μL of the mixture was introduced in to electrochemical cell. Following this, 0.5 μL of 400000 U T4 DNA ligase was added in each electrode with the mixture. The setup needs to be placed undisturbed for a minimum of 4 hours at room temperature. Then electrode was rinsed with deionized water to remove enzymes and excess DNAs. Later, the electrode was incubated with HEPES 10 mM with NaCl 0.5 M at pH 7 buffer with 0.1% BSA for at least 30 minutes.

Electrochemical Measurements.

All electrochemical measurements were executed using Gamry Reference 600 potentiostat. Once the electrode was ready to measure, the silver/silver chloride (3 M KCl) reference (BASi) and platinum counter (CH instruments) were introduced into the electrochemical cell. Square-wave voltammetry was measured from −0.45 to 0 V (vs reference electrode) with step size 1 mV, pulse height 25 mV, and SWV frequency of 100 Hz (streptavidin and biotin) or 20 Hz (digoxigenin and anti-digoxigenin).

DNA Melting Analysis.

Bio-Rad CFX96 real-time quantitative PCR instrument (qPCR) was used. Assay mixture containing 500 nM of thio-DNA, anchor-DNA, and MB-DNA in buffer provided by New England Bio was prepared. The mixture was divided into two batches in which 1 μL of 400000 U T4 DNA ligase was added to one batch and incubated in room temperature for 4 hour. Following this, 1×SYBR Green was added to both batches and incubated for 15 minutes. Later, the components were transferred to qPCR tubes and placed in the instrument. The temperature was scanned from 4° C. to 90° C. at 0.5° C. min-1. Fluorescence was measured at each set temperature after 10 s equilibration, with 470±20 nm excitation and 520±10 nm emission filters.

Quantification Protocols.

Streptavidin Quantification.

DNA nanostructure was constructed with desthiobiotin anchor recognition unit. Once the construction was done, the electrode was ready for initial SVVV measurement in HEPES 10 mM with NaCl 0.5 M (pH 7, 0.1% BSA) buffer 100 μL volume. Various concentrations of streptavidin were prepared in HEPES 10 mM with NaCl 0.5 M (pH 7, 0.1% BSA) buffer. The electrochemical cell was emptied, and 20 μL of sample was introduced into the cell and incubated at room temperature for 1 hour. Then the sample was removed and a 100 μL final measurement was done in the same buffer.

Anti-Digoxigenin Antibody Quantification.

A similar protocol was followed as streptavidin quantification, except the digoxigenin tagged anchor-DNA was used in nanostructure construction.

Biotin Quantification.

Anchor-DNA with desthiobiotin as anchor recognition unit was used to construct DNA nanostructure. Following the construction, 20 μL of 1000 nM streptavidin (HEPES 10 mM with NaCl 0.5 M (pH 7, 0.1% BSA)) was introduced and incubated for 4 hours at room temperature. Later the solution was removed and initial SWV measurement was made in HEPES 10 mM with NaCl 0.5 M (pH 7, 0.1% BSA) buffer 100 μL volume. Following this, 20 μL of biotin sample was introduced and incubated for 1 hour at room temperature. Then the sample was removed and 100 μL final measurement was done in the same buffer.

Digoxigenin Quantification.

Digoxigenin appended anchor-DNA was used to construct the DNA nanostructure. Later, the electrode was incubated overnight at 4° C. with 20 μL of 100 nM anti-digoxigenin. Following this, a protocol similar to that of biotin quantification was followed.

Measurement in Minimally Diluted Human Serum.

Anti-digoxigenin was spiked into human serum, giving a 1:9 ratio (making it 90% serum). For negatives (serum without anti-digoxigenin), control undiluted serum was used. The same protocol as mentioned above for anti-digoxigenin quantification was followed.

Data Analyses.

Peak Height.

Figure 11:
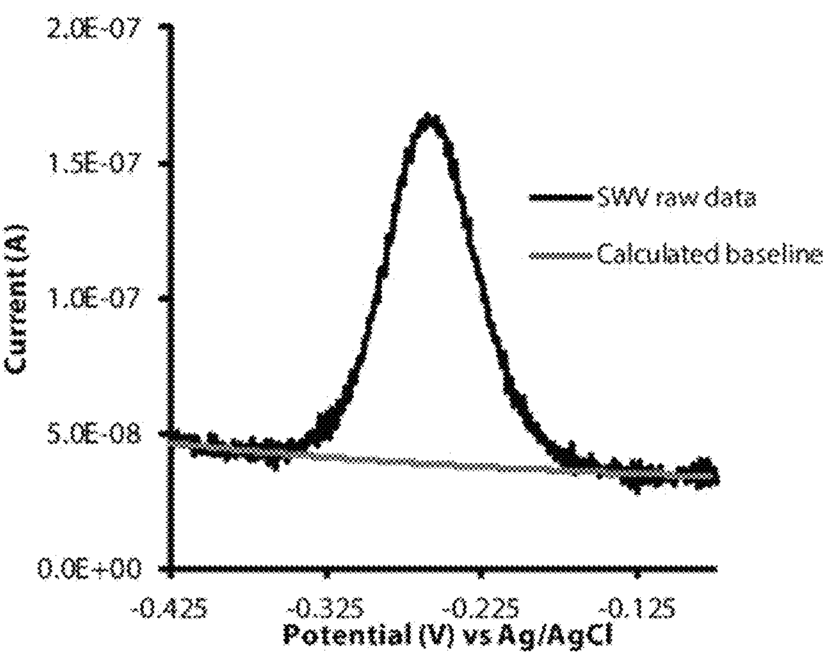
FIG. 11 shows a graph that can demonstrate an example MB-DNA redox current during SWV (raw data) along with the calculated baseline curve used for Faradaic current extraction.
Figure 12:
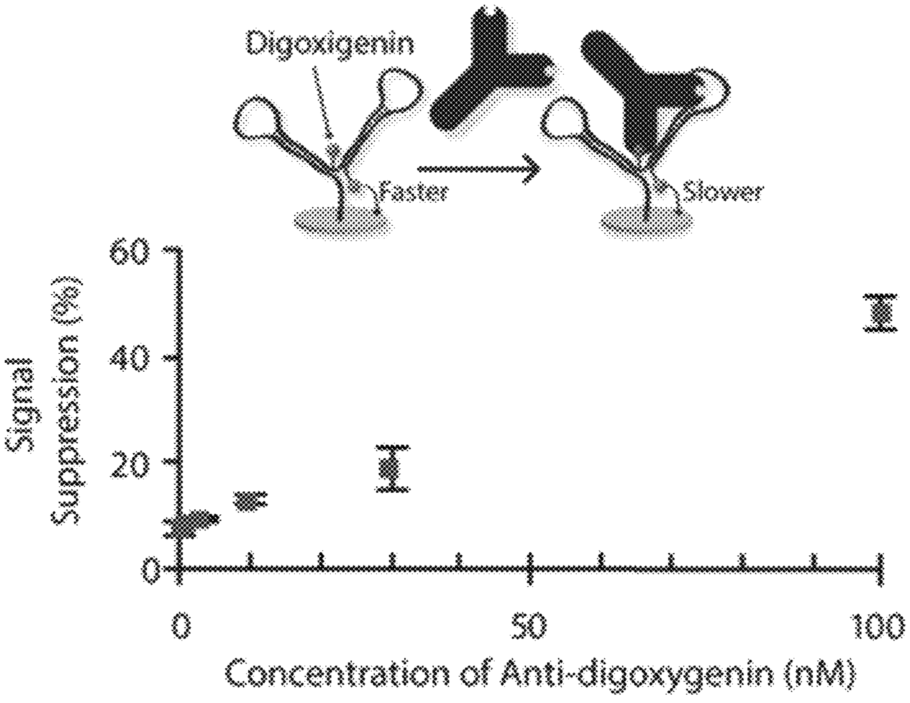
FIG. 12 shows a graph and cartoon that can demonstrate quantification of polyclonal anti-digoxigenin antibodies. On comparison to the monocolonal antibody, a decrease in sensitivity was observed due to the presumably modified antibody-antigen binding.
Figures 13A, 13B:
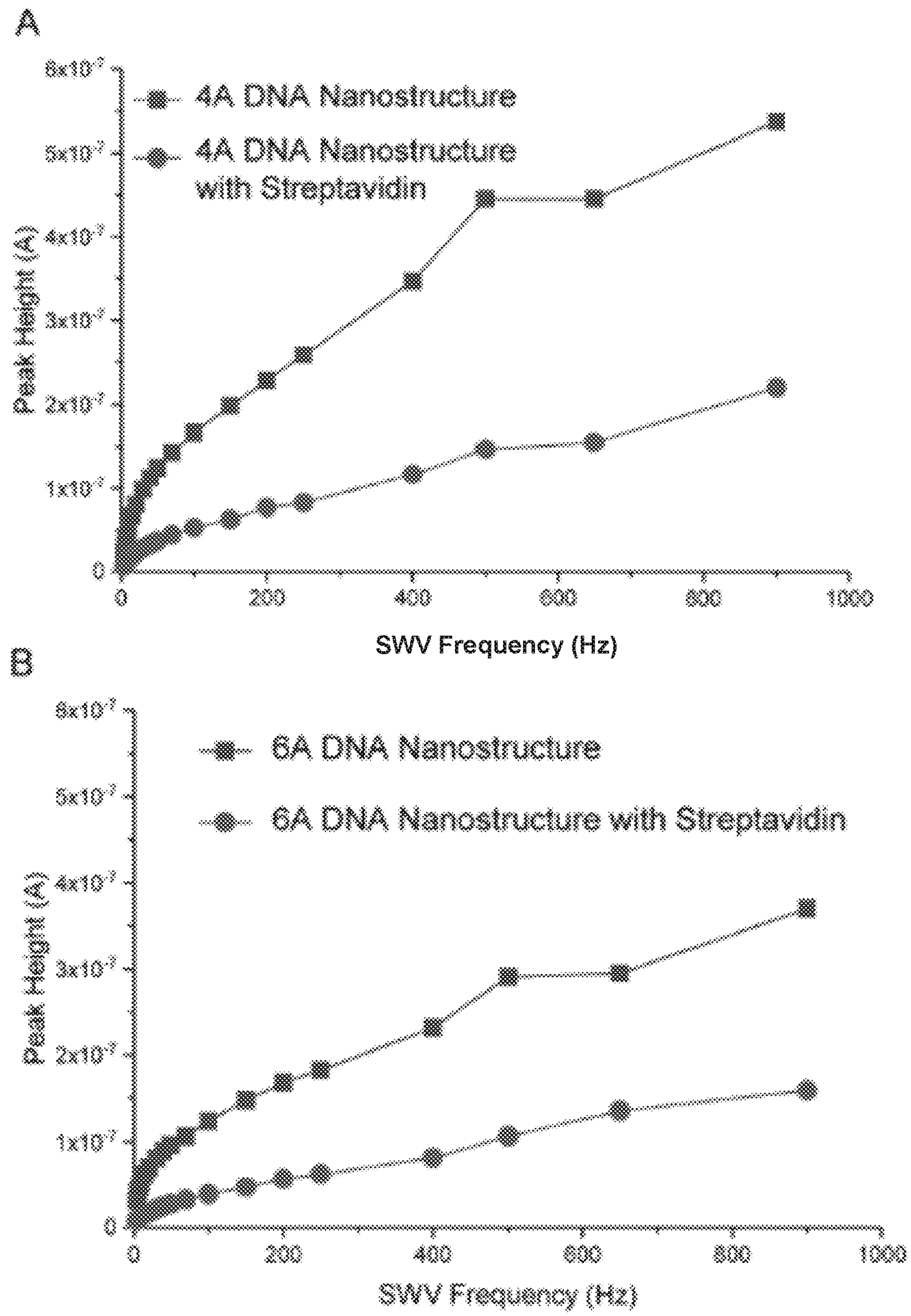
FIGS. 13A-13D show graphs that can demonstrate signal suppression and comparison of varying distance. Comparison of signal from four different complexes, which places the redox moiety at a distance of 4 A, 6 A, 8 A, and 10 A. 4 A was observed to undergo a large percentage of signal suppression.
Figure 13C:
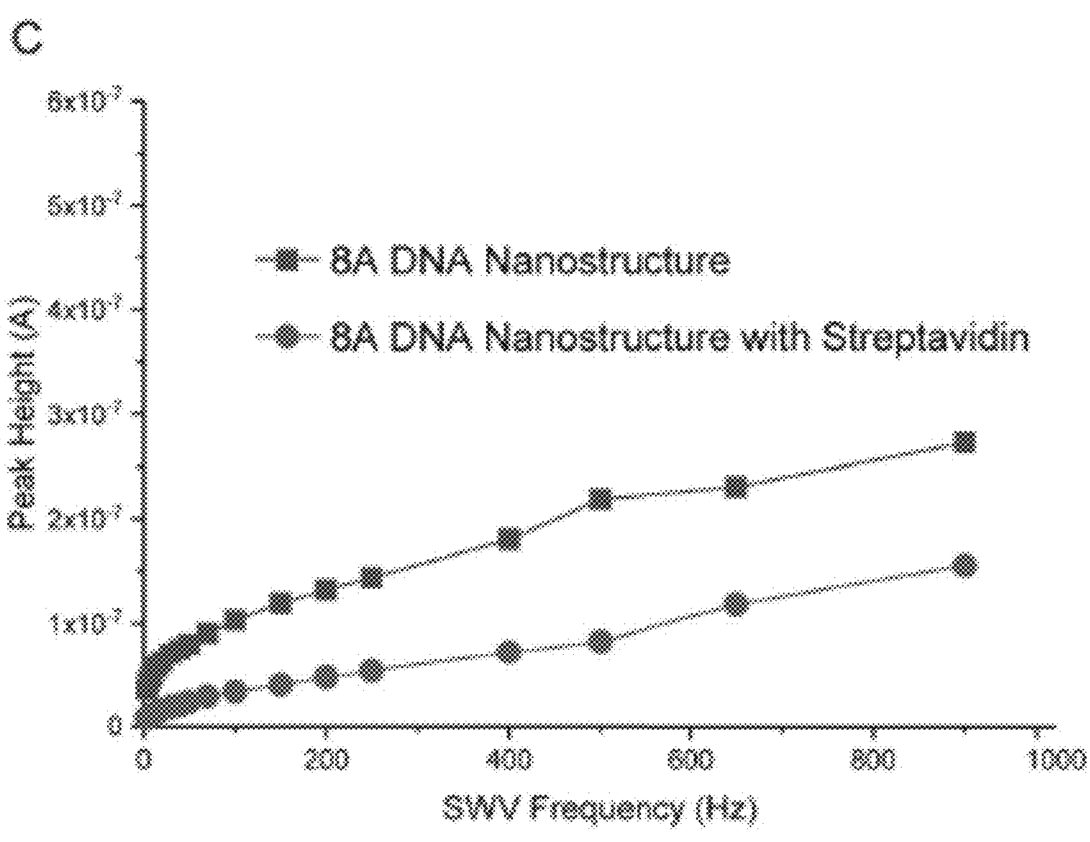
Figure 13D:
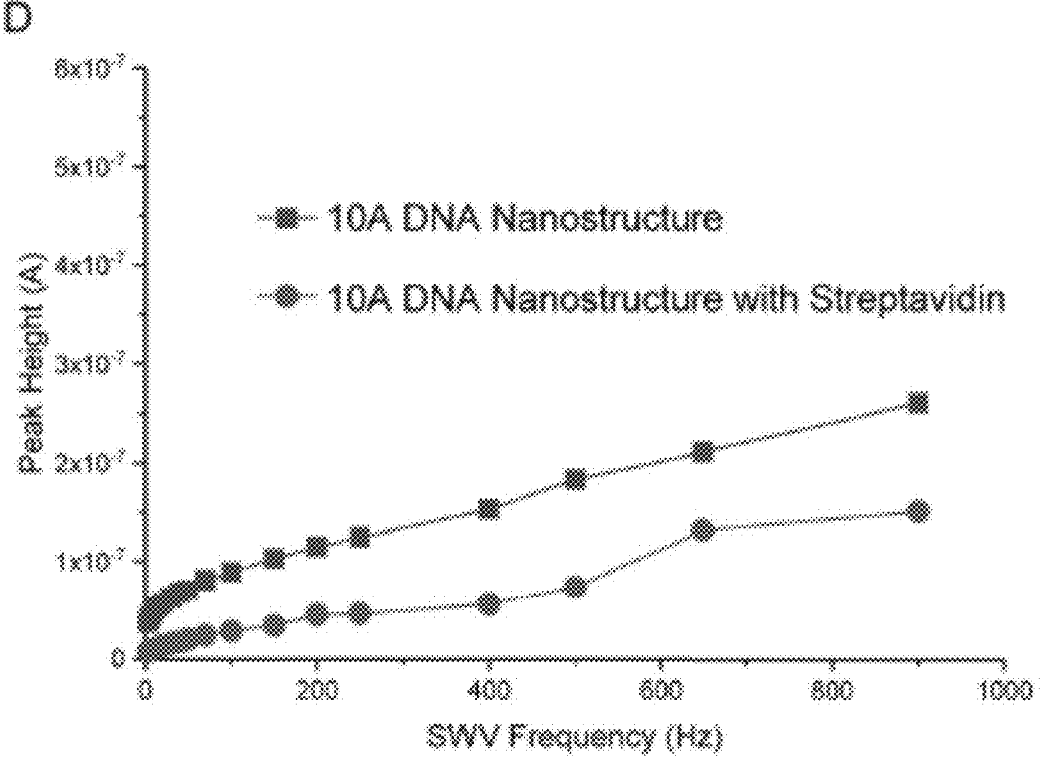

SWV raw data (including Vstep and Idiff) was transferred to Microsoft Excel, and a 9-point moving average was applied. To remove capacitance current, a third-order polynomial baseline was calculated using the "Linest" function in EXCEL. Data points from −0.445 to −0.370 V and −0.150 to −0.005 V were used in this calculation. The calculated baseline was subtracted from the raw data. An example is shown in FIG. 11. The maximum current from this graph was used as the peak height.

Signal suppression and signal change. Equations 1 and 2 were used to calculate signal suppression and change, where ip (initial) is the peak height of the initial current measurement (before target incubation) and ip (final) is the peak height of the final current measurement (after target incubation).

$$\text{Signal Suppression (\%)} = -100\times\frac{i_p(\text{final}) - i_p(\text{initial})}{i_p(\text{initial})} \quad \text{(Eq. 1)}$$

$$\text{Signal Change (\%)} = 100\times\frac{i_p(\text{final}) - i_p(\text{inital})}{i_p(\text{inital})} \quad \text{(Eq. 2)}$$

Results

Figures 3A, 3B:
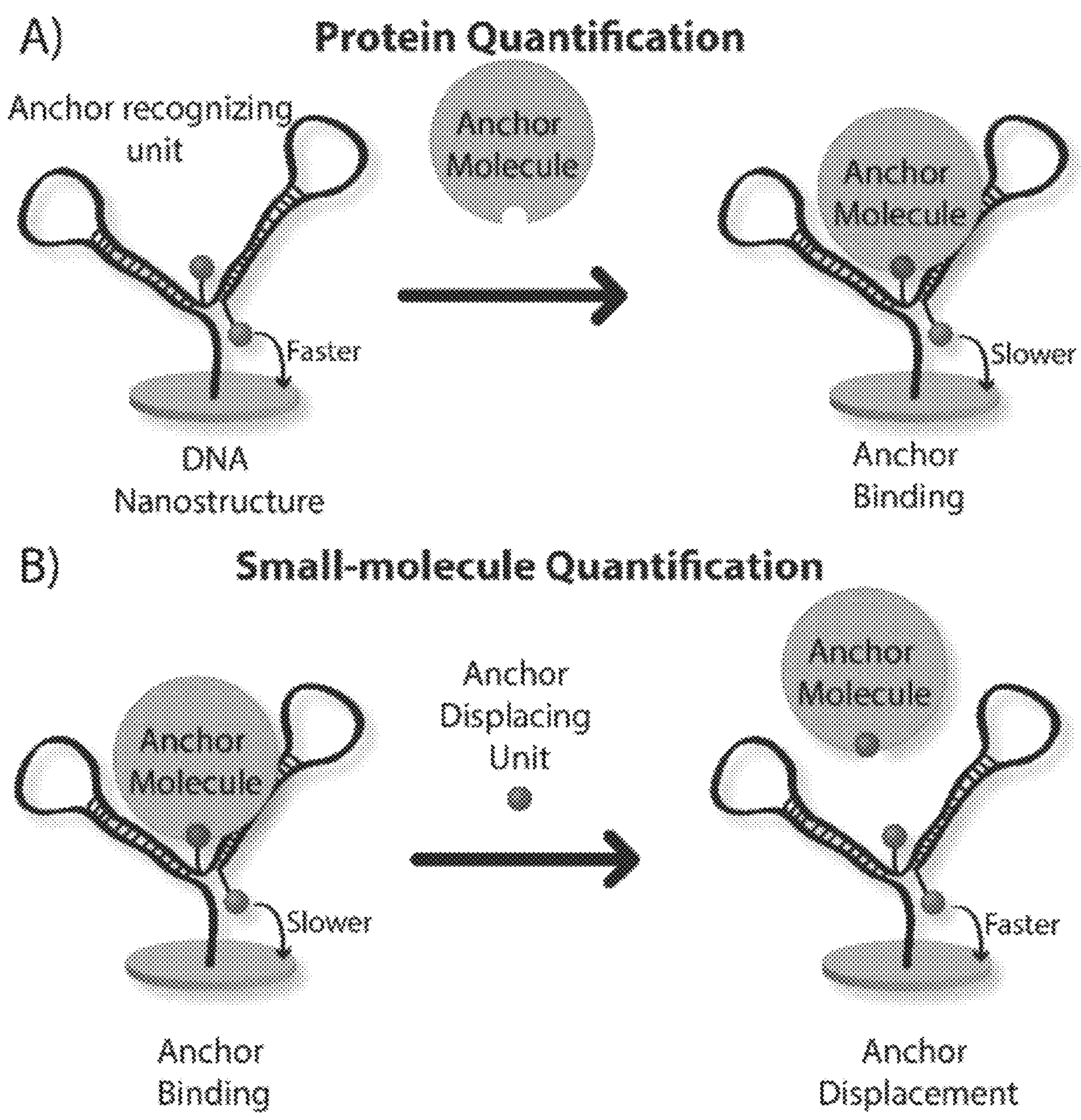
FIGS. 3A-3B show (FIG. 3A) In protein quantification mode, the redox molecule's tethered diffusion is initially fast but slowed by anchor molecule binding and (FIG. 3B) Small-molecule quantification mode starts with slower diffusion, but anchor displacement by target promotes faster diffusion and higher SWV current.

As demonstrated and described in at least this Example, a DNA nanostructure was generated and attached at a fixed distance from a support surface and configured to electrochemically report a variety of binding interactions. Such a nanostructure undergo a change in mass upon binding, which shift the tethered diffusion21 resulting in electrochemical signal change. FIGS. 3A-3B can depict a protein and small molecule sensor design, both based on the same DNA nanostructure. The tethered diffusion is altered by either attachment or displacement of an anchor molecule to the anchor recognition unit in the nanostructure. To optimize signal change, the DNA nanostructure was designed and configured to: 1) position redox molecules into close proximity with the anchor recognizing units; and 2) ensure the probe has a flexible tether between the electrode and the redox label. In FIG. 3A, for drop-and-read protein quantification, initially the DNA nanostructure was configured to have a faster tethered diffusion, which on protein binding (anchor) slows, reducing electrochemical signal proportional to anchor concentration. In the small-molecule quantification design (FIG. 3B) the probe was configured as an anchor molecule pre-bound to the DNA nanostructure, starting with slow tethered diffusion. Upon introduction of target molecules in a drop- and read manner, the anchor is displaced into the solution, increasing signal by enhanced diffusion of the nanostructure. Two pairs of small molecules and protein partners: 1) streptavidin (52.8 kDa) and biotin (244.31 Da) due to the strong interaction; and 2) digoxigenin (390.51 Da) and anti-digoxigenin (about 150 kDa) for the clinical relevance of antibodies were chosen to evaluate the DNA nanostructure.

The DNA nanostructure described herein incorporates an electrode immobilizing moiety (e.g. thiol or amine), a target recognizing region (e.g. aptamer, target binding small molecule, protein), and a redox label. In conventional DNA-based electrochemical sensor probes, this combination is attained by either synthesizing probes as single units or constructing them on-demand through DNA hybridization. However, appending DNA with two or three modifications can result in very low yields, even from the best commercial sources. In contrast to conventional DNA-based electrochemical sensor probe designs, the DNA nanostructure demonstrated in at least this Example incorporates a DNA-selective enzyme, T4 DNA ligase, for probe construction which results in a single molecule structure. Three singly-conjugated DNA sequences (Table 3), one with dithiol (thio-DNA), the second with an internal small-molecule label (anchor-DNA), and a third with methylene blue redox tag (MB-DNA). One crucial benefit of this construction is the low cost. With commercial synthesis, success with multiple conjugations can vary, and most companies hesitate to even attempt it due to the tedious, inefficient process. These custom-made probes are approximately 600% more expensive than our probes made by on-electrode enzyme ligation.

Figures 4A, 4B, 4C:
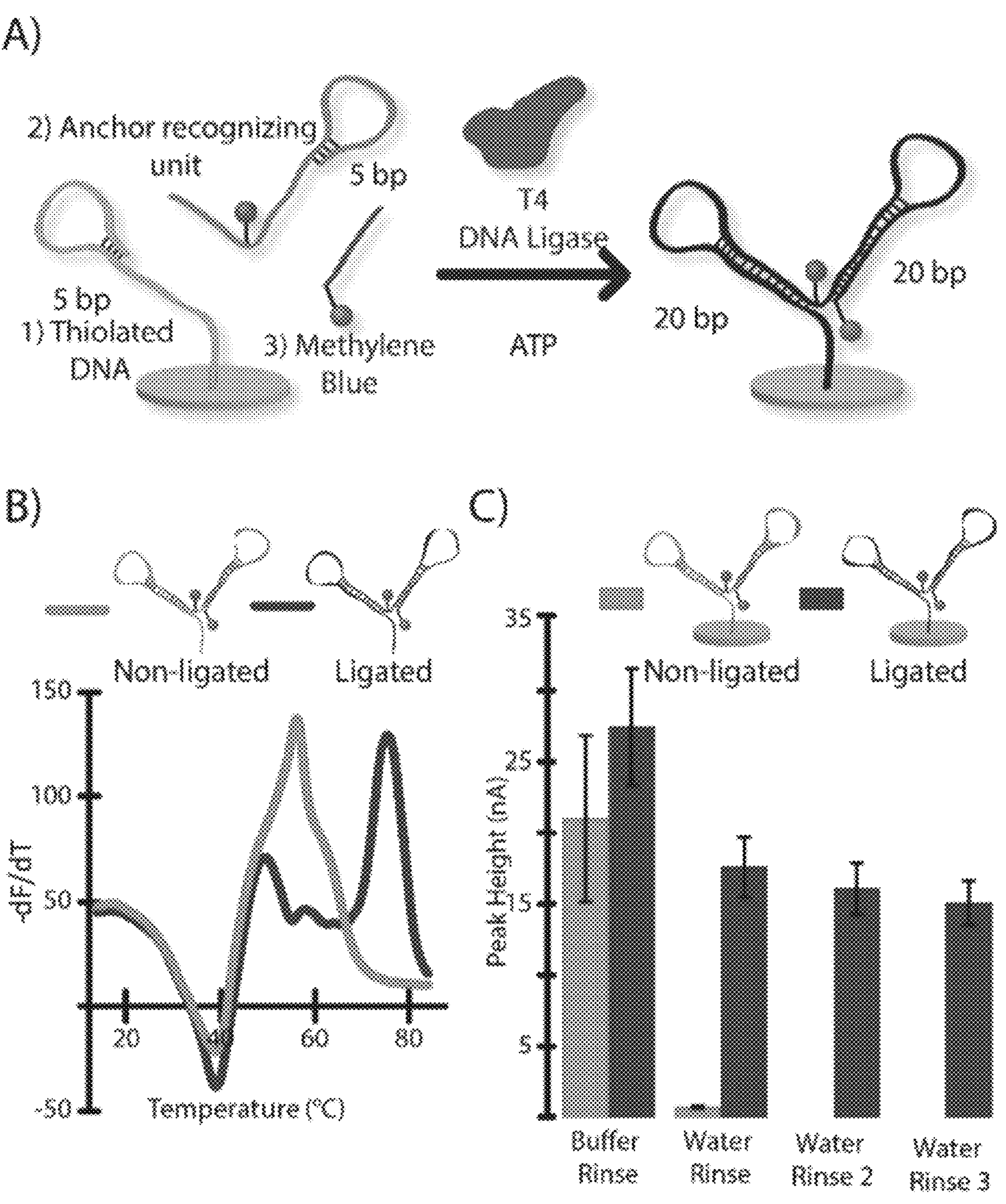
FIGS. 4A-4C show aspects of DNA nanostructure assembly.

FIG. 4A depicts the DNA nanostructure's initial hybridization design and final product after T4 DNA ligation. The anchor-DNA (red) binds with thio-DNA (blue), and the MB-DNA (brown) binds with anchor-DNA (red), both with 15 base-pairs. This hybridization positions the 5'-phosphorylation of thio-DNA and anchor-DNA in close proximity to 3' of anchor-DNA and MB-DNA, respectively, assisted by intrastrand hairpin loops. These locations are selectively ligated by the enzyme, forming a single entity (black) with three components into one DNA nanostructure for electrochemical sensing. To confirm the ligation, a free-solution DNA melting study with a DNA-intercalating fluorescence dye, SYBR green, was conducted. While the non-ligated complex has four separate and weaker hybridizations (two multi-strand 15-bp; two 5-bp hairpins), the fully-ligated complex has two 20-bp intramolecular hairpins, which are significantly more stable. Indeed, in FIG. 4B we observed the melting temperatures of non-ligated and ligated complexes were around 55° C. (light gray) and 75° C. (dark gray) respectively, affirming ligation success.

For building the DNA nanostructure on electrode surfaces, thio-DNA was immobilized on the gold electrode in a self-assembled monolayer. Later, the other two DNAs were introduced into the electrochemical cell and enzymatically ligated. After construction, the electrode was rinsed with water to remove unreacted strands and enzymes. FIG. 4C shows the stability of the DNA nanostructure on the electrode surface. In the absence of ligase, the nanostructure is bound by non-covalent hybridization, an equilibrium process (FIGS. 8A-8B). In buffer it exhibited about 20 nA of SWV current, but when exposed to water the non-ligated components dissociated (light gray bars, FIG. 4B). ligated nanostructure was stable on the surface even after four rinses (dark gray bars, FIG. 4B), with a surface yield of about 60%. These data can confirm successful construction and stability of the DNA nanostructure on the electrode surface.

Figures 5A, 5B, 5C, 5D:
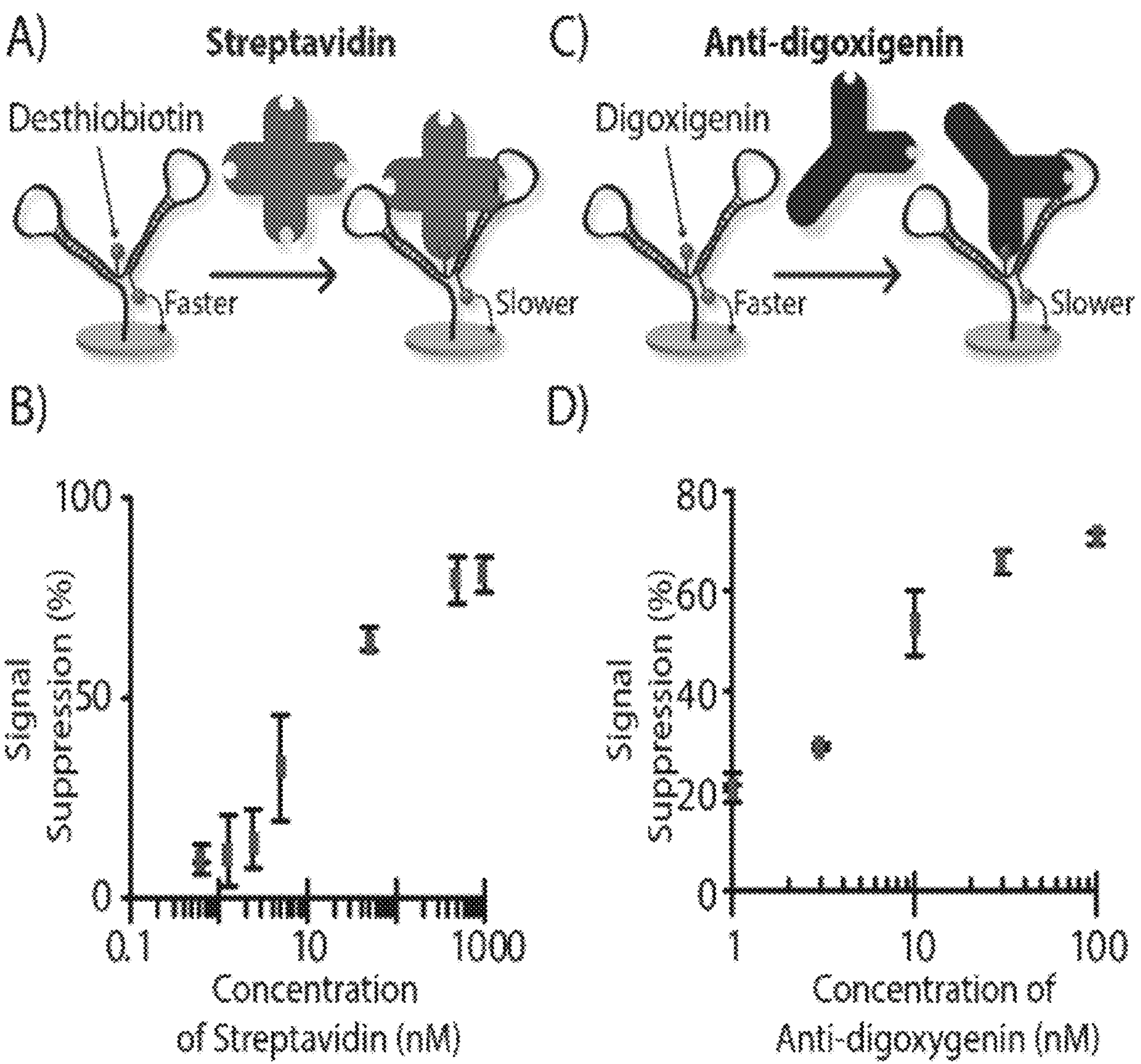
FIGS. 5A-5D show aspects of protein quantification mode.
Figures 9A, 9B:
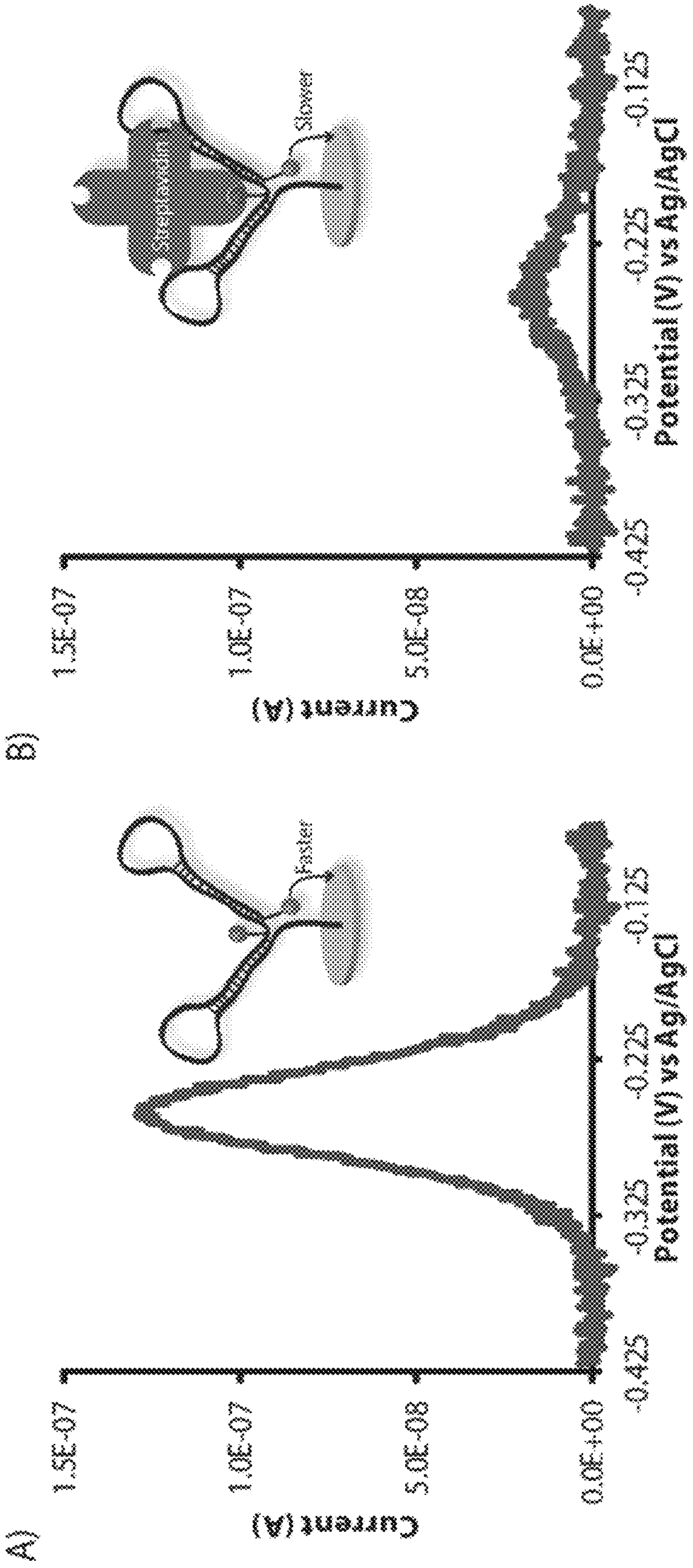
FIGS. 9A-9B show graphs that can demonstrate (FIG. 9A) Baseline corrected SVVV output of the DNA nanostructure.

A shift in electrochemical reaction rate by analyte-probe binding is widely used22. This shift is predominantly achieved by relocating redox molecules upon target-probe binding23, a location that complicates probe selection and usually implores tedious trial-and-error development. To overcome this hurdle, the DNA nanostructure probe described and demonstrated at least in this Example was designed for consistent redox molecule positioning, with the focus instead on a target-dependent change in tethered-diffusion of the nearby electrochemical label. For this purpose, the MB-DNA label was positioned strategically near the anchor-DNA label. A DNA nanostructure was made with desthiobiotin on the anchor-DNA, with streptavidin as the target protein. First, the DNA nanostructure's current was measured as a blank, then 20 μL of streptavidin was incubated on the electrode. The electrode was rinsed, and current was measured again (FIGS. 9A-9B). We observed a clear drop in the peak height, that can indicate that the tethered diffusion of the redox molecule is slowed by streptavidin binding, akin to an anchor, in simple drop-and-read fashion (FIG. 5A). The calibration curve of streptavidin is shown in FIG. 5B, where concentration dependent signal suppression was observed with an LOD of 5 nM (100 fmol) and a dynamic range of 5 to 500 nM.

Further validation of protein quantification mode was exhibited through direct antibody detection, where anti-digoxigenin antibody served as the anchor on a digoxigenin-modified DNA nanostructure. The same drop-and-read protocol was followed (FIG. 5C), and a decrease in current proportional to concentration of anti-digoxigenin was observed (FIG. 5D). The LOD of the sensor was 2 nM (40 fmol) with dynamic range between 2 and 100 nM. This result also confirmed the versatility of the method, since it was proven functional for two different tags (desthiobiotin or digoxigenin) that targeted two different types of proteins (streptavidin or anti-digoxigenin).

Figures 6A, 6B, 6C, 6D:
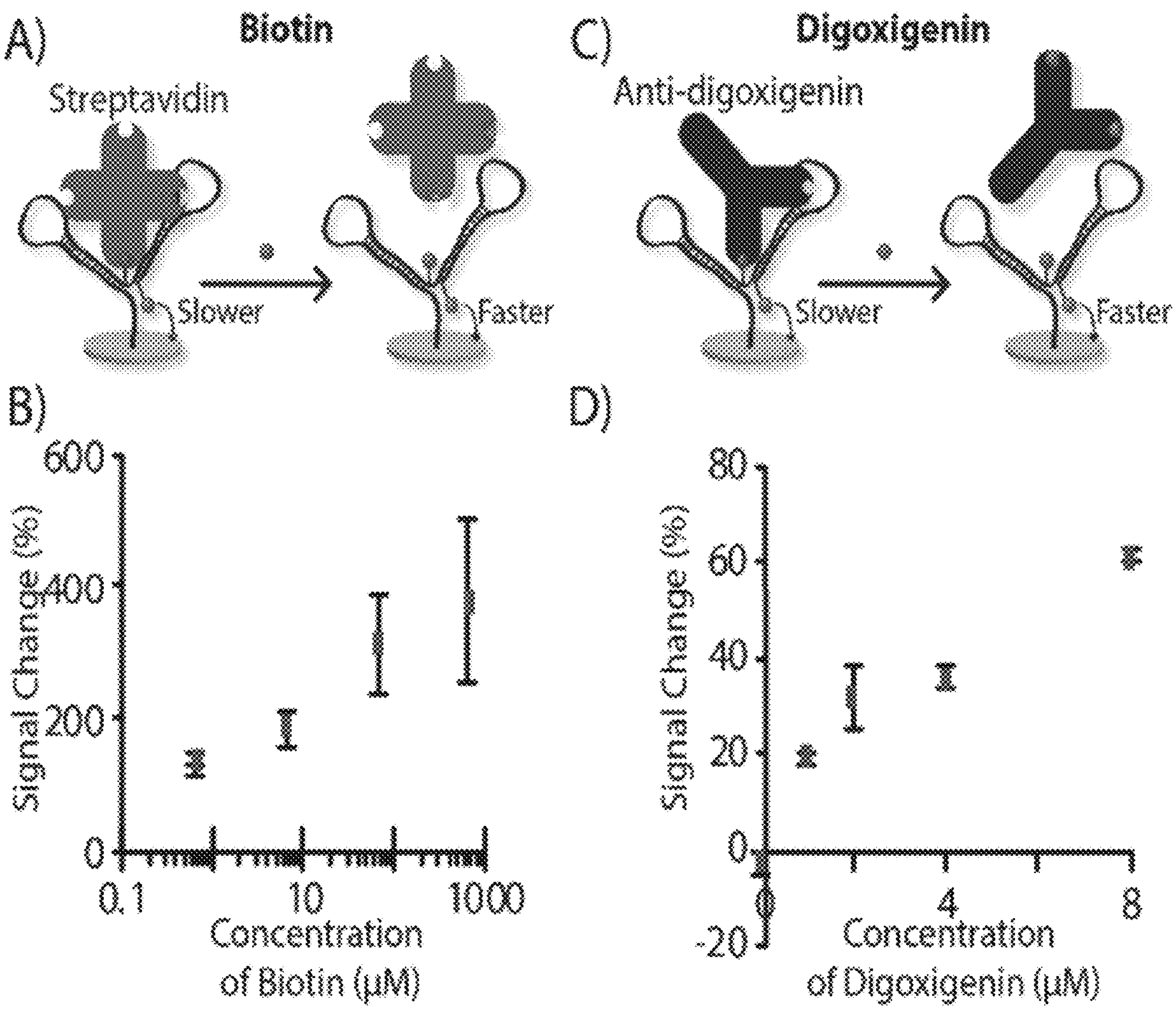
FIGS. 6A-6D show aspects of small molecule quantification mode.

After confirming target-induced decreases in tethered diffusion of the nanostructure, tethered diffusion was increased again by displacing bound proteins (i.e. anchors), giving a small-molecule quantification mode (see e.g. FIG. 3B). The same nanostructures described and demonstrated previously in this Example were employed for indirect quantification of biotin and digoxigenin, respectively. In these cases, the probe included pre-bound streptavidin and anti-digoxigenin (FIGS. 6A and 6C). Streptavidin binds with biotin very strongly (Kd=about 10-15 M), which should effectively displace streptavidin bound to desthiobotin (weaker; Kd=about 10-12 M). This DNA nanostructure was constructed as before using on-electrode ligation, except in this instance the electrode was pre-incubated with streptavidin to slow the tethered diffusion. Using a similar protocol as previously described, biotin caused a concentration-dependent increase in signal (FIG. 6B) with an LOD of 5 μM (100 nmol) and dynamic range of 5 to 50 μM. The same strategy was applied for digoxigenin quantification, with the anti-digoxigenin anchor. FIG. 6D shows the calibration curve of digoxigenin, which exhibited an LOD of 1 μM (20 nmol) and a dynamic range of 1 to 8 μM.

Figure 7:
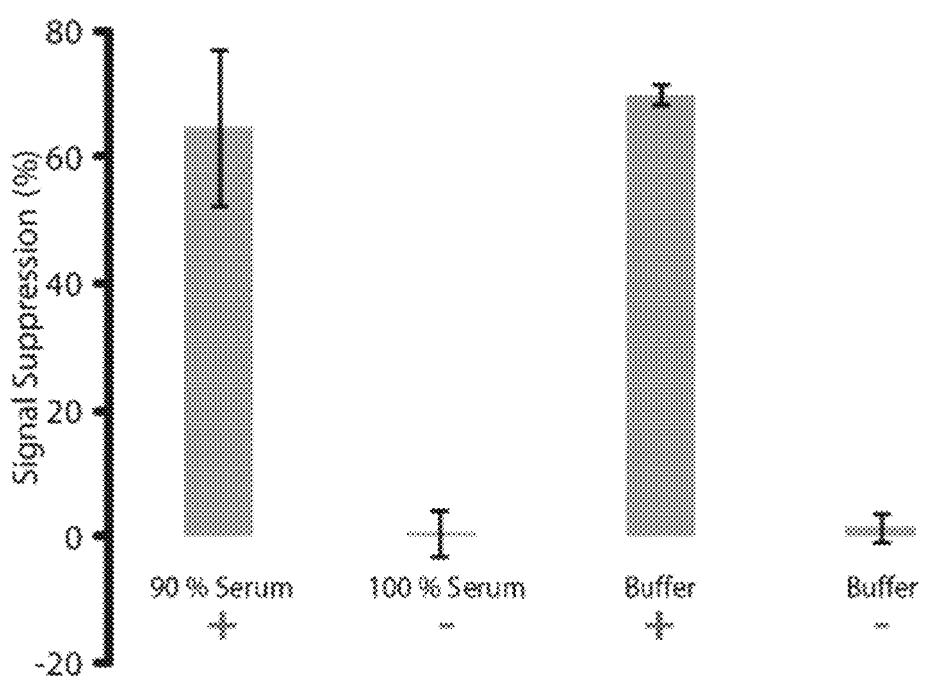
FIG. 7 shows a graph that can demonstrate serum stability of a DNA nanostructure described herein. 100 nM anti-Digoxigenin (+) spiked into undiluted serum (resulting in 90% serum) and in buffer showed similar signal suppression levels. In the absence of anti-digoxigenin (−) the undiluted serum and buffer did not undergo observable signal changes.

This Example can demonstrate at least that the DNA-nanostructure described herein based sensor is versatile, with capability to measure a wide range of targets from small molecules to antibodies through a simple drop-and-read workflow. For an assay to be successful at the point of care (POC), the sensors should be stable in undiluted complex matrices to be helpful at clinical or POC sites lacking expertise. The DNA-nanostructure demonstrated and described herein was used to quantify anti-digoxigenin antibodies spiked into human serum. FIG. 7 shows the signal suppression observed in spiked serum samples (n=2), and the percentage of suppression agreed with results in buffer (both labeled as +). In unspiked serum and buffer, there was no observable change in the SVVV current (both labeled as −). This data can indicate that the DNA-nanostructured described herein is stable in undiluted complex matrices.

This Example can demonstrate at least a DNA-nanostructure and its incorporation into a versatile electrochemical biosensor system. This Example also can demonstrate generation of a stable DNA nanostructure through on-electrode enzymatic ligation. Since DNA can be customized to form a wide variety of different structures via highly selective, programmable hybridization, this production method using T4 DNA ligase at the electrode can allow DNA-nanostructure generation with nanometer precision. This facilitates the production complex probe structures, which can be an advantage of other synthesis techniques. Further, this production approach facilitates economical use of commercially-synthesized DNA to circumvent complex purification procedures. The DNA-nanostructure based system is demonstrated to be a highly versatile assay platform. IT was confirmed that the same core DNA-nanostructure can be used for quantification of streptavidin, anti-digoxigenin, digoxigenin, and biotin. In short, the DNA-nanostructure was demonstrated to be capable of quantifying analytes from small molecules through large antibodies. The modular construction of the DNA-nanostructure provides a simple route to target multiplexing by substituting the anchor-recognizing unit (light gray strand in FIG. 4A), and the stability of the sensor in serum bodes well for future POC applications.

REFERENCES FOR EXAMPLE 1

(1) Turner, A. P. F. Chem. Soc. Rev. 2013, 42 (8), 3184-3196.

(2) Kang, D.; Parolo, C.; Sun, S.; Ogden, N. E.; Dahlquist, F. W.; Plaxco, K. W. ACS Sensors 2018, 3 (7), 1271-1275.

(3) Labib, M.; Sargent, E. H.; Kelley, S. O. Chem. Rev. 2016, 116 (16), 9001-9090.

(4) Schoukroun-Barnes, L. R.; Macazo, F. C.; Gutierrez, B.; Lottermoser, J.; Liu, J.; White, R. J. Annu. Rev. Anal. Chem. 2016, 9 (1), 163-181.

(5) Ferguson, B. S.; Hoggarth, D. A.; Maliniak, D.; Ploense, K.; White, R. J.; Woodward, N.; Hsieh, K.; Bonham, A. J.; Eisenstein, M.; Kippin, T. E.; Plaxco, K. W.; Soh, H. T. Sci. Transl. Med. 2013, 5 (213), 213ra165.

(6) Mage, P. L.; Ferguson, B. S.; Maliniak, D.; Ploense, K. L.; Kippin, T. E.; Soh, H. T. Nat. Biomed. Eng. 2017, 1 (5), 0070.

(7) Arroyo-Currás, N.; Somerson, J.; Vieira, P. A.; Ploense, K. L.; Kippin, T. E.; Plaxco, K. W. Proc. Natl. Acad. Sci. U.S.A. 2017, 114 (4), 645-650.

(8) Mahshid, S. S.; Camiré, S.; Ricci, F.; Vallée-Bélisle, A. J. Am. Chem. Soc. 2015, 137 (50), 15596-15599.

(9) Mahshid, S. S.; Ricci, F.; Kelley, S. O.; Vallée-Bélisle, A. ACS Sensors 2017, 2 (6), 718-723.

(10) Mahshid, S. S.; Vallée-Bélisle, A.; Kelley, S. O. Anal. Chem. 2017, 89 (18), 9751-9757.

(11) Zhou, W.; Mahshid, S. S.; Wang, W.; Vallée-Bélisle, A.; Zandstra, P. W.; Sargent, E. H.; Kelley, S. O. ACS Sensors 2017, 2 (4), 495-500.
(12) Bonham, A. J.; Paden, N. G.; Ricci, F.; Plaxco, K. W. Analyst 2013, 138 (19), 5580-5583.
(13) Cash, K. J.; Ricci, F.; Plaxco, K. W. J. Am. Chem. Soc. 2009, 131 (20), 6955-6957.
(14) Yeung, S. S. W.; Lee, T. M. H.; Hsing, I.-M. J. Am. Chem. Soc 2006, 128 (41), 13374-13375.
(15) Campos, P. P.; Moraes, M. L.; Volpati, D.; Miranda, P. B.; Oliveira, O. N.; Ferreira, M. ACS Appl. Mater. Interfaces 2014, 6 (14), 11657-11664.
(16) Hye Jin Lee; Alastair W. Wark; Yuan Li, and; Corn, R. M. Anal. Chem. 2005, 77 (23), 7832-7837.
(17) Wang, Y.; He, X.; Wang, K.; Ni, X. Biosens. Bioelectron. 2010, 25 (9), 2101-2106.
(18) Zhao, T.; Lin, C.; Yao, Q.; Chen, X. Talanta 2016, 154, 492-497.
(19) Hu, J.; Yu, Y.; Brooks, J. C.; Godwin, L. A.; Somasundaram, S.; Torabinejad, F.; Kim, J.; Shannon, C.; Easley, C. J. J. Am. Chem. Soc. 2014, 136 (23), 8467-8474.
(20) Somasundaram, S.; Holtan, M. D.; Easley, C. J. Anal. Chem. 2018, 90 (5), 3584-3591.
(21) Huang, K.-C.; White, R. J. J. Am. Chem. Soc. 2013, 135 (34), 12808-12817.
(22) White, R. J.; Plaxco, K. W. Anal. Chem. 2010, 82 (1), 73-76.
(23) Lubin, A. A.; Vander Stoep Hunt, B.; White, R. J.; Plaxco, K. W. Anal. Chem. 2009, 81 (6), 2150-2158.

Example 2

Introduction

Figure 15:
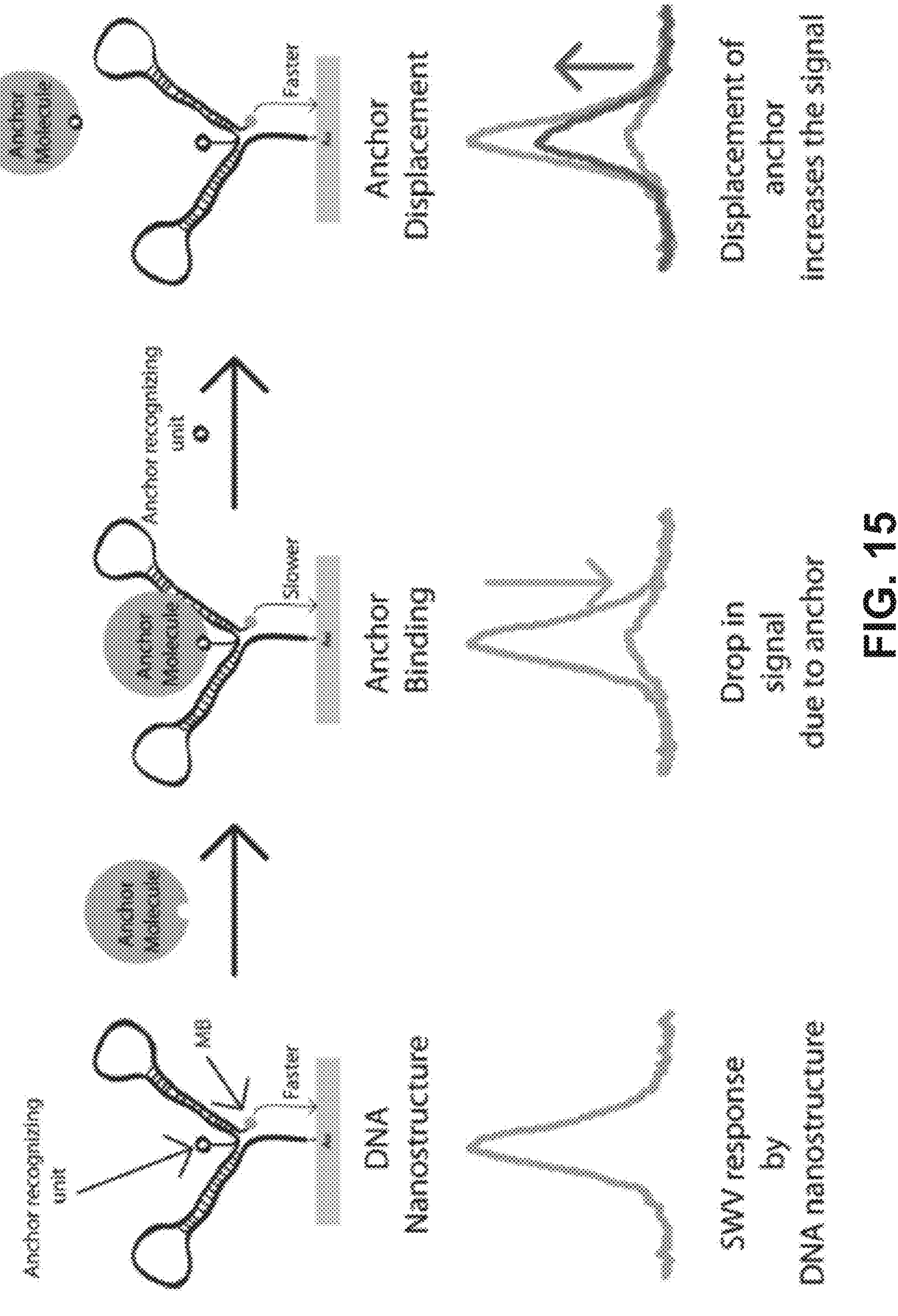
FIG. 15 shows a schematic view of DNA nanostructure anchor model for quantification of small molecules and macromolecules (e.g. a protein or large nucleic acid). The DNA nanostructure can be configured such that the signal moiety (e.g. a redox molecule such as methylene blue) and the anchor recognition unit are in close proximity, so any interaction in anchor recognition unit will affect the diffusion of the redox moiety to the surface. Initially, the diffusion can be faster resulting in high SWV current output.

This Example can demonstrate at least a versatile electrochemical quantification method for a wide range of targets, ranging from small molecules to larger macromolecules (such as a protein or large nucleic acid), which can be suitable for drop-and-read diagnostic and real-time measurements. Based on an understanding about the DNA hybridization on the surface and the distance dependence of SWV signal, a sensing nanostructure was designed that has the redox moiety and anchor recognition in close proximity, more flexible ssDNA between the surface and the redox moiety, and where each sensing nanostructure is a single molecule covalently attached to the electrode (FIG. 15). The premise behind the sensing nanostructure that can be demonstrated in this Example a large anchor molecule is introduced there will be a change in the tethered diffusion rate which slows the complex mobility to the surface, leading to signal suppression. It can also be possible to introduce a competitor, where the anchor molecule is displaced resulting in increased mobility, observed as a signal increase. By this strategy, both anchor (large protein) molecules and small molecule competitors can be quantified. The anchor molecule quantification will be a direct signal-OFF method (signal suppression), and small molecule detection approach will be an indirect signal-ON (signal appreciation) assay. The SWV frequency can be tuned to change the current response direction of the assay (signal-OFF to signal-ON or vice versa). This type of change can also give ratiometric or calibration free results.

Materials and Methods

All solutions were prepared with deionized, ultra-filtered water (Fisher Scientific). The following reagents were used as received: 4-(2-hydroxyethyl)-1-piperazineethanesulfonic acid (HEPES) and Sodium perchlorate from Alfa Aesar. Anti-digoxigenin, digoxigenin, tris-(2-carboxyethyl) phosphine hydrochloride (TCEP), mercapto hexanol, gold etchant, and chromium etchant from Sigma-Aldrich. Gold-sputtered on glass (GoG) (Au 100 nm with Cr adhesion layer 5 nm) from Deposition Research Lab, Inc (St. Charles, Mo.) with dimension 1×3×1.1 mm. AZ 40XT (positive thick photoresist) and AZ 300 MIF developer from Microchemicals, polydimethylsiloxane (PDMS) from Dow Corning Corp, and dimethyl sulfoxide (DMSO) from anachemia. Methylene blue-conjugated DNA was purchased from Biosearch Technologies (Novato, Calif.), purified by RP-HPLC. Thiolated DNAs were obtained from Integrated DNA Technologies (IDT; Coralville, Iowa), with purity confirmed by mass spectroscopy, T4 DNA ligase (400000 units) and adenosine triphosphate (ATP, 10 mM) are bought from New England Bio, DNAs are listed in Table 4.

TABLE 4

Sequence of DNAs used in anchor model quantification (Example 4)

| SEQ ID NO: | Sequence Name | Abbreviation | DNA Sequence 5' → 3' |
|---|---|---|---|
| 17 | Anchor 4A thiolated DNA | anc4A-DNA | /**5Phos**/ CTG TGC AAG AAC TCA CAG CCT CAC CTC TTC CTA AAA A /**3ThioMC3-D**/ |
| 18 | Anchor 6A thiolated DNA | anc6A-DNAv | /**5Phos**/ CTG TGC AAG AAC TCA CAG CCT CAC CTC TTC CTA AAA AAA /**3ThioMC3-D**/ |
| 19 | Anchor 8A thiolated DNA | anc8A-DNA | /**5Phos**/ CTG TGC AAG AAC TCA CAG CCT CAC CTC TTC CTA AAA AAA AA /**3ThioMC3-D**/ |
| 20 | Anchor 10A thiolated DNA | anc10A-DNA | /**5Phos**/ CTG TGC AAG AAC TCA CAG CCT CAC CTC TTC CTA AAA AAA AAA A /**3ThioMC3-D**/ |
| 21 | Anchor connector desthiobiotin | conn-biotin | /**5Phos**/ GAG ACA CTG TGT CGT CTC CGG TTG MAG TGG AGA /**ideSBioTEG**/ TAG GAA GAG GTG AGG |

TABLE 4-continued

Sequence of DNAs used in anchor model quantification (Example 4)

| SEQ ID NO: | Sequence Name | Abbreviation | DNA Sequence 5' → 3' |
|---|---|---|---|
| 22 | Anchor connector digoxigenin | conn-digoxi | **/5Phos/** GGG CGA CTG TGT CCG CCC cGG TtG AAG TOG AGA **/iDigN/** TAG GAA GAG GTG AGG |
| 23 | Anchor Methylene Blue DNA | MB-DNA | **/dT MB/** CTC CAC TTC AAC CG |

/5phos/ = Phosphorylation (IDT),
/3ThioMC3-D/ = Dithiol attachment (IDT),
/ideSBioTEG/ = Interme-diate Desthiobiotin-TEG (IDT),
/iDigN/ = Intermediate Digoxigenin (IDT),
/dT MB/ = Methylene Blue on T-C3 (Biosearch)

Electrode Preparation and DNA SAM.

A photomask of electrode design used in the experiment. Each electrode was 2 mm diameter and it was designed in a way that each electrochemical cell will have single electrode. The geometrical surface area of the electrode was increased to have a high initial signal. Same photolithography protocol explained in Example 3 was followed to prepare GoG. The PDMS electrochemical cell was prepared with 3D-CAD and PLA mold. Following this, thiolated SAM was prepared, with HEPES buffer (10 mM with MgCl2 10 mM, pH 7). Briefly, Thiol tagged DNA were shipped as disulfides, thus they required chemical reduction by dithiothreitol or TCEP. We used TCEP for reduction, where 1 μL of 200 μM thio-DNA and 3 μL of 10 mM TCEP were mixed in a 200 μL PCR tube and placed in the dark for 1 hour at room temperature. The solution was then diluted with HEPES buffer (10 mM HEPES and 0.5 M NaClO4, pH 7.0) to a concentration of 1.25 μM and a volume of 300 μL for an electrode in a 15 mL shell vial. The electrode was dipped in this solution (making sure the electrode was not hitting the surface) and incubated at room temperature for another 1 hour in the dark (for some experiments a 16-hour incubation was used). After 1 hour of incubation, the electrode was removed and rinsed with deionized water for 30 seconds (water should be carefully passed on the side and flown over the gold area; no forceful ejection of water should be applied to the gold). Then the electrode was dipped into 300 μL of 3 mM MCH for 1 hour in the dark at room temperature. The MCH solution should be freshly prepared, and since MCH has a foul smell, it is advised to do all these processes in a fume hood. MCH acts as a spacer molecule between covalently bounded thio-DNA, which is helpful in reducing the capacitance current in electrochemical measurements. In addition to that, it also helps to remove non-specific binding between DNA or proteins and the gold surface, and it contributes toward effective orientation of the thio-DNAs on the electrode surface. Once this incubation was done, the electrode was rinsed with deionized water and transferred to HEPES buffer. This SAM electrode was ready to be used and could be stored at 4° C. for about a week.

On-Electrode DNA Nanostructure Assembly Using Through T4 DNA Ligase.

As the efficiency of the T4 DNA ligase enzyme is hindered by sodium ion concentration, ligation reactions at the electrode surfaces were carried out in HEPES buffer with no sodium salt added. To improve the DNA binding energy, 10 mM MgCl2 was used. After ligation, the typical HEPES buffer (10 mM HEPES, 0.5 M NaClO4) was used. Once the electrode was ready, 500 nM of anchor connector DNA and anchor MB-DNA was prepared in HEPES buffer (10 mM HEPES, 10 mM MgCl2, 1 mM ATP, pH 7). In each well, 200 μL of this mix was introduced into the electrode, following this 0.5 μl of 400,000 Units T4 DNA ligase was dropped into the electrochemical cell, wrapped in Parafilm and incubated overnight at room temperature. Then the electrode was briefly rinsed with water (deionized water drop was pipetted up and down twice and removed), HEPES (10 mM HEPES and 0.5 M NaClO4) was introduced, and the electrode was ready to use.

Electrochemical Measurement.

Electrochemical measurements were performed using a Gamry Reference 600 potentiostat, in a three-electrode system setup with the platinum counter electrode (CH instruments) and silver/silver chloride (3 M KCl) reference electrode (BASi). Table 5 gives the SWV parameters used.

TABLE 5

SWV parameters for single Branched DNA quantification study (Example 4)

| Parameter | Symbol | Values Used |
|---|---|---|
| Initial Voltage | $V_I$ | −0.425 V |
| Final Voltage | $V_r$ | −0.05 V |
| Step size | $E_s$ | 1 mV |
| Puise height | $E_p$ | 50 mV |
| Frequency | SWV-Hz | 4 to 900 Hz |

Data Analysis—Baseline Correction and Peak Height.

procedure for baseline correction and peak height was used. Briefly, each set of raw data from square-wave voltametry (including Vstep and |cliff) was transferred to Microsoft Excel, and a nineteen-point moving average was applied to reduce environmental noise. Following this, a third-order polynomial baseline was calculated near the redox potential of MB-DNA. To do this, the Linest equation in Excel was used, and data points from −0.400 V to −0.370 V and −0.15 V to −0.09 V were selected for baseline fitting. The resultant base-line function was subtracted from the 19-point averaged data to get a baseline corrected SWV voltammagram. The maximum current from this graph was used as the peak height of each particular run. Signal-to-background differences and ratios were also calculated using peak heights obtained in this way. To get the signal to background difference, the peak height value of the background was subtracted from the signal of same n, temperature, and frequency. In a similar way to get the signal to background ration, the background was divided.

Data Analysis-Signal Change Percentage.

For signal off quantification signal percentage change was used. This was the percentage of signal depressed by the target. Equation 3 was used for the calculation, where ipsignal and ipbackground were peak height after and before target incubation respectively.

$$\% \text{ change} = \left(\frac{i_p \text{ signal} - i_p \text{ background}}{i_p \text{ background}}\right) \times 100 \quad \text{(Eq. 3)}$$

Quantification Protocol-Streptavidin Quantification.

For streptavidin quantification, the DNA nanostructure was made by anc4A-DNA, conn-biotin, and MB-DNA. Once the electrodes were ready background measurement were done by SVVV with 100 Hz frequency in 100 μl of HEPES (10 mM HEPES, 0.5 M NaClO4, pH 7). Followed by target was incubated for 2 hours, then the same electrochemical measurement was done.

Quantification Protocol-Biotin Quantification.

Once the nanostructured is formed on the electrode anc4A-DNA, conn-biotin, and MB-DNA, the electrode was introduced to 100 μL of 2 μM streptavidin in HEPES buffer and incubated for 2 hours at room temperature. Then the electrodes were rinsed with buffer and background measurements were done by SWV with 100 Hz frequency. Finally, 100 μl of target was incubated for 2 hours, then the same electrochemical measurement was done.

Results.

DNA Monolayer Formation and its Stability.

An objective of this Example was to demonstrate that the diffusional change by the molecular weight of the binding partner of the nanostructures describe herein can be exploited for quantification. To achieve this, three moieties were attached to the DNA nanostructure: 1) the thiolated tag for attaching the DNA to the gold electrode, 2) redox moiety for electrochemical signal and 3) anchor recognizing moiety. In addition to this, for an effective signal change, the redox moiety was placed in close proximity to the anchor recognizing moiety. Instead of purchasing custom made DNA with three tags, which would be very expensive even with low reaction yield the nanostructures were constructed utilizing T4 DNA ligase enzyme. In short, three single-strand DNA sequences were ligated to form a DNA nanostructure on the surface of an electrode. T4 DNA ligase can only ligate phosphorylated 5' double stranded DNA with 3'. To avoid more complexity, instead of using connectors for making double stranded DNA, hairpin structures were used to form suitable ligation structures. Previously, the dithiol tag for thiolated DNA were done at the 5' end. For ligation reaction demonstrated in at least this Example, thiolated-DNA with 3' dithiol tags.

FIGS. 8A-8B shows the pictorial description of the DNA nanostructure. On addition of anchor-connecter and MB-DNA to the SAM electrode, hybridization occurs as shown in FIG. 8B. The anchor connector binds with thiolated-DNA, and MB-DNA binds with anchor connector; both bind with 15 bp, which is a strong binding energy at room temperature. There is no hybridization reaction between MB-DNA and thiolated DNA, which eliminates the false signal in the background, methylene blue with anchor recognizing unit. When T4 DNA ligase is added with ATP, the enzyme effective ligates the two positions on the surface and makes it a single DNA complex with three tags. One other advantage is that the method can be quickly extended to other targets just by changing the DNA with anchor recognizing unit.

To support that by ligation single DNA is formed, we compared the ligated and non-ligated complex signal. First the electrodes are rinsed with buffer (HEPES 10 mM, with 0.5 M NaClO4, pH 7). On comparison the signal between the ligated and non-ligated are similar (FIG. 4C). The hybridization energy with 0.5 M NaClO4 is very stable, which results in similar signal. Then the electrodes were rinsed with deionized water. On measurement after this rinse shows that the non-ligated complex is almost fully removed in just one water rinse cycle. On cycling this process for two more time, we see that ligated DNA is stable on the surface, which shows that is a single DNA covalently bound on the surface of the gold electrode. As an additional confirmation of DNA nanostructure stability and effective DNA ligation, DNA melt study is done, with sybr-green florescent intercalation dye. FIG. 4B compares derivative curve of non-ligated and ligated DNA. The peak temperature represents the melt-temperature. The Tm temperature of non-ligated is around 55° C., whereas the ligated complex is stable until 75° C.

DNA Nanostructure Signal Suppression by High Molecular Weight Anchor.

Once the formation of DNA nanostructure by T4 DNA ligation on the electrode surface and its stability confirmed, the signal suppression by a molecular anchor was tested. Signal suppression can be due to the slowing down of the complex diffusion. So, the complex, specifically the redox moiety, can be diffusion limited and devoid of other interactions (double layer) which hinders hybridization. A thiolated-DNA was generated, which placed the redox moiety at a distance of 4 to 10 (4 A, 6 A, 8 A, and 10 A) nucleotides from the electrode surface. Longer distances were not used because the signal would be minimal due to distance dependence. FIGS. 13A-13D shows the comparison of signal suppression by binding streptavidin (1 μM) to the nanostructure with 4 A, 6 A, 8 A, and 10 A spacers. As expected, the DNA nanostructure signal dropped as the redox moiety was placed far from the surface due to distance dependence. But the signal comparison between the four complexes after streptavidin was attached showed a similar response. The effects of distance were assumed to be less pronounced due to the large protein attachment. To select a complex for quantification, the signal suppression was compared. The 4 A complex underwent a larger signal suppression by streptavidin (or generally larger molecule), which can be the most sensitive among the four complexes analyzed here. For a small molecule competitor assay, a complex which can result in more signal gain is the suitable one. From the comparison, since 4 A undergoes a large signal suppression, it can result in higher signal gain in displacement of an anchor molecule.

Streptavidin and Biotin.

Streptavidin and biotin were chosen to demonstrate the applicability and versatility of the DNA nanostructure sensing system described herein for the following reasons: 1) They have the strongest known non-covalent binding (Kd=10-15 M), 2) streptavidin is a large protein molecule with 52.8 kDa, and biotin is a small molecule with 244.3 Da. Desthiobiotin was used as an anchor recognition unit in the connector DNA. Desthiobiotin is a biotin analogue which can bind with biotin-binding protein with lower affinity, i.e.

higher Kd (10-12M), compared to biotin, so the protein can be displaced by biotin effectively (Hirsch et al. Anal. Biochem. 308(2): 343-357, 2002). FIGS. 5A and 6A shows the sensor response to different concentration of streptavidin, where we observed a dynamic range of 5 to 500 nM. By this data, streptavidin protein is directly measured by a signal-OFF amplification free electrochemical assay. Other than quantification of streptavidin, two more things are noted: 1) Higher concentration of streptavidin suppressed about 80% of the signal, 2) the signal alteration by blank is very minimal. Together, this shows that the DNA nanostructure with the streptavidin can be used as a sensor for quantification of biotin. FIGS. 5A, 5B, 6A, and 6B shows the biotin quantification model and sensor response with different concentration of biotin. A good but narrow response to biotin (dynamic range is 5 to 50 μM) was observed. This data can demonstrate that the anchor model can also be used for quantification of small molecules by an indirect, signal-ON assay. The streptavidin assay was observed to be very sensitive. This sensitivity can be due to the four binding sites available in streptavidin. This multivalence nature helps streptavidin to bind effectively to the surface. In addition to this there is a need for excess biotin to compete and displace the streptavidin. This Example can also demonstrate that the same DNA nanostructure to be useful for detecting both larger proteins and small molecules.

Anti-Digoxigenin and Digoxigenin.

Figure 14A:
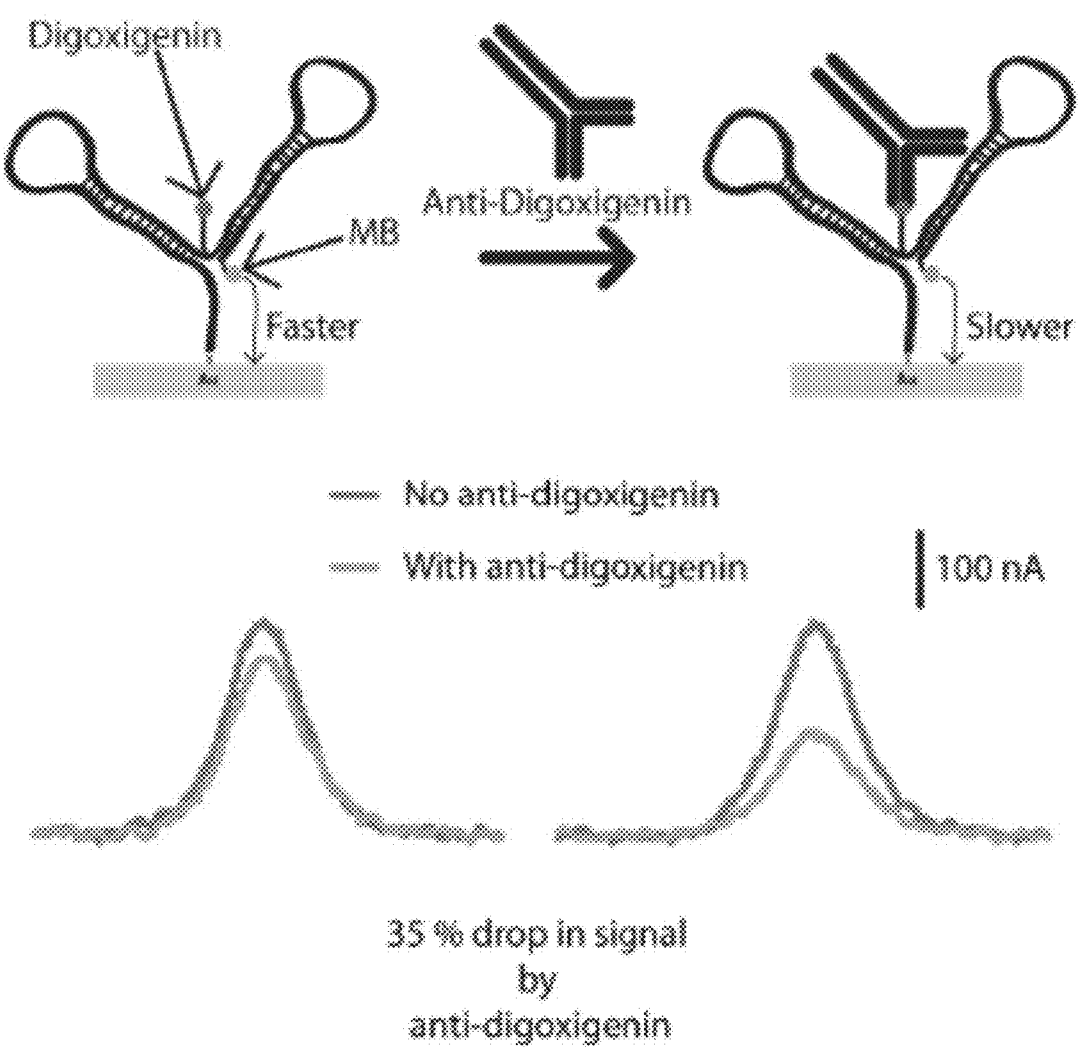
FIGS. 14A-14B can demonstrate anti-digoxigenin and digoxigenin detection via a DNA-nanostructure described herein. Anti-digoxigenin and digoxigenin can be detected as shown in FIGS. 14A-14B. The sensor shows a good response to the target with 35% signal suppression by anti-digoxigenin anchor and about 37% signal appreciation by digoxigenin.
Figure 14B:
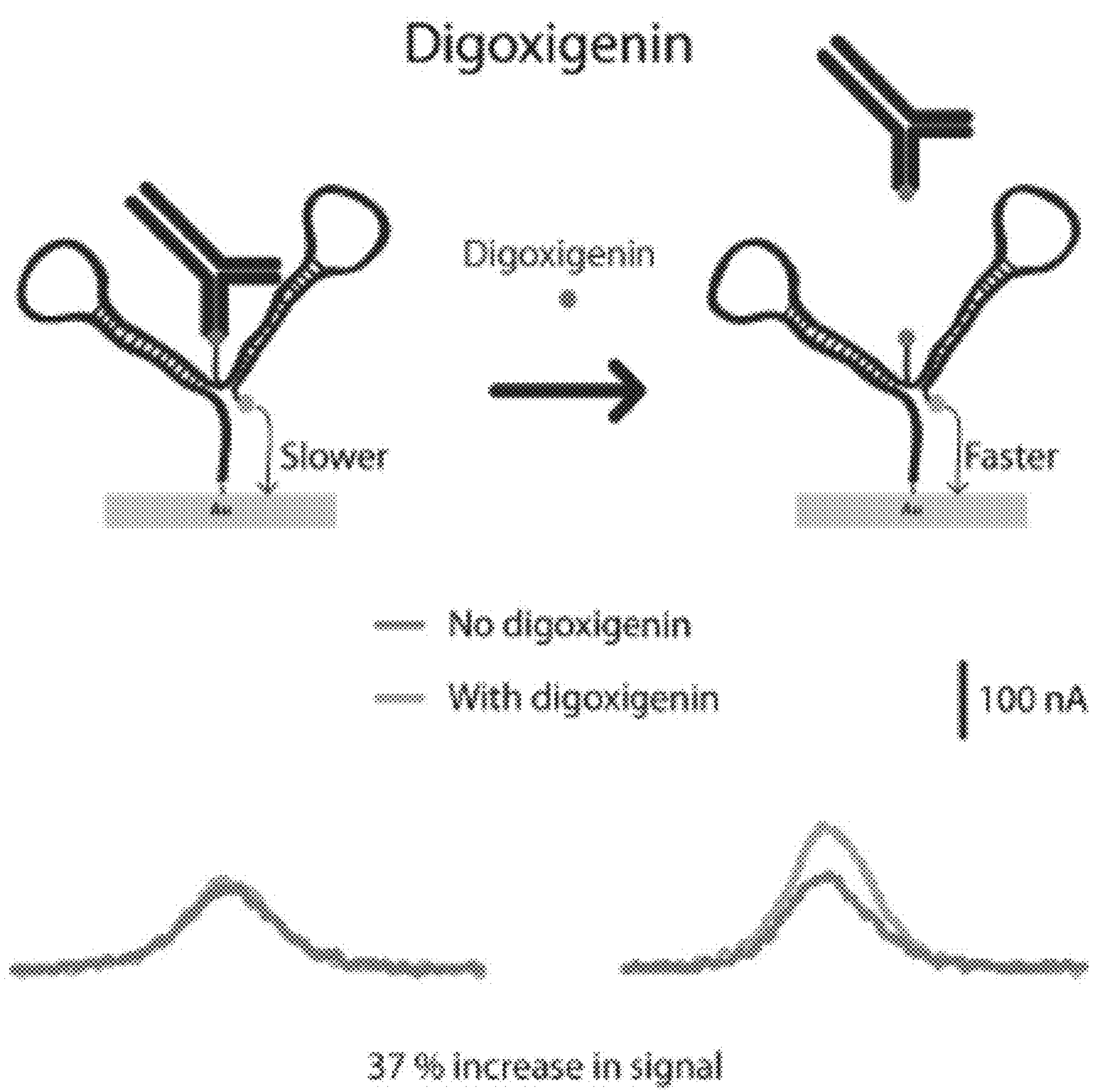

To further test the generalizability of the DNA nanostructure system, assay and system was operated with anti-digoxigenin antibodies and digoxigenin. The digoxigenin is used as an anchor recognition unit in connector-DNA. The same thiolated-DNA (anc4A-DNA) and MB-DNA were used, result of DNA nanostructure formation by T4 ligation enzyme. FIGS. 14A-14B show the signal response for both anti-digoxigenin antibody and digoxigenin. On introduction of anti-digoxigenin antibody to the DNA nanostructure, a 35% signal suppression was observed. This is not seen in the absence of target. Similar results were observed with digoxigenin, where the digoxigenin displaces the antibody resulting in a 37% signal increase. This proves that the DNA nanostructure anchor model can be extended for quantification of both small molecules and large protein binding partners such as antibodies. As a development in this quantification, we assume that the binding energy of the anti-digoxigenin is lower, resulting in lower signal suppression. This affected the sensitivity in digoxigenin quantification.

SUMMARY

This Example can demonstrate a versatile quantification strategy for large proteins and small molecules. This Example can demonstrate quantification of streptavidin and biotin, as a direct and indirect assay. Conventional gold standard methods like ELISA needs dual antibody system for effective quantification, and at present electrochemical sensors require conformational changing aptamers. This Example at least can demonstrate a sensor which uses a single antibody and ignores conformational change of binding partners such as aptamers. This is supported by the results with digoxigenin herein, in which the sensor responded to both antibody and small molecule. Perhaps the most exciting feature is that the sensor is drop-and-read, and no reagents or enzymes are used for amplification, which simplifies the advancement of this method for a possible POC assay.

What is claimed is:

1. A method for detecting an analyte, the method comprising:

contacting a sample containing the analyte to an anchor recognition moiety coupled to a DNA nanostructure, wherein the DNA nanostructure comprises:

a single continuous DNA molecule comprising: a first hairpin structural motif, a second hairpin structural motif, a first segment of single stranded DNA, and a second segment of single stranded DNA, wherein the first hairpin structural motif and the second hairpin structural motif are attached to each other via the first segment of single stranded DNA, wherein the second segment of single stranded DNA is attached to the second hairpin structural motif such that the second segment of single stranded DNA forms a single stranded tether region at one end of the single continuous DNA molecule;

the anchor recognition moiety, wherein the anchor recognition moiety is covalently coupled to a region of the single continuous DNA molecule between the first hairpin structural motif and the second hairpin structural motif; and a signal moiety coupled to an end of the single continuous DNA molecule opposite from the tether region, wherein the signal moiety and the anchor recognition moiety on the single continuous DNA molecule are in effective proximity to each other such that binding of the analyte to the anchor recognition moiety changes a tethered diffusion rate of the signal moiety, wherein a terminal base of the second segment of single stranded DNA of the DNA nanostructure is coupled to a surface of an electrode; and detecting a change in the tethered diffusion rate of the signal moiety relative to the surface of the electrode when the analyte binds to the anchor recognition moiety wherein said detecting the change in the tethered diffusion rate of the signal moiety comprises detecting a change in an electrochemical current at the surface of the electrode.

2. The method of claim 1, further comprising binding the analyte to the anchor recognition moiety.

3. The method of claim 1, further comprising assembling the DNA nanostructure on the electrode.

4. The method of claim 3, wherein said assembling the DNA nanostructure on the electrode comprises immobilizing a thio-DNA comprising the second hairpin structural motif and the second segment of single stranded DNA to the surface of the electrode by the terminal base of the second segment of single stranded DNA, ligating an anchor recognition unit comprising the anchor recognition moiety, the first segment of single stranded DNA and the first hairpin structural motif to the second hairpin structural motif such that the second segment of single stranded DNA is attached to one end of the second hairpin structural motif, and the first segment of single stranded DNA is attached to other end of the second hairpin structural motif and one end of the first hairpin structural motif, and ligating a third segment of single stranded DNA coupled to the signal moiety to other end of the first hairpin structural motif of the anchor recognition unit.

5. The method of claim 1, wherein the DNA nanostructure further comprises a linker having a reactive group capable of attaching to the surface of the electrode, wherein the linker is attached to the terminal base of the second segment of single stranded DNA.

6. The method of claim 5, wherein the reactive group is selected from the group consisting of: a carboxyl group, amino group, aromatic amine group, a chloromethyl group, an amide group, a hydrazide group, a hydroxyl group, a thiol group, an epoxy group, and combinations thereof.

7. The method of claim 1, wherein the single continuous DNA molecule has a sequence that is 1-100% identical to one of SEQ ID NOs: 7-8.

8. The method of claim 1, wherein the signal moiety is a redox molecule.

9. The method of claim 1, wherein the signal moiety is methylene blue.

10. A method for detecting an analyte, the method comprising:

contacting a sample containing the analyte to an anchor recognition moiety coupled to a DNA nanostructure, wherein the DNA nanostructure comprises:

a single continuous DNA molecule comprising: a first hairpin structural motif, a second hairpin structural motif, a first segment of single stranded DNA, and a second segment of single stranded DNA, wherein the first hairpin structural motif and the second hairpin structural motif are attached to each other via the first segment of single stranded DNA, wherein the second segment of single stranded DNA is attached to the second hairpin structural motif such that the second segment of single stranded DNA forms a single-stranded tether region at one end of the single continuous DNA molecule;

the anchor recognition moiety, wherein the anchor recognition moiety is covalently coupled to the single continuous DNA molecule and extends from the single continuous DNA molecule; and a signal moiety coupled to an end of the single continuous DNA molecule opposite from the tether region, wherein the signal moiety and the anchor recognition moiety on the single continuous DNA molecule are in effective proximity to each other such that binding of the analyte to the anchor recognition moiety changes a tethered diffusion rate of the signal moiety, wherein a terminal base of the second segment of single stranded DNA of the DNA nanostructure is coupled to the surface of the electrode; and detecting a change in the tethered diffusion rate of the signal moiety relative to the surface of the electrode when the analyte binds to the anchor recognition moiety wherein said detecting the change in the tethered diffusion rate of the signal moiety comprises detecting the change in an electrochemical current at the surface of the electrode.

11. The method of claim 10, further comprising binding the analyte to the anchor recognition moiety.

12. The method of claim 10, further comprising assembling the DNA nanostructure on the electrode.

13. The method of claim 10, wherein the DNA nanostructure further comprises a linker having a reactive group capable of attaching to the surface of the electrode, wherein the linker is attached to the terminal base of the second segment of single stranded DNA.

14. The method of claim 13, wherein the reactive group is selected from the group consisting of: a carboxyl group, amino group, aromatic amine group, a chloromethyl group, an amide group, a hydrazide group, a hydroxyl group, a thiol group, an epoxy group, and combinations thereof.

15. The method of claim 10, wherein the signal moiety is a redox molecule.

16. A method for detecting an analyte, the method comprising:

contacting a sample containing the analyte to an anchor recognition moiety coupled to a DNA nanostructure, wherein the DNA nanostructure comprises:

a single continuous DNA molecule comprising: a first hairpin structural motif, a second hairpin structural motif, a first segment of single stranded DNA, and a second segment of single stranded DNA, wherein the first hairpin structural motif and the second hairpin structural motif are attached to each other via the first segment of single stranded DNA, wherein the second segment of single stranded DNA is attached to the second hairpin structural motif such that the second segment of single stranded DNA forms a single-stranded tether region at one end of the single continuous DNA molecule;

the anchor recognition moiety, wherein the anchor recognition moiety is covalently coupled to the single continuous DNA molecule and extends from the single continuous DNA molecule; and a signal moiety, wherein the signal moiety is coupled to an end of the single continuous DNA molecule opposite from the tether region, wherein the signal moiety and the anchor recognition moiety on the single continuous DNA molecule is in effective proximity to each other, wherein the DNA nanostructure is coupled to the surface of the electrode by a terminal base of the second segment of single stranded DNA of the DNA nanostructure such that binding of the analyte to the anchor recognition moiety changes a tethered diffusion rate of the signal moiety and a change in the tethered diffusion rate of the signal moiety changes an electrochemical current at the surface of the electrode; and detecting a change in the tethered diffusion rate of the signal moiety relative to the surface of the electrode when the analyte binds to the anchor recognition moiety wherein said detecting the change in the tethered diffusion rate of the signal moiety comprises detecting the change in an electrochemical current at the surface of the electrode.

* * * * *

SEQUENCE LISTING

```
Sequence total quantity: 30
SEQ ID NO: 1            moltype = DNA  length = 33
FEATURE                 Location/Qualifiers
source                  1..33
                        mol_type = other DNA
                        organism = synthetic construct
SEQUENCE: 1
atataggtta cggtatattc attcattctc tcc                              33

SEQ ID NO: 2            moltype = DNA  length = 48
FEATURE                 Location/Qualifiers
source                  1..48
                        mol_type = other DNA
                        organism = synthetic construct
SEQUENCE: 2
ttactgacaa cagagtaaga agtgaagtgt gaaggagaga atgaatga              48

SEQ ID NO: 3            moltype = DNA  length = 20
FEATURE                 Location/Qualifiers
source                  1..20
                        mol_type = other DNA
                        organism = synthetic construct
SEQUENCE: 3
cacagcctca cctcttccta                                             20

SEQ ID NO: 4            moltype = DNA  length = 20
FEATURE                 Location/Qualifiers
source                  1..20
                        mol_type = other DNA
                        organism = synthetic construct
SEQUENCE: 4
taggaagagg tgaggctgtg                                             20

SEQ ID NO: 5            moltype = DNA  length = 20
FEATURE                 Location/Qualifiers
source                  1..20
```

-continued

```
                        mol_type = other DNA
                        organism = synthetic construct
SEQUENCE: 5
tctccacttc aaccggagac                                                20

SEQ ID NO: 6            moltype = DNA  length = 20
FEATURE                 Location/Qualifiers
source                  1..20
                        mol_type = other DNA
                        organism = synthetic construct
SEQUENCE: 6
gtctccggtt gaagtggaga                                                20

SEQ ID NO: 7            moltype = DNA  length = 100
FEATURE                 Location/Qualifiers
source                  1..100
                        mol_type = other DNA
                        organism = synthetic construct
SEQUENCE: 7
tctccacttc aaccggagac actgtgtcgt ctccggttga agtggagata ggaagaggtg  60
aggctgtgca agaactcaca gcctcacctc ttcctaaaaa                          100

SEQ ID NO: 8            moltype = DNA  length = 100
FEATURE                 Location/Qualifiers
source                  1..100
                        mol_type = other DNA
                        organism = synthetic construct
SEQUENCE: 8
tctccacttc aaccggggcg actgtgtccg ccccggttga agtggagata ggaagaggtg  60
aggctgtgca agaactcaca gcctcacctc ttcctaaaaa                          100

SEQ ID NO: 9            moltype = DNA  length = 37
FEATURE                 Location/Qualifiers
source                  1..37
                        mol_type = other DNA
                        organism = synthetic construct
SEQUENCE: 9
ctgtgcaaga actcacagcc tcacctcttc ctaaaaa                             37

SEQ ID NO: 10           moltype = DNA  length = 48
FEATURE                 Location/Qualifiers
source                  1..48
                        mol_type = other DNA
                        organism = synthetic construct
SEQUENCE: 10
gagacactgt gtcgtctccg gttgaagtgg agataggaag aggtgagg                 48

SEQ ID NO: 11           moltype = DNA  length = 48
FEATURE                 Location/Qualifiers
source                  1..48
                        mol_type = other DNA
                        organism = synthetic construct
SEQUENCE: 11
gggcgactgt gtccgccccg gttgaagtgg agataggaag aggtgagg                 48

SEQ ID NO: 12           moltype = DNA  length = 15
FEATURE                 Location/Qualifiers
source                  1..15
                        mol_type = other DNA
                        organism = synthetic construct
SEQUENCE: 12
tctccacttc aaccg                                                     15

SEQ ID NO: 13           moltype = DNA  length = 37
FEATURE                 Location/Qualifiers
source                  1..37
                        mol_type = other DNA
                        organism = synthetic construct
SEQUENCE: 13
ctgtgcaaga actcacagcc tcacctcttc ctaaaaa                             37

SEQ ID NO: 14           moltype = DNA  length = 48
FEATURE                 Location/Qualifiers
source                  1..48
                        mol_type = other DNA
                        organism = synthetic construct
SEQUENCE: 14
gagacactgt gtcgtctccg gttgaagtgg agataggaag aggtgagg                 48
```

-continued

```
SEQ ID NO: 15          moltype = DNA  length = 48
FEATURE                Location/Qualifiers
source                 1..48
                       mol_type = other DNA
                       organism = synthetic construct
SEQUENCE: 15
gggcgactgt gtccgccccg gttgaagtgg agataggaag aggtgagg              48

SEQ ID NO: 16          moltype = DNA  length = 14
FEATURE                Location/Qualifiers
source                 1..14
                       mol_type = other DNA
                       organism = synthetic construct
SEQUENCE: 16
ctccacttca accg                                                   14

SEQ ID NO: 17          moltype = DNA  length = 37
FEATURE                Location/Qualifiers
source                 1..37
                       mol_type = other DNA
                       organism = synthetic construct
SEQUENCE: 17
ctgtgcaaga actcacagcc tcacctcttc ctaaaaa                          37

SEQ ID NO: 18          moltype = DNA  length = 39
FEATURE                Location/Qualifiers
source                 1..39
                       mol_type = other DNA
                       organism = synthetic construct
SEQUENCE: 18
ctgtgcaaga actcacagcc tcacctcttc ctaaaaaaa                        39

SEQ ID NO: 19          moltype = DNA  length = 41
FEATURE                Location/Qualifiers
source                 1..41
                       mol_type = other DNA
                       organism = synthetic construct
SEQUENCE: 19
ctgtgcaaga actcacagcc tcacctcttc ctaaaaaaaa a                     41

SEQ ID NO: 20          moltype = DNA  length = 43
FEATURE                Location/Qualifiers
source                 1..43
                       mol_type = other DNA
                       organism = synthetic construct
SEQUENCE: 20
ctgtgcaaga actcacagcc tcacctcttc ctaaaaaaaa aaa                   43

SEQ ID NO: 21          moltype = DNA  length = 48
FEATURE                Location/Qualifiers
source                 1..48
                       mol_type = other DNA
                       organism = synthetic construct
SEQUENCE: 21
gagacactgt gtcgtctccg gttgaagtgg agataggaag aggtgagg              48

SEQ ID NO: 22          moltype = DNA  length = 48
FEATURE                Location/Qualifiers
source                 1..48
                       mol_type = other DNA
                       organism = synthetic construct
SEQUENCE: 22
gggcgactgt gtccgccccg gttgaagtgg agataggaag aggtgagg              48

SEQ ID NO: 23          moltype = DNA  length = 14
FEATURE                Location/Qualifiers
source                 1..14
                       mol_type = other DNA
                       organism = synthetic construct
SEQUENCE: 23
ctccacttca accg                                                   14

SEQ ID NO: 24          moltype = DNA  length = 15
FEATURE                Location/Qualifiers
source                 1..15
                       mol_type = other DNA
                       organism = synthetic construct
SEQUENCE: 24
tgaggtgtgg aggta                                                  15
```

-continued

```
SEQ ID NO: 25           moltype = DNA  length = 33
FEATURE                 Location/Qualifiers
source                  1..33
                        mol_type = other DNA
                        organism = synthetic construct
SEQUENCE: 25
tatatgttgg atgatataag gaggaaggtg gtg                        33

SEQ ID NO: 26           moltype = DNA  length = 48
FEATURE                 Location/Qualifiers
source                  1..48
                        mol_type = other DNA
                        organism = synthetic construct
SEQUENCE: 26
ttaatggcct aagattaata cctccacacc tcacaccacc ttcctcct        48

SEQ ID NO: 27           moltype = DNA  length = 15
FEATURE                 Location/Qualifiers
source                  1..15
                        mol_type = other DNA
                        organism = synthetic construct
SEQUENCE: 27
aagaagaaga gaagg                                            15

SEQ ID NO: 28           moltype = DNA  length = 33
FEATURE                 Location/Qualifiers
source                  1..33
                        mol_type = other DNA
                        organism = synthetic construct
SEQUENCE: 28
ttaattcacc actattaaga caagataagc gcg                        33

SEQ ID NO: 29           moltype = DNA  length = 48
FEATURE                 Location/Qualifiers
source                  1..48
                        mol_type = other DNA
                        organism = synthetic construct
SEQUENCE: 29
tatatcacca cttatatacc ttctcttctt cttcgcgctt atcttgtc        48

SEQ ID NO: 30           moltype = DNA  length = 15
FEATURE                 Location/Qualifiers
source                  1..15
                        mol_type = other DNA
                        organism = synthetic construct
SEQUENCE: 30
ttcacacttc acttc                                            15
```